United States Patent
Zink et al.

(10) Patent No.: US 11,045,555 B2
(45) Date of Patent: Jun. 29, 2021

(54) PATHOGEN-SPECIFIC CARGO DELIVERY AND DIAGNOSTIC PLATFORM BASED ON MESOPOROUS SILICA NANOPARTICLES

(71) Applicant: The Regents of the University of California, Oakland, CA (US)

(72) Inventors: Jeffrey I. Zink, Sherman Oaks, CA (US); Bastian Ruehle, Los Angeles, CA (US); Marcus A. Horwitz, Los Angeles, CA (US); Daniel L. Clemens, Los Angeles, CA (US); Bai-Yu Lee Clemens, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/389,715

(22) Filed: Apr. 19, 2019

(65) Prior Publication Data
US 2019/0321486 A1 Oct. 24, 2019

Related U.S. Application Data

(60) Provisional application No. 62/661,271, filed on Apr. 23, 2018, provisional application No. 62/660,855, filed on Apr. 20, 2018.

(51) Int. Cl.
| | |
|---|---|
| *G01N 33/543* | (2006.01) |
| *A61K 47/69* | (2017.01) |
| *A61P 31/04* | (2006.01) |
| *A61K 39/12* | (2006.01) |
| *A61K 47/68* | (2017.01) |
| *A61P 31/12* | (2006.01) |
| *A61K 39/02* | (2006.01) |
| *A61K 39/00* | (2006.01) |

(52) U.S. Cl.
CPC .......... *A61K 47/6929* (2017.08); *A61K 39/02* (2013.01); *A61K 39/12* (2013.01); *A61K 47/6803* (2017.08); *A61K 47/6835* (2017.08); *A61K 47/6839* (2017.08); *A61P 31/04* (2018.01); *A61P 31/12* (2018.01); *G01N 33/54346* (2013.01); *A61K 2039/60* (2013.01)

(58) Field of Classification Search
CPC ............... A61K 2039/53; A61K 39/12; A61K 2039/55511; A61K 9/00; A61K 49/0423; A61K 35/763; A61P 31/22; B01D 15/363; B01D 15/362; B01D 15/166; C12M 47/10; C12M 47/12; B01J 41/20
See application file for complete search history.

(56) References Cited

U.S. PATENT DOCUMENTS

| | | | | |
|---|---|---|---|---|
| 8,409,876 | B2 * | 4/2013 | Wiesner | A61P 35/00 436/524 |
| 2014/0356415 | A1 * | 12/2014 | DeShong | A61K 39/095 424/450 |

OTHER PUBLICATIONS

Climent et al. (2009) "Controlled Delivery Systems Using Antibody-Capped Mesoporous Nanocontainers." *J. Am. Chem. Soc.* 131: 14075-14080.
Climent et al. (2012) "Antibody-capped mesoporous nanoscopic materials: design of a probe for the selective chromo-fluorogenic detection of finasteride." *ChemistryOpen* 1: 251-259.
Climent et al. (2013) "Selective, sensitive, and rapid analysis with lateral-flow assays based on antibody-gated dye-delivery systems: the example of triacetone triperoxide." *Chemistry* 19: 4117-4122.
Ruehle et al. (2017) "A Pathogen-Specific Cargo Delivery Platform Based on Mesoporous Silica Nanoparticles" *J. Am Chem. Soc.*, 139: 6663-6668 with Supporting Information [28 pages].
Xue and Zink, (2013) "An Enzymatic Chemical Amplifier Based on Mechanized Nanoparticles" *J. Am. Chem. Soc.*, 135: 17659-17662 [NIH Public Access—Author Manuscript, 7pp].

* cited by examiner

*Primary Examiner* — Bao Q Li
(74) *Attorney, Agent, or Firm* — Tom Hunter; Weaver Austin Villeneuve & Sampson LLP

(57) ABSTRACT

In various embodiments nanoparticle drug delivery vehicles are provided that specifically deliver a cargo to a target pathogenic organism. In certain embodiments the drug delivery vehicle comprises a mesoporous silica nanoparticle comprising a plurality of pores and an outer surface through which the pores are disposed; a cargo disposed in the pores; one or more antigens attached to the surface of the nanoparticle; an antibody that specifically binds the antigens and are bound to the antigens, wherein the antibody inhibits diffusion of the cargo out of the pores and permit release of the cargo when the drug delivery vehicle is in the presence of the antigen or a pathogen displaying the antigen.

18 Claims, 18 Drawing Sheets a)

b)

c) Measurement of LPS shed by *F. tularensis* grown on plates or in TSBC liquid culture

| Sample | Dilution Factor | LPS µg/ml (± S.E.) | LPS µg per 10⁹ bacteria | % LPS Shed |
|---|---|---|---|---|
| Plate Grown Supernate | 1 | 1.31 ± 0.17 | 0.05 | 0.21% |
| Plate Grown Bacterial Pellet | 400 | 1.53 ± 0.13 | 25.5 | |
| Broth Grown Supernate | 1 | 0.92 ± 0.04 | 0.23 | 0.64% |
| Broth Grown Bacterial Pellet | 100 | 1.43 ± 0.08 | 35.75 | |

*Fig. 7*

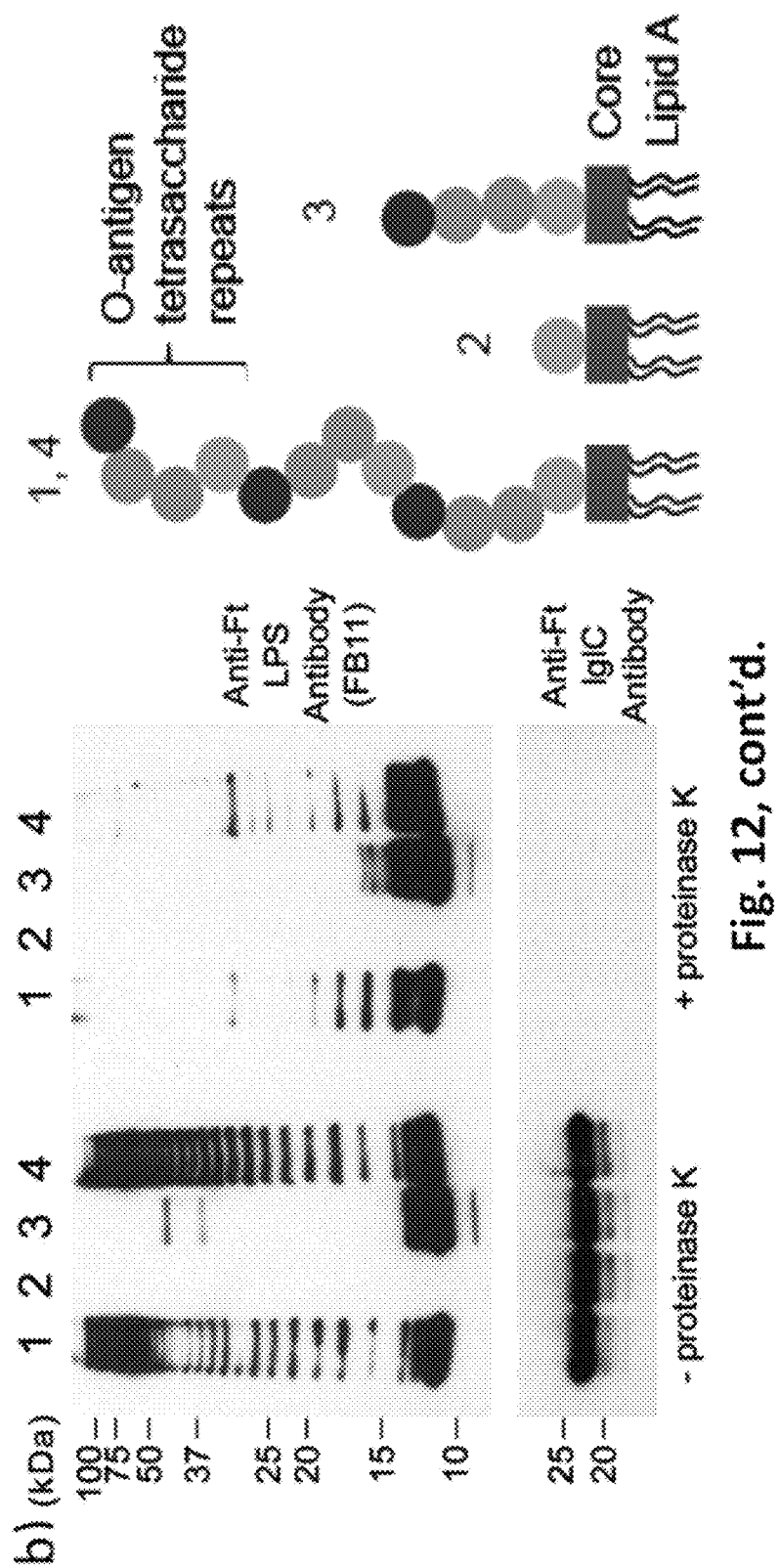
Fig. 12, cont'd.

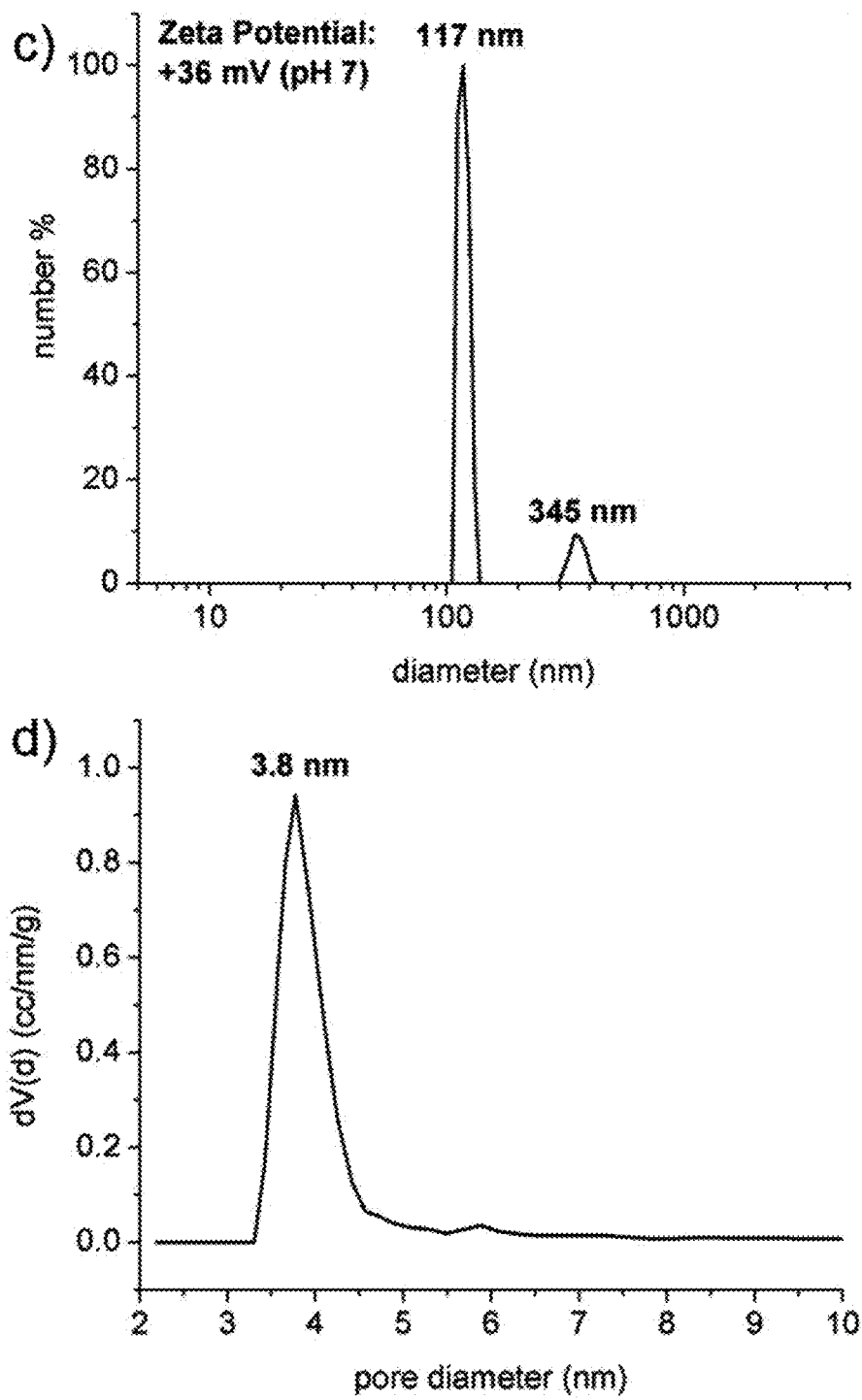
*Fig. 15, cont'd.*

PATHOGEN-SPECIFIC CARGO DELIVERY AND DIAGNOSTIC PLATFORM BASED ON MESOPOROUS SILICA NANOPARTICLES

CROSS-REFERENCE TO RELATED APPLICATIONS

This application claims priority to and benefit of U.S. Ser. No. 62/661,271, filed on Apr. 23, 2018 and U.S. Ser. No. 62/660,855, filed on Apr. 20, 2018, both of which are incorporated herein by reference in their entirety for all purposes.

STATEMENT OF GOVERNMENTAL SUPPORT

This invention was made with government support under Grant No. HDTRA1-13-1-0046 awarded by the U.S. Department of Defense, Defense Threat Reduction Agency. The Government has certain rights in the invention.

BACKGROUND

A cargo delivery platform that releases its payload specifically in the presence of a targeted pathogen would be highly beneficial for selectively detecting and treating infectious diseases. Not only can triggered drug release from a carrier system improve upon treatment with a free drug,[7,8] but a drug delivery platform that additionally releases its cargo only in the presence of a target pathogen could, in addition to signaling the presence of the pathogen in question, enhance efficacy by increasing drug delivery to infected cells while reducing the antibiotic burden on uninfected cells, thereby minimalizing unwanted side effects. Moreover, considering the ever-growing number of infections caused by antibiotic-resistant strains of bacteria, many arising from the use of broad spectrum antibiotics, and the adverse health consequences arising from alterations of the human microbiome by such broad-spectrum antibiotics, there is a need for greater selectivity in targeting pathogenic bacteria.

Making a drug delivery platform pathogen-specific poses several challenges. First, it is necessary to consider the "container" used to hold the payload that later is to be released specifically in the presence of the target pathogen. Next, one needs to address how a gatekeeping mechanism can be designed and implemented on this carrier that can act as a cap on the cargo-loaded pores and releases the cargo selectively in response to a specific pathogen. In nature, one way that highly selective recognition of target pathogens is achieved is through antibody-antigen inter-actions, and indeed, MSN-antibody conjugates have been reported that were used for analyte detection,[14-17] theranostics/imaging,[17-22] or cell targeting.[23-28] However, these examples demonstrate a specific recognition of an antigen by the MSN-antibody conjugate, but the recognition event itself does not stimulate a signal or killing response, i.e., there is no antigen-responsive gatekeeping mechanism that would selectively control cargo release only in the presence of a specific antigen or pathogen.

SUMMARY

We present a synthetic approach to a highly pathogen-selective detection and delivery platform based on the interaction of an antibody nanovalve with a tetrasaccharide from the O-antigen of the lipopolysaccharide (LPS) of *Francisella tularensis* bacteria, a Tier 1 Select Agent of bioterrorism. Different design considerations are explored, and proof-of-concept for highly pathogen-specific cargo release from mesoporous silica nanoparticles is demonstrated by comparisons of the release of a signal transducer and model drug by LPS from *F. tularensis* vs *Pseudomonas aeruginosa* and by *F. tularensis* live bacteria vs the closely related bacterium *Francisella novocida*. In addition to the specific response to a biowarfare agent, treatment of infectious diseases in general could benefit tremendously from a delivery platform that releases its antibiotic payload only at the site of infection and only in the presence of the target pathogen, thereby minimizing off-target toxicities.

While the proof-of-principle described herein focuses on *Francisella tularensis* using the O-antigen of the lipopolysaccharide (LPS) of *Francisella tularensis* in functional "nanovalve", it will be recognized by those of skill in the art that numerous other antigen-antibody combinations can be used in similar nanovalves configurations to target numerous other pathogens.

Various embodiments contemplated herein may include, but need not be limited to, one or more of the following:

Embodiment 1

An antigen- or pathogen-specific delivery vehicle, said vehicle comprising:
  a porous nanoparticle where said porous nanoparticle comprises a plurality of pores where said pores provide a pore surface inside the particle, and where said porous nanoparticle comprises an outer nanoparticle surface through which said pores are disposed;
  a cargo disposed in said pores;
  one or more antigens attached to the outer surface of said nanoparticle; and
  antibodies that specifically bind said antigens and are bound to said antigens, wherein said antibody inhibits diffusion of said cargo out of said pores and permit release of said cargo when said delivery vehicle is in the presence of said antigen or a pathogen displaying said antigen.

Embodiment 2

The delivery vehicle of embodiment 1, wherein said porous nanoparticle comprises a particle selected from the group consisting of a mesoporous silica nanoparticle, mesoporous hollow silica nanoparticle, and a mesoporous organosilica nanoparticle.

Embodiment 3

The delivery vehicle of embodiment 2, wherein said porous nanoparticle comprises a mesoporous silica nanoparticle.

Embodiment 4

The delivery vehicle according to any one of embodiments 1-3, wherein said cargo comprises an detectable label or an agent that kills a microorganism.

Embodiment 5

The delivery vehicle according to any one of embodiments 1-4, wherein said antigen is an antigen characteristic of a pathogen.

Embodiment 6

The delivery vehicle of embodiment 5, wherein said antigen is characteristic of a pathogen selected from the group consisting of a virus, a bacterium, and a parasite.

Embodiment 7

The delivery vehicle of embodiment 6, wherein said antigen is an antigen characteristic of a bacterium.

Embodiment 8

The delivery vehicle of embodiment 7, wherein said antigen is characteristic of a gram negative bacterium.

Embodiment 9

The delivery vehicle of embodiment 8, wherein said antigen is an antigen characteristic of a gram negative bacterium selected from the group consisting of *Franciscella*, *Burkholderia* (aka *Pseudomonas*), *Acinetobacter*, *Actinobacillus*, *Bordetella*, *Brucella*, *Campylobacter*, *Cyanobacteria*, *Enterobacter*, *Erwinia*, *Escherichia coli*, *Helicobacter*, Hemophilus, *Klebsiella*, *Legionella*, *Moraxella*, *Neisseria*, *Pasteurella*, *Proteus*, *Pseudomonas*, *Salmonella*, *Serratia*, *Shigella*, *Treponema*, *Vibrio*, and *Yersinia*.

Embodiment 10

The delivery vehicle according to any one of embodiments 8-9, wherein said antigen comprises a bacterial lipopolysaccharide or a domain or fragment thereof.

Embodiment 11

The delivery vehicle of embodiment 10, wherein said antigen comprises a bacterial lipopolysaccharide O-antigen from said gram negative bacteria.

Embodiment 12

The delivery vehicle of embodiment 11, wherein said antigen comprises a single O-antigen serotype.

Embodiment 13

The delivery vehicle of embodiment 11, wherein said antigen comprises a plurality of O-antigen serotype(s).

Embodiment 14

The delivery vehicle according to any one of embodiments 11-13, wherein said lipopolysaccharide is modified to comprise a single tetrasaccharide.

Embodiment 15

The delivery vehicle according to any one of embodiments 11-14, wherein said antigen comprises an O-antigen selected from the group consisting of *Franciscella* O-antigen, *Acinetobacter* O-antigen, *Actinobacillus* O-antigen, *Bordetella* O-antigen, *Brucella* O-antigen, *Campylobacter* O-antigen, *Cyanobacteria* O-antigen, *Enterobacter* O-antigen, *Envinia* O-antigen, *Escherichia coli* O-antigen, *Helicobacter* O-antigen, *Hemophilus* O-antigen, *Klebsiella* O-antigen, *Legionella* O-antigen, *Moraxella* O-antigen, *Neisseria* O-antigen, *Pasteurella* O-antigen, *Proteus* O-antigen, *Pseudomonas* O-antigen, *Salmonella* O-antigen, *Serratia* O-antigen, *Shigella* O-antigen, *Treponema* O-antigen, *Vibrio* O-antigen, and *Yersinia* O-antigen.

Embodiment 16

The delivery vehicle of embodiment 9, wherein said antigen is an antigen characteristic of *Franciscella tularensis*.

Embodiment 17

The delivery vehicle of embodiment 16, wherein said antigen comprises *Franciscella tularensis* O-antigen.

Embodiment 18

The delivery vehicle of embodiment 9, wherein said antigen is an antigen characteristic of *Burkholderia pseudomallei*.

Embodiment 19

The delivery vehicle of embodiment 7, wherein antigen is an antigen characteristic of a biowarfare pathogen.

Embodiment 20

The delivery vehicle of embodiment 19, wherein said antigen comprises an antigen characteristic of a pathogen selected from the group consisting of *Francisella tularensis* (tularemia), *Mycobacterium* (tuberculosis), *Bacillus anthracis* (anthrax), *Yersinia pestis* (plague), *Burkholderia pseudomallei* (melioidosis), *Coccidioides* spp. (coccidiomycosis,), *Aspergillus* spp. (aspergillosis), *Clostridium botulinum* (botulism), *Brucella* spp. (brucellosis), and *Variola* spp. (smallpox).

Embodiment 21

The delivery vehicle according to any one of embodiments 7-20, wherein said antibody is selected from the group consisting of an intact immunoglobulin, an $F(ab)'_2$, a Fab, a single chain antibody, a diabody, and affibody, a unibody, and a nanobody.

Embodiment 22

The delivery vehicle of embodiment 21, wherein said antibody is an intact immunoglobulin.

Embodiment 23

The delivery vehicle according to any one of embodiments 21-22, wherein said antibody is a monoclonal antibody.

Embodiment 24

The delivery vehicle according to any one of embodiments 21-23, wherein said antibody is a monoclonal antibody that binds to said O-antigen.

Embodiment 25

The delivery vehicle of embodiment 24, wherein said antibody is a monoclonal mouse anti-*Francisella tularensis* LPS antibody [FB11].

Embodiment 26

The delivery vehicle according to any one of embodiments 1-25, wherein said antigen is attached directly to said mesoporous silica nanoparticle.

Embodiment 27

The delivery vehicle according to any one of embodiments 1-25, wherein said antigen is attached to said mesoporous silica nanoparticle by a linker.

Embodiment 28

The delivery vehicle of embodiment 27, wherein said antigen is attached to said mesoporous silica nanoparticle by a linker comprising a silane.

Embodiment 29

The delivery vehicle of embodiment 27, wherein said antigen is attached to said mesoporous silica nanoparticle by a linker comprising a 3-(aminopropyl)triethoxysilane.

Embodiment 30

The delivery vehicle according to any one of embodiments 7-29, wherein said cargo comprise one or more antibiotics effective against bacteria.

Embodiment 31

The delivery vehicle of embodiment 30, wherein said cargo comprise one or more antibiotics effective against gram negative bacteria.

Embodiment 32

The delivery vehicle according to any one of embodiments 30-31, wherein said cargo comprises an antibiotic selected from the group consisting of a cephalosporin (e.g., ceftriaxone-cefotaxime, ceftazidime, and others), a fluoroquinolone (e.g., ciprofloxacin, levofloxacin), an aminoglycosides (e.g., gentamicin, amikacin), imipenem, a broad-spectrum penicillin with or without β-lactamase inhibitor(s) (e.g., amoxicillin-clavulanic acid, piperacillin-tazobactam), and trimethoprim-sulfamethoxazole.

Embodiment 33

The delivery vehicle of embodiment 6, wherein said antigen is characteristic of a virus.

Embodiment 34

The delivery vehicle of embodiment 33, wherein said antigen comprises an antigen characteristic of a virus selected from the group consisting of Dengue virus (Dengue fever), Ebola virus (Hemorrhagic fever), Herpes simplex virus type 1 and type 2 (Herpes), Human Immunodeficiency Virus (AIDS), Human papillomavirus (HPV), Influenza virus (Influenza), Japanese encephalitis virus (Japanese encephalitis), Marburg virus (Hemorrhagic fever), Pseudorabies virus (Aujeszky's disease), Rotavirus (Severe diarrhea).

Embodiment 35

The delivery vehicle of embodiment 34, wherein said antigen comprises a whole virus.

Embodiment 36

The delivery vehicle of embodiment 34, wherein said antigen comprises a viral coat (envelope) protein.

Embodiment 37

The delivery vehicle according to any one of embodiments 33-36, wherein said cargo comprises an antiviral agent.

Embodiment 38

The delivery vehicle of embodiment 37, wherein said cargo comprises an antiviral agent selected from the group consisting of an adamantane antiviral (e.g., amantadine, rimantadine), an antiviral booster (e.g., ritonavir, cobicistat), an antiviral interferon (e.g., peginterferon alfa-2b, peginterferon alpha-2a), a chemokine receptor antagonist (e.g., maraviroc), an integrase strand transfer inhibitor (e.g., raltegvavir, dolutegravir, elvitegravir), a neuraminidase inhibitor (e.g., zanamivir (RELENZA®), oseltamivir (TAMIFLU®), peramivir (RAPIVAB®), an NNRTI (e.g., etravirine, efavirenz, nevirapine, rilpivirine, delavirdine, nevapine), an NSSA inhibitor (e.g., daclatasvir), a nucleoside reverse transcriptase inhibitor (NRTI) (e.g., entecavir, lamivudine, adefovir, didanosine, abacavir, tenofovir, lamivudine, zidovudine, stavudine, emtricitabine, zalcitabine, telbivudine, alafenamide, didanosine), a protease inhibitor (e.g., boceprevir, simeprevir, lopinavir, fosamprenavir, darunavir, telaprevir, tipranavir, ritonavir, atazanavir, nelfinavir, amprenavir, inndinavir, saquinavir), a purine nucleoside (e.g., ribavirin, valacyclovir, famiclovir, acyclovir, rvalganciclovir, gancilovir, cidofovir), an antiviral combination (e.g., abacavir/lamivudine, emtricitabine/rilpivirine/tenofovir alafenamide, cobicistat/elvitegravir/emtricitabine/tenofovir, glecaprevir/pibrentasvir, efavirenz/emtricitabine/tenofovir, abacavir/lamivudine/zidovudine, emtricitabine/tenofovir, elbasvir/grazoprevir, ledipasvir/sofosbuvir, emtricitabine/rilpivirine/tenofovir, abacavir/dolutegravir/lamivudine, emtricitabine/tenofovir alafenamide, sofosbuvir/velpatasvir, cobicistat/elvitegravir/emtricitabine/tenofovir alafenamide, dasabuvir/ombitasvir/paritaprevir/ritonavir, lamivudine/zidovudine, cobicistat/darunavir, emtricitabine/tenofovir, emtricitabine/lopinavir/ritonavir/tenofovir, emtricitabine/nelfinavir/tenofovir, bictegravir/emtricitabine/tenofovir alafenamide, lamivudine/tenofovir, atazanavir/cobicistat, dolutegravir/rilpivirine, efavirenz/lamivudine/tenofovir, ombitasvir/paritaprevir/ritonavir, dasabuvir/ombitasvir/paritaprevir/ritonavir, and sofosbuvir/velpatasvir/voxilaprevir), an a miscellaneous antiviral (e.g., sofobuvir, enfuvirtide, foscarnet, letermovir, ibalizumab, formivirsen).

Embodiment 39

The delivery vehicle of embodiment 6, wherein said antigen is characteristic of a parasite.

Embodiment 40

The delivery vehicle of embodiment 33, wherein said antigen comprises an antigen characteristic of a parasite selected from the group consisting of a protozoan, a helminthe, a nematode, a cestode, a trematode, an amoeba, and a fungus.

Embodiment 41

The delivery vehicle according to any one of embodiments 39-40, wherein said antigen comprises an antigen characteristic of a parasite selected from the group consisting of *Babesia bovis* (Babesiosis), *Eimeria tenella* (hemorrhagic cecal coccidiosis), *Entamoeba histolytica* (Amebiasis), *Leishmania amazonensis* (Leishmaniasis), *Leishmania donovani* (Visceral leishmaniasis), *Leishmania major* (Cutaneous leishmaniasis), *Neospora caninum* (Neosporosis), *Plasmodium* spp. (Malaria), *Toxoplasma gondii* (Toxoplasmosis), *Trypanosoma cruzi* (Chagas Disease).

Embodiment 42

The delivery vehicle according to any one of embodiments 39-41, wherein said cargo comprises an agent selected from the group consisting of an antiprotozoal, an antihelmenthic, an antinematode, an anticestode, an antitrematode, an antiamoebic, and an antifungal.

Embodiment 43

The delivery vehicle of embodiment 42, wherein said cargo comprises an antifungal agent selected from the group consisting of Amphotericin B, Anidulafungin, Caspofungin, Fluconazole, Flucytosine, Isavuconazolet, Itraconazole, Micafungin, Posaconazole, and Voriconazole.

Embodiment 44

The delivery vehicle of embodiment 42, wherein said cargo comprises an antiprotozoal selected from the group consisting of melarsoprol, eflornithine, metronidazole, tinidazole, and miltefosine.

Embodiment 45

The delivery vehicle of embodiment 42, wherein said cargo comprises an antihelmenthic selected from the group consisting of albendazole, mebendazole, thiabendazole, fenbendazole, triclabendazole, flubendazole, abamectin, diethylcarbamazine, ivermectin, suramin, pyrantel pamoate, levamisole, niclosamide, oxyclozanide, praziquantel, octadepsipeptides (e.g., emodepside), aminoacetonitrile derivatives (e.g., monepantel), spiroindoles (e.g., derquantel), pelletierine sulphate, and artemisinin.

Embodiment 46

The delivery vehicle of embodiment 42, wherein said cargo comprises an antinematode selected from the group consisting of mebendazole, pyrantel pamoate, thiabendazole, diethylcarbamazine, and ivermectin.

Embodiment 47

The delivery vehicle of embodiment 42, wherein said cargo comprises an anticestode selected from the group consisting of niclosamide, praziquantel, albendazole.

Embodiment 48

The delivery vehicle of embodiment 42, wherein said cargo comprises an antitrematode such as praziquantel.

Embodiment 49

The delivery vehicle of embodiment 42, wherein said cargo comprises an antiamoebic selected from the group consisting of rifampin, and amphotericin B.

Embodiment 50

The delivery vehicle according to any one of embodiments 33-49, wherein said antibody is selected from the group consisting of an intact immunoglobulin, an F(ab)'$_2$, a Fab, a single chain antibody, a diabody, and affibody, a unibody, and a nanobody.

Embodiment 51

The delivery vehicle of embodiment 50, wherein said antibody is an intact immunoglobulin.

Embodiment 52

The delivery vehicle according to any one of embodiments 50-51, wherein said antibody is a monoclonal antibody.

Embodiment 53

The delivery vehicle according to any one of embodiments 50-52, wherein said antigen is attached directly to said mesoporous silica nanoparticle.

Embodiment 54

The delivery vehicle according to any one of embodiments 50-52, wherein said antigen is attached to said mesoporous silica nanoparticle by a linker.

Embodiment 55

The delivery vehicle of embodiment 54, wherein said antigen is attached to said mesoporous silica nanoparticle by a linker comprising a silane.

Embodiment 56

The delivery vehicle of embodiment 55, wherein said antigen is attached to said mesoporous silica nanoparticle by a linker comprising a 3-(aminopropyl)triethoxy silane.

Embodiment 57

A pharmaceutical formulation, said formulation comprising:
 a vehicle according to any one of embodiments 1-56; and
 a pharmaceutically acceptable carrier/excipient.

Embodiment 58

The formulation of embodiment 57, wherein said formulation is an emulsion, dispersion, or suspension.

Embodiment 59

The formulation of embodiment 58, wherein said suspension, emulsion, or dispersion is stable for at least 1 month, or at least 2 months, or at least 3 months, or at least 4 months, or at least 5 months, or at least 6 months when stored at 4° C.

Embodiment 60

The formulation according to any one of embodiments 57-59, wherein said formulation is formulated for administration via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 61

The formulation according to any one of embodiments 57-59, wherein said formulation is a sterile injectable.

Embodiment 62

The formulation according to any one of embodiments 57-61, wherein said formulation is a unit dosage formulation.

Embodiment 63

A method of preparing a delivery vehicle, said method comprising:
  providing a porous nanoparticle comprising a plurality of pores and an outer surface through which said pores are disposed and an antigen attached to the surface of said nanoparticle;
  loading a cargo into the pores comprising said mesoporous silica nanoparticle; and
  contacting said nanoparticle with an antibody that binds to said antigen thereby sealing said cargo into the pores of said nanoparticle.

Embodiment 64

The method of embodiment 63, wherein said porous nanoparticle comprises a mesoporous silica nanoparticle.

Embodiment 65

The method according to any one of embodiments 63-64, wherein said method produces a delivery vehicle according to any one of embodiments 1-56.

Embodiment 66

A method of treating a bacterial infection in a mammal, said method comprising administering to said mammal an effective amount of a delivery vehicle according to any one of embodiments 1-32, wherein said antigen comprises a bacterial antigen, said antibody comprises an antibody that binds to said bacterial antigen, and said cargo comprises an agent that is an anti-bacterial agent.

Embodiment 67

The method of embodiment 66, wherein said infection comprises an infection by a gram negative bacterium.

Embodiment 68

The method of embodiment 67, wherein said infection comprises an infection by a gram negative bacterium selected from the group consisting of *Franciscella, Acinetobacter, Actinobacillus, Bordetella, Brucella, Campylobacter, Cyanobacteria, Enterobacter, Erwinia, Escherichia coli, Helicobacter, Hemophilus, Klebsiella, Legionella, Moraxella, Neisseria, Pasteurella, Proteus, Pseudomonas, Salmonella, Serratia, Shigella, Treponema, Vibrio*, and *Yersinia*.

Embodiment 69

The method of embodiment 68, wherein said infection comprises an infection by *Francisella tularensis*.

Embodiment 70

A method of treating a viral infection in a mammal, said method comprising administering to said mammal an effective amount of a delivery vehicle according to any one of embodiments 1-6, 33-38, and 50-56, wherein said antigen comprises a viral antigen, said antibody comprises an antibody that binds to said viral antigen, and said cargo comprises an agent that is an antiviral agent.

Embodiment 71

The method of embodiment 70, wherein said viral infection comprises an infection by a virus selected from the group consisting of Dengue virus (Dengue fever), Ebola virus (Hemorrhagic fever), Herpes simplex virus type 1 and type 2 (Herpes), Human Immunodeficiency Virus (AIDS), Human papillomavirus (HPV), Influenza virus (Influenza), Japanese encephalitis virus (Japanese encephalitis), Marburg virus (Hemorrhagic fever), Pseudorabies virus (Aujeszky's disease), and Rotavirus (Severe diarrhea).

Embodiment 72

A method of treating a parasitic infection in a mammal, said method comprising administering to said mammal an effective amount of a delivery vehicle according to any one of embodiments 1-6, and 39-56, wherein said antigen comprises a viral antigen, said antibody comprises an antibody that binds to said viral antigen, and said cargo comprises an agent that is an antiviral agent.

Embodiment 73

The method of embodiment 72, wherein said parasitic infection comprises an infection by a parasite selected from the group consisting of a protozoan, a helminthe, a nematode, a cestode, a trematode, an amoeba, and a fungus.

Embodiment 74

The method according to any one of embodiments 66-73, wherein said mammal is a human.

Embodiment 75

The method according to any one of embodiments 66-73, wherein said mammal is a non-human mammal.

Embodiment 76

An antigen- or pathogen-specific delivery vehicle, said vehicle comprising:
a porous nanoparticle where said porous nanoparticle comprises a plurality of pores where said pores provide a pore surface inside the particle, and where said porous nanoparticle comprises an outer nanoparticle surface through which said pores are disposed;
a cargo disposed in said pores, where said cargo comprises a detectable label;
one or more antigens attached to the outer surface of said nanoparticle; and
antibodies that specifically bind said antigens and are bound to said antigens, wherein said antibody inhibits diffusion of said cargo out of said pores and permit release of said cargo when said delivery vehicle is in the presence of said antigen or a pathogen displaying said antigen.

Embodiment 77

The delivery vehicle of embodiment 76, wherein said porous nanoparticle comprises a particle selected from the group consisting of a mesoporous silica nanoparticle, mesoporous hollow silica nanoparticle, and a mesoporous organosilica nanoparticle.

Embodiment 78

The delivery vehicle of embodiment 77, wherein said porous nanoparticle comprises a mesoporous silica nanoparticle.

Embodiment 79

The delivery vehicle according to any one of embodiments 76-78, wherein said cargo comprises a detectable label selected from the group consisting of an enzymatic label, an a substrate for an enzymatic label, a fluorophore, a colorimetric label, and a radioactive label.

Embodiment 80

The delivery vehicle according to any one of embodiments 76-79, wherein said antigen is an antigen characteristic of a pathogen.

Embodiment 81

The delivery vehicle of embodiment 80, wherein said antigen is characteristic of a pathogen selected from the group consisting of a virus, a bacterium, and a parasite.

Embodiment 82

The delivery vehicle of embodiment 81, wherein said antigen is an antigen characteristic of a bacterium.

Embodiment 83

The delivery vehicle of embodiment 82, wherein said antigen is characteristic of a gram negative bacterium.

Embodiment 84

The delivery vehicle of embodiment 83, wherein said antigen is an antigen characteristic of a gram negative bacterium selected from the group consisting of *Franciscella*, *Burkholderia* (aka *Pseudomonas*), *Acinetobacter*, *Actinobacillus*, *Bordetella*, *Brucella*, *Campylobacter*, *Cyanobacteria*, *Enterobacter*, *Erwinia*, *Escherichia coli*, *Helicobacter*, *Hemophilus*, *Klebsiella*, *Legionella*, *Moraxella*, *Neisseria*, *Pasteurella*, *Proteus*, *Pseudomonas*, *Salmonella*, *Serratia*, *Shigella*, *Treponema*, *Vibrio*, and *Yersinia*.

Embodiment 85

The delivery vehicle according to any one of embodiments 83-84, wherein said antigen comprises a bacterial lipopolysaccharide or a domain or fragment thereof.

Embodiment 86

The delivery vehicle of embodiment 85, wherein said antigen comprises a bacterial lipopolysaccharide O-antigen from said gram negative bacteria.

Embodiment 87

The delivery vehicle of embodiment 86, wherein said antigen comprises a single O-antigen serotype.

Embodiment 88

The delivery vehicle of embodiment 86, wherein said antigen comprises a plurality of O-antigen serotype(s).

Embodiment 89

The delivery vehicle according to any one of embodiments 86-88, wherein said lipopolysaccharide is modified to comprise a single tetrasaccharide.

Embodiment 90

The delivery vehicle according to any one of embodiments 86-89', wherein said antigen comprises an O-antigen selected from the group consisting of *Franciscella* O-antigen, *Acinetobacter* O-antigen, *Actinobacillus* O-antigen, *Bordetella* O-antigen, *Brucella* O-antigen, *Campylobacter* O-antigen, *Cyanobacteria* O-antigen, *Enterobacter* O-antigen, *Erwinia* O-antigen, *Escherichia coli* O-antigen, *Helicobacter* O-antigen, *Hemophilus* O-antigen, *Klebsiella* O-antigen, *Legionella* O-antigen, *Moraxella* O-antigen, *Neisseria* O-antigen, *Pasteurella* O-antigen, *Proteus* O-antigen, *Pseudomonas* O-antigen, *Salmonella* O-antigen, *Serratia* O-antigen, *Shigella* O-antigen, *Treponema* O-antigen, *Vibrio* O-antigen, and *Yersinia* O-antigen.

Embodiment 91

The delivery vehicle of embodiment 84, wherein said antigen is an antigen characteristic of *Franciscella tularensis*.

Embodiment 92

The delivery vehicle of embodiment 91, wherein said antigen comprises *Franciscella tularensis* O-antigen.

Embodiment 93

The delivery vehicle of embodiment 84, wherein said antigen is an antigen characteristic of *Burkholderia pseudomallei*.

Embodiment 94

The delivery vehicle of embodiment 82, wherein antigen is an antigen characteristic of a biowarfare pathogen.

Embodiment 95

The delivery vehicle of embodiment 94, wherein said antigen comprises an antigen characteristic of a pathogen selected from the group consisting of *Francisella tularensis* (tularemia), *Mycobacterium* (tuberculosis), *Bacillus anthracis* (anthrax), *Yersinia pestis* (plague), *Burkholderia pseudomallei* (melioidosis), *Coccidioides* spp. (coccidiomycosis,), *Aspergillus* spp. (aspergillosis), *Clostridium botulinum* (botulism), *Brucella* spp. (brucellosis), and *Variola* spp. (smallpox).

Embodiment 96

The delivery vehicle according to any one of embodiments 82-95, wherein said antibody is selected from the group consisting of an intact immunoglobulin, an F(ab)'$_2$, a Fab, a single chain antibody, a diabody, and affibody, a unibody, and a nanobody.

Embodiment 97

The delivery vehicle of embodiment 96, wherein said antibody is an intact immunoglobulin.

Embodiment 98

The delivery vehicle according to any one of embodiments 96-97, wherein said antibody is a monoclonal antibody.

Embodiment 99

The delivery vehicle according to any one of embodiments 96-98, wherein said antibody is a monoclonal antibody that binds to said O-antigen.

Embodiment 100

The delivery vehicle of embodiment 99, wherein said antibody is a monoclonal mouse anti-*Francisella tularensis* LPS antibody [FB11].

Embodiment 101

The delivery vehicle according to any one of embodiments 76-100, wherein said antigen is attached directly to said mesoporous silica nanoparticle.

Embodiment 102

The delivery vehicle according to any one of embodiments 1-100, wherein said antigen is attached to said mesoporous silica nanoparticle by a linker.

Embodiment 103

The delivery vehicle of embodiment 102, wherein said antigen is attached to said mesoporous silica nanoparticle by a linker comprising a silane.

Embodiment 104

The delivery vehicle of embodiment 102, wherein said antigen is attached to said mesoporous silica nanoparticle by a linker comprising a 3-(aminopropyl)triethoxysilane.

Embodiment 105

The delivery vehicle according to any one of embodiments 30-104, wherein said cargo comprises an antibiotic selected from the group consisting of a cephalosporin (e.g., ceftriaxone-cefotaxime, ceftazidime, and others), a fluoroquinolone (e.g., ciprofloxacin, levofloxacin), an aminoglycosides (e.g., gentamicin, amikacin), imipenem, a broad-spectrum penicillin with or without β-lactamase inhibitor(s) (e.g., amoxicillin-clavulanic acid, piperacillin-tazobactam), and trimethoprim-sulfamethoxazole.

Embodiment 106

The delivery vehicle of embodiment 81, wherein said antigen is characteristic of a virus.

Embodiment 107

The delivery vehicle of embodiment 106, wherein said antigen comprises an antigen characteristic of a virus selected from the group consisting of Dengue virus (Dengue fever), Ebola virus (Hemorrhagic fever), Herpes simplex virus type 1 and type 2 (Herpes), Human Immunodeficiency Virus (AIDS), Human papillomavirus (HPV), Influenza virus (Influenza), Japanese encephalitis virus (Japanese encephalitis), Marburg virus (Hemorrhagic fever), Pseudorabies virus (Aujeszky's disease), Rotavirus (Severe diarrhea).

Embodiment 108

The delivery vehicle of embodiment 107, wherein said antigen comprises a whole virus.

Embodiment 109

The delivery vehicle of embodiment 107, wherein said antigen comprises a viral coat (envelope) protein.

Embodiment 110

The delivery vehicle of embodiment 81, wherein said antigen is characteristic of a parasite.

Embodiment 111

The delivery vehicle of embodiment 106, wherein said antigen comprises an antigen characteristic of a parasite selected from the group consisting of a protozoan, a helminthe, a nematode, a cestode, a trematode, an amoeba, and a fungus.

Embodiment 112

The delivery vehicle according to any one of embodiments 110-111, wherein said antigen comprises an antigen characteristic of a parasite selected from the group consisting of *Babesia bovis* (Babesiosis), *Eimeria tenella* (hemorrhagic cecal coccidiosis), *Entamoeba histolytica* (Amebiasis), *Leishmania amazonensis* (Leishmaniasis), *Leishmania donovani* (Visceral leishmaniasis), *Leishmania major* (Cutaneous leishmaniasis), *Neospora caninum* (Neosporosis), *Plasmodium* spp. (Malaria), *Toxoplasma gondii* (Toxoplasmosis), *Trypanosoma cruzi* (Chagas Disease).

Embodiment 113

The delivery vehicle according to any one of embodiments 106-112, wherein said antibody is selected from the group consisting of an intact immunoglobulin, an F(ab)'$_2$, a Fab, a single chain antibody, a diabody, and affibody, a unibody, and a nanobody.

Embodiment 114

The delivery vehicle of embodiment 113, wherein said antibody is an intact immunoglobulin.

Embodiment 115

The delivery vehicle according to any one of embodiments 113-114, wherein said antibody is a monoclonal antibody.

Embodiment 116

The delivery vehicle according to any one of embodiments 113-115, wherein said antigen is attached directly to said mesoporous silica nanoparticle.

Embodiment 117

The delivery vehicle according to any one of embodiments 113-115, wherein said antigen is attached to said mesoporous silica nanoparticle by a linker.

Embodiment 118

The delivery vehicle of embodiment 117, wherein said antigen is attached to said mesoporous silica nanoparticle by a linker comprising a silane.

Embodiment 119

The delivery vehicle of embodiment 118, wherein said antigen is attached to said mesoporous silica nanoparticle by a linker comprising a 3-(aminopropyl)triethoxysilane.

Embodiment 120

The delivery vehicle according to any one of embodiments 76-119, wherein said cargo comprises a fluorophore.

Embodiment 121

The delivery vehicle according to any one of embodiments 76-119, wherein said cargo comprises an enzymatic label.

Embodiment 122

The delivery vehicle of embodiment 121, wherein said cargo comprises an enzymatic label selected from the group consisting of a horseradish peroxidase (HRP), an alkaline phosphatase (AP), a glucose oxidase, and an esterase (e.g., liver esterase).

Embodiment 123

The delivery vehicle according to any one of embodiments 76-119, wherein said cargo comprises a substrate for an enzymatic label.

Embodiment 124

The delivery vehicle of embodiment 123, wherein said cargo comprises an enzymatic substrate selected form the group consisting of 5-carboxyfluorescein diacetate, 3,3',5, 5'-tetramethylbenzidine (TMB), 3,3'-diaminobenzedine (DAB), 2,2'-azino-bis(3-ethylbenzothiazoline-6-sulphonic acid (ABTS), (o-phenylenediamine dihydrochloride (OPD), Amplex Red, 3-amino-9-ethylcarbazole (AEC), homovanillic acid, luminol, VECTOR Red, VECTOR Blue, 5-bromo-4-chloro-3-indolyl phosphate/nitroblue tetrazolium, nitrotetrazolium blude chloride, and 3-nitrotetrazolium blue chloride, tetranitroblue tetrazolium chloride.

Embodiment 125

A method of detecting a microorganism in a sample, said method comprises:
  contacting a sample with a delivery vehicle according to any one of embodiments 76-124; and
  detecting a signal produced by said detectable label, where presence and/or intensity of said signal identifies the presence and/or quantity of said microorganism in said sample.

Embodiment 126

The method of embodiment 125, wherein the microorganism is a microorganism that carries/displays the antigen that is present on said delivery vehicle.

Embodiment 127

The method according to any one of embodiments 125-126, wherein said antigen is characteristic of a pathogen selected from the group consisting of a virus, a bacterium, and a parasite.

Embodiment 128

The method vehicle of embodiment 127, wherein said antigen is an antigen characteristic of a bacterium.

Embodiment 129

The method vehicle of embodiment 128, wherein said antigen is characteristic of a gram negative bacterium.

Embodiment 130

The method vehicle of embodiment 129, wherein:
said antigen is an antigen characteristic of a gram negative bacterium selected from the group consisting of *Franciscella, Burkholderia* (aka *Pseudomonas*), *Acinetobacter, Actinobacillus, Bordetella, Brucella, Campylobacter, Cyanobacteria, Enterobacter, Envinia, Escherichia coli, Helicobacter, Hemophilus, Klebsiella, Legionella, Moraxella, Neisseria, Pasteurella, Proteus, Pseudomonas, Salmonella, Serratia, Shigella, Treponema, Vibrio,* and *Yersinia*; and
said method identifies the presence and/or amount of a bacterium selected from the group consisting of *Franciscella, Burkholderia* (aka *Pseudomonas*), *Acinetobacter, Actinobacillus, Bordetella, Brucella, Campylobacter, Cyanobacteria, Enterobacter, Erwinia, Escherichia coli, Helicobacter, Hemophilus, Klebsiella, Legionella, Moraxella, Neisseria, Pasteurella, Proteus, Pseudomonas, Salmonella, Serratia, Shigella, Treponema, Vibrio,* and *Yersinia*.

Embodiment 131

The method vehicle according to any one of embodiments 129-130, wherein said antigen comprises a bacterial lipopolysaccharide or a domain or fragment thereof.

Embodiment 132

The method vehicle of embodiment 131, wherein said antigen comprises a bacterial lipopolysaccharide O-antigen from said gram negative bacteria.

Embodiment 133

The method vehicle of embodiment 132, wherein said antigen comprises a single O-antigen serotype.

Embodiment 134

The method vehicle of embodiment 132, wherein said antigen comprises a plurality of O-antigen serotype(s).

Embodiment 135

The method vehicle according to any one of embodiments 132-134, wherein said lipopolysaccharide is modified to comprise a single tetrasaccharide.

Embodiment 136

The method vehicle according to any one of embodiments 132-135, wherein said antigen comprises an O-antigen selected from the group consisting of *Franciscella* O-antigen, *Acinetobacter* O-antigen, *Actinobacillus* O-antigen, *Bordetella* O-antigen, *Brucella* O-antigen, *Campylobacter* O-antigen, *Cyanobacteria* O-antigen, *Enterobacter* O-antigen, *Erwinia* O-antigen, *Escherichia coli* O-antigen, *Helicobacter* O-antigen, *Hemophilus* O-antigen, *Klebsiella* O-antigen, *Legionella* O-antigen, *Moraxella* O-antigen, *Neisseria* O-antigen, *Pasteurella* O-antigen, *Proteus* O-antigen, *Pseudomonas* O-antigen, *Salmonella* O-antigen, *Serratia* O-antigen, *Shigella* O-antigen, *Treponema* O-antigen, *Vibrio* O-antigen, and *Yersinia* O-antigen.

Embodiment 137

The method vehicle of embodiment 130, wherein:
said antigen is an antigen characteristic of *Franciscella tularensis*; and
said method identifies the presence and/or amount of *Franciscella tularensis* in said sample/.

Embodiment 138

The method vehicle of embodiment 137, wherein said antigen comprises *Franciscella tularensis* O-antigen.

Embodiment 139

The method vehicle of embodiment 130, wherein:
said antigen is an antigen characteristic of *Burkholderia pseudomallei*; and
said method identifies the presence and/or amount of *Burkholderia pseudomallei* in said sample.

Embodiment 140

The method vehicle of embodiment 128, wherein antigen is an antigen characteristic of a biowarfare pathogen.

Embodiment 141

The method vehicle of embodiment 140, wherein:
said antigen comprises an antigen characteristic of a pathogen selected from the group consisting of *Francisella tularensis* (tularemia), *Mycobacterium* (tuberculosis), *Bacillus anthracis* (anthrax), *Yersinia pestis* (plague), *Burkholderia pseudomallei* (melioidosis), *Coccidioides* spp. (coccidiomycosis,), *Aspergillus* spp. (aspergillosis), *Clostridium botulinum* (botulism), *Brucella* spp. (brucellosis), and *Variola* spp. (smallpox); and
said method identifies the presence and/or amount of a pathogen selected from the group consisting of *Francisella tularensis* (tularemia), *Mycobacterium* (tuberculosis), *Bacillus anthracis* (anthrax), *Yersinia pestis* (plague), *Burkholderia pseudomallei* (melioidosis), *Coccidioides* spp. (coccidiomycosis,), *Aspergillus* spp. (aspergillosis), *Clostridium botulinum* (botulism), *Brucella* spp. (brucellosis), and *Variola* spp. (smallpox).

Definitions

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

The term "lipopolysaccharide (LPS)" also known as "lipoglycan" and "endotoxin" refers to a class of large molecules consisting of a lipid and a polysaccharide composed of O-antigen, outer core and inner core joined by a covalent bond. Lipopolysaccharides are typically found in the outer membrane of Gram-negative bacteria.

The term "antigen" or "target antigen" as used herein refer to a moiety that can be recognized (e.g., specifically bound) by an antibody. In certain embodiments the "target antigen" is an antigen that is characteristic of a microorganism (e.g., a pathogen) which indicates that the antigen is found on the surface (or in certain embodiments released by) a particular microorganism (e.g., bacterium, virus, parasite, etc.). In certain embodiments the target antigen is particular to a specific strain or species of microorganism and the drug delivery vehicle comprising that antigen preferentially or specifically releases cargo in the presence of that specific strain or species. certain embodiments the target antigen is particular to a specific genus of microorganism and the drug delivery vehicle comprising that antigen preferentially or specifically releases cargo in the presence of that specific genus. In certain embodiments the target antigen is particular to a specific class of microorganism (e.g., gram negative bacteria) and the drug delivery vehicle comprising that antigen preferentially or specifically releases cargo in the present of members of that specific class.

The term "cargo" as used herein refers to any moiety that can be contained in the pores of a nanoparticle comprising the drug delivery vehicle and that is to be delivered/released in the presence of the target antigen (or microorganism/pathogen bearing the target antigen). Illustrative cargos include, but are not limited to one or more antibacterial agents, antiviral agents, and/or antiparasitic agents, e.g., as described herein.

A "pharmaceutically acceptable carrier" as used herein is defined as any carrier suitable for containing the drug delivery vehicles described herein and compatible with administration to a subject (e.g., a human or non-human mammal). Pharmaceutically acceptable carriers include, but are not limited to any of the standard pharmaceutically acceptable carriers. The pharmaceutically acceptable carrier can include diluents, adjuvants, and vehicles, as well as carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19th ed.) describes formulations which can be used in connection with the silicasomes described herein.

As used herein, an "antibody" refers to a protein consisting of one or more polypeptides substantially encoded by immunoglobulin genes or fragments of immunoglobulin genes or derived therefrom that is capable of binding (e.g., specifically binding) to a target (e.g., to a target polypeptide). The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) Proc. Nat. Acad. Sci. USA, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example, Fab molecules can be displayed on a phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). In certain embodiments antibodies should include all that have been displayed on phage (e.g., scFv, Fv, Fab and disulfide linked Fv (see, e.g, Reiter et al. (1995) Protein Eng. 8: 1323-1331) as well as affibodies, unibodies, and the like.

The term "specifically binds", as used herein, when referring to a biomolecule (e.g., protein, nucleic acid, antibody, etc.), refers to a binding reaction that is determinative of the presence of a biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The terms "pore surface" or "internal pore surface" when used with respect to a porous particle refers to the walls of the pores inside the porous particle, while the terms "particle surface" or "particle outer surface" refers to the external surface of the porous particle and not to the internal pore surface.

The terms "delivery vehicle" and "drug delivery vehicle" are used interchangeably and reflect the fact that the cargo contained in the vehicle need not be a drug. Thus, for example, in certain embodiments, the cargo can comprise a detectable label or other moiety.

BRIEF DESCRIPTION OF THE DRAWINGS

FIG. 7 panels a-c, *F. tularensis* LVS was grown on plates and resuspended in TBS or grown in TSBC liquid culture, pelleted by centrifugation and LPS in the supernate and in the resuspended pellets was determined by competition ELISA using standards prepared in TBS or TSBC, respectively. Panel a) Standard curve showing competition ELISA detecting 0.4-12.5 µg/mL purified LPS in TBS. Panel b) Standard curve for competition ELISA detecting 0.4-12.5 µg/mL purified LPS in TSBC. Panel c) Table showing amount of LPS detected in the samples, amount of LPS per $10^9$ bacterial pellet or bacterial supernatant, and the percent of LPS shed from the bacteria growing on agar or in liquid culture. The experiment was conducted twice with similar results.

Immunostaining of the same particles as in a) after incubation for 5 h at room temperature in PBS with 2.5 mg/mL Ft-LVS-LPS. Panel c) Immunostaining of unloaded, APTES-functionalized, Ft-LVS-LPS coated, acetylated, and FB11 antibody-capped MSNs incubated in PBS for 5 h at room temperature without Ft-LVS-LPS (control sample; arrows indicate some of the fluorescent MSN; red channel fluorescence is shown in gray scale to give higher contrast). Panel d) Immunostaining of the same particles as in panel c), incubated for 5 h at room temperature in PBS with 2.5 mg/mL Ft-LVS-LPS (red channel fluorescence is shown in gray scale to give higher contrast). Top: brightfield-images. Bottom: Red fluorescence from Texas Red conjugated GAM secondary staining antibodies. The presence of strong red fluorescence in panels a) and c) indicates the successful attachment of Ft-LVS-LPS, while the absence of red fluorescence in panels b) and d) indicates the successful displacement of FB11 antibodies from the MSN surface in the presence of *Francisella tularensis* Live Vaccine Strain bacteria in vitro. Fixed exposure and gain settings were used for the fluorescence images of particles and the respective controls. Scale bars are 10 μm.

Figure 11:
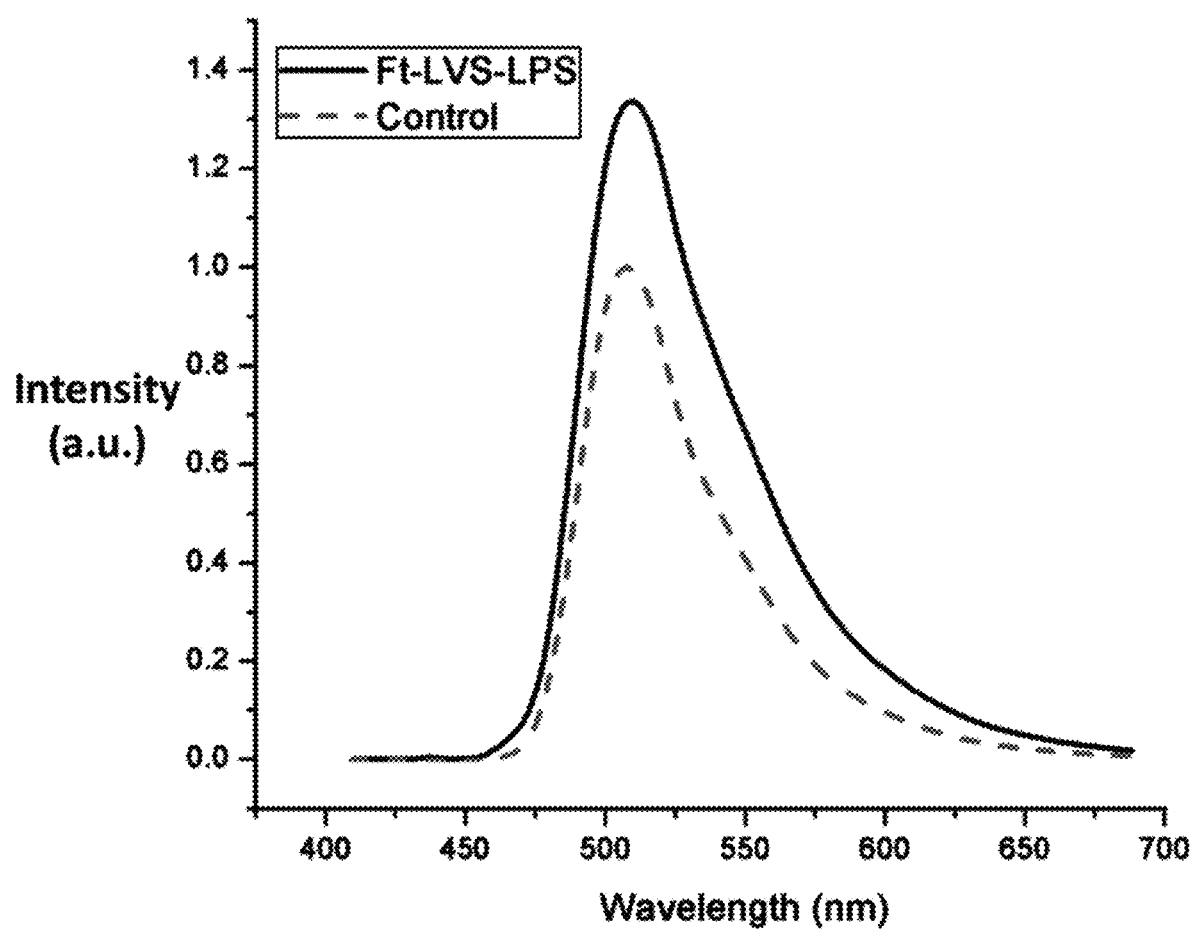

FIG. 11. Normalized fluorescence spectra of fluorescein-loaded, APTES-coated, Ft-LVS-LPS functionalized, acetylated, and FB11 antibody-capped MSNs after incubation with (black line) and without (red line) 5 mg/mL Ft-LVS-LPS in PBS (1×, pH=7.4) for 3 h at 37° C.

Figure 12:
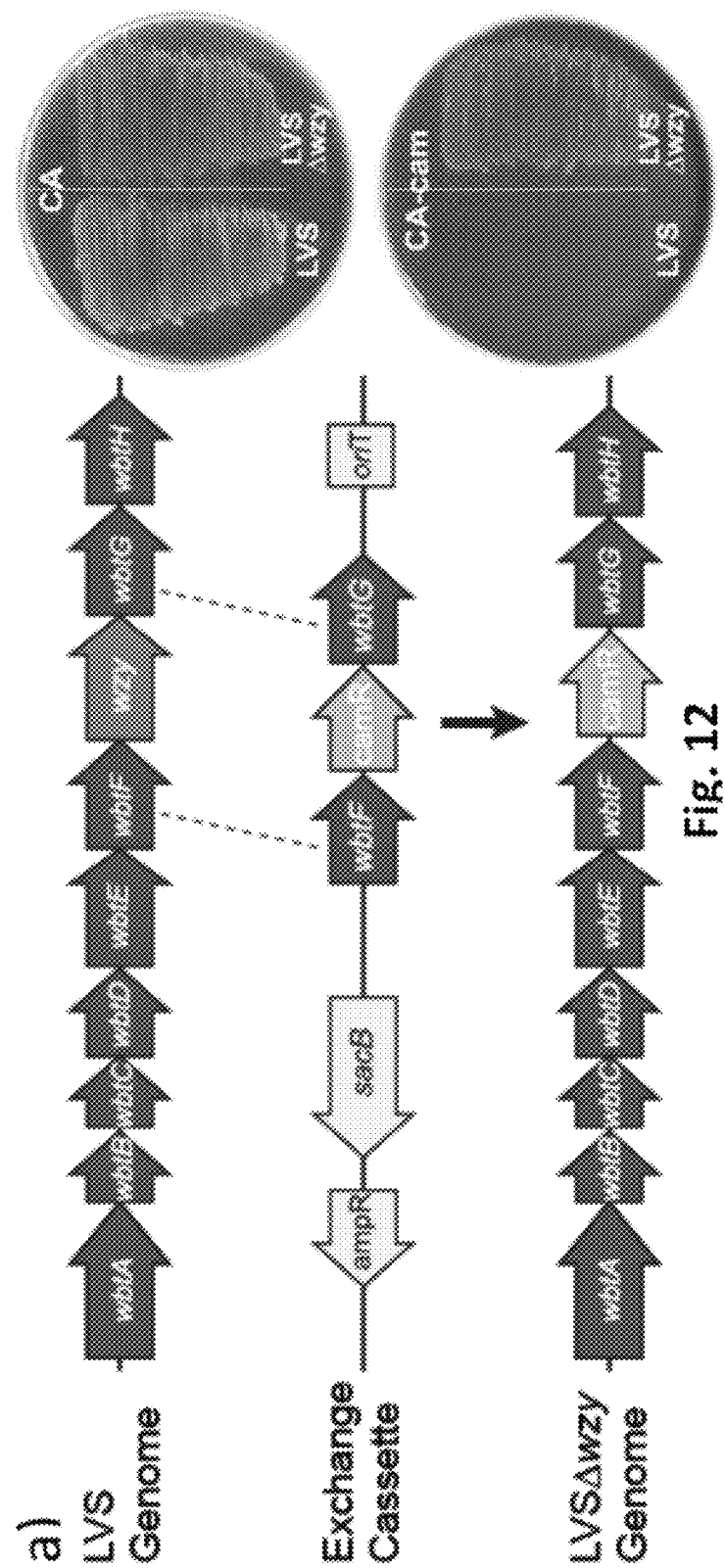

FIG. 12, panels a and b, illustrate generation and characterization of LVSΔwzy. Panel a) Left section: Organization of the wbtA-H gene cluster in *F. tularensis* Live Vaccine Strain (LVS) genome before (top) and after (bottom) replacing the wzy gene with the chloramphenicol resistant gene (camR) using a gene exchange cassette (middle). Right section: Unlike parental LVS, which grows on chocolate agar (CA) (upper plate) but not on chocolate agar containing chloramphenicol (CA-cam) (lower plate), LVSΔwzy is able to grow on chocolate agar with and without chloramphenicol. Panel b) Left upper panel: Immunoblotting analysis of parental LVS (lane 1), LVSΔwbtDEF (lane 2), LVSΔwzy (lane 3), and complemented LVSΔwzy (lane 4) using anti-*F. tularensis* LPS antibody FB11. Left lower panel: The IglC protein of *F. tularensis* serves as a loading control on the immunoblot. Right panel: Depiction of the LPS of Parental and O-antigen deficient LVS strains; numbering corresponds to the lanes of the immunoblot. The control strain LVSΔwbtDEF produces only a single saccharide of the O-antigen tetrasaccharide repeat and thus is not immunoreactive with the antibody FB11, which recognizes the three terminal saccharides of the single or terminal tetrasaccharide. LVSΔwzy is deficient in O-antigen polymerase and produces one unit of O-antigen tetrasaccharide. ampR, ampicillin resistance gene; sacB, *Bacillus subtilis* levansucrase sacB gene; oriT, origin of transfer.

Figure 5:
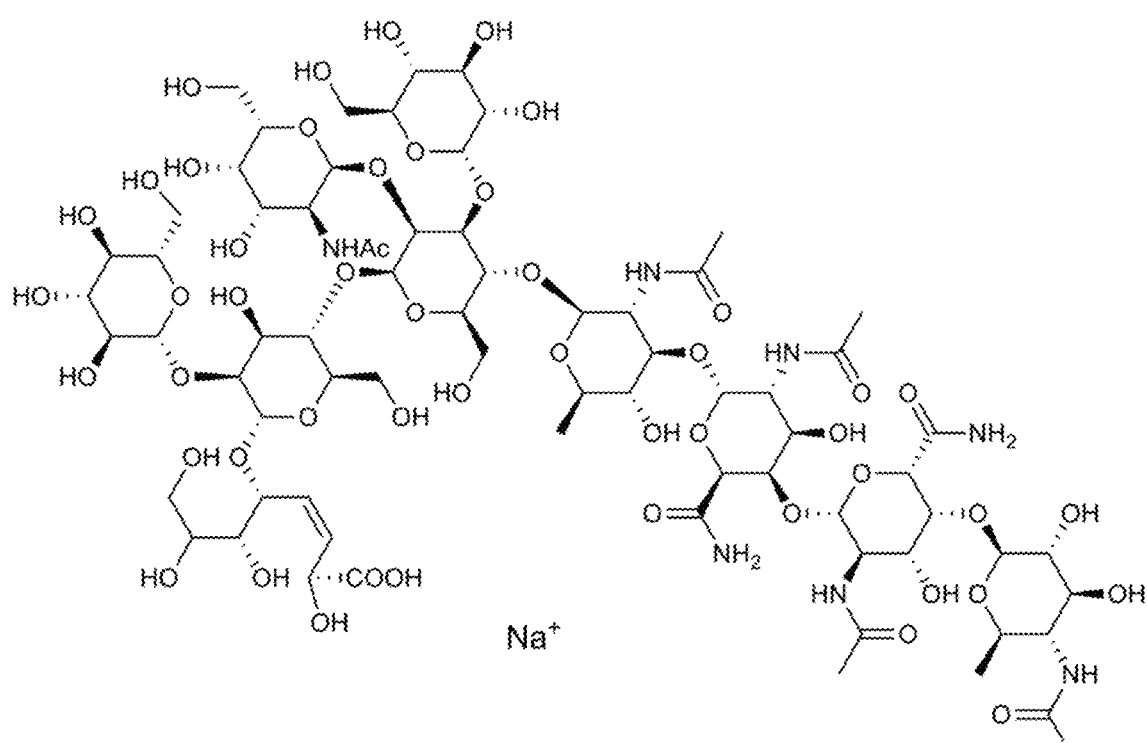
FIG. 5 illustrates the suggested structure of the sample isolated after careful hydrolysis of the lipid A part of the LPS from a wzy deletion mutant of Ft-LVS.
Figure 13:
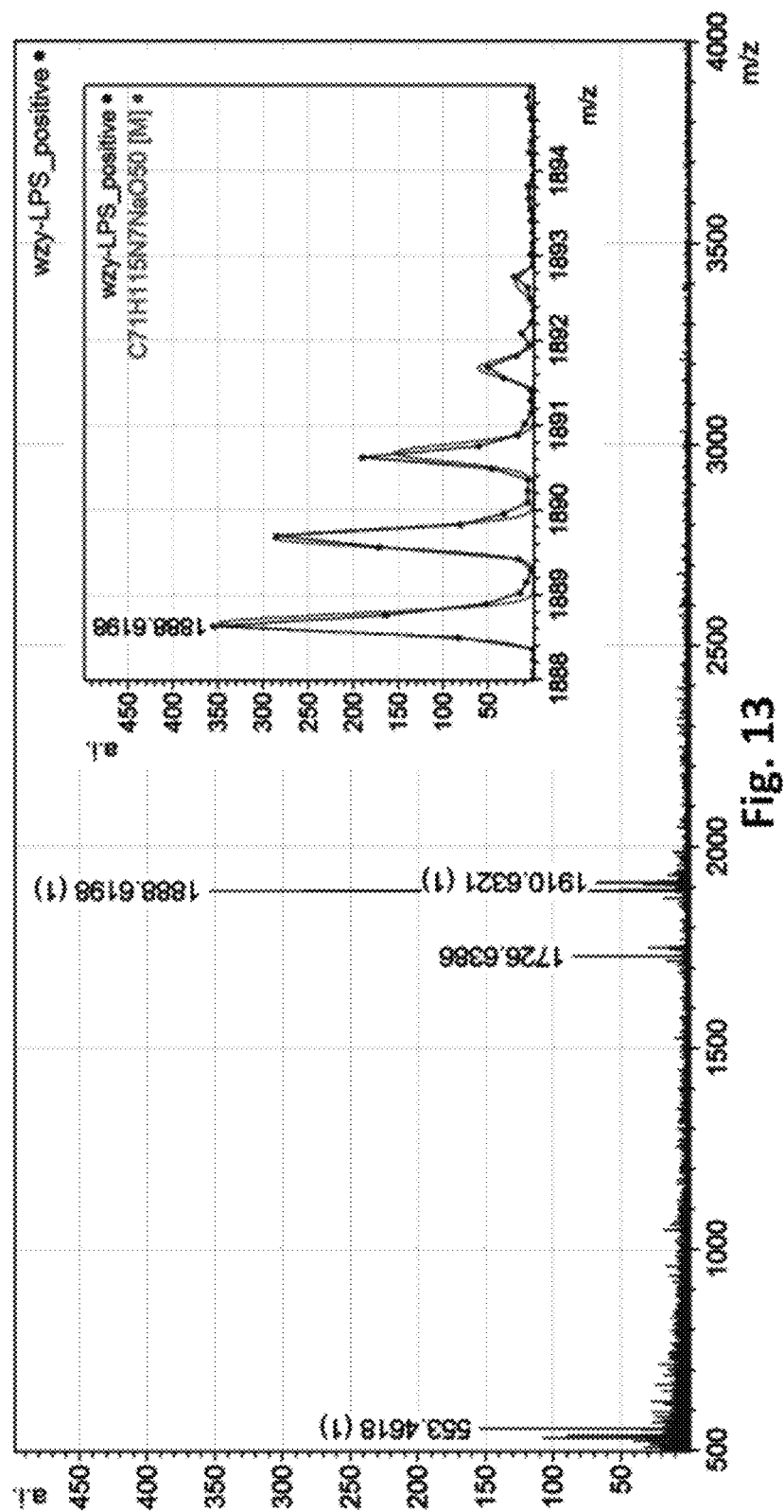

FIG. 13 shows MALDI-TOF MS data (positive channel) of the sample isolated after careful hydrolysis of the lipid A part of the LPS from a wzy deletion mutant of Ft-LVS. Inset: Experimental data (blue) and simulated data of the suggested structure (red) in FIG. 5.

Figure 14:
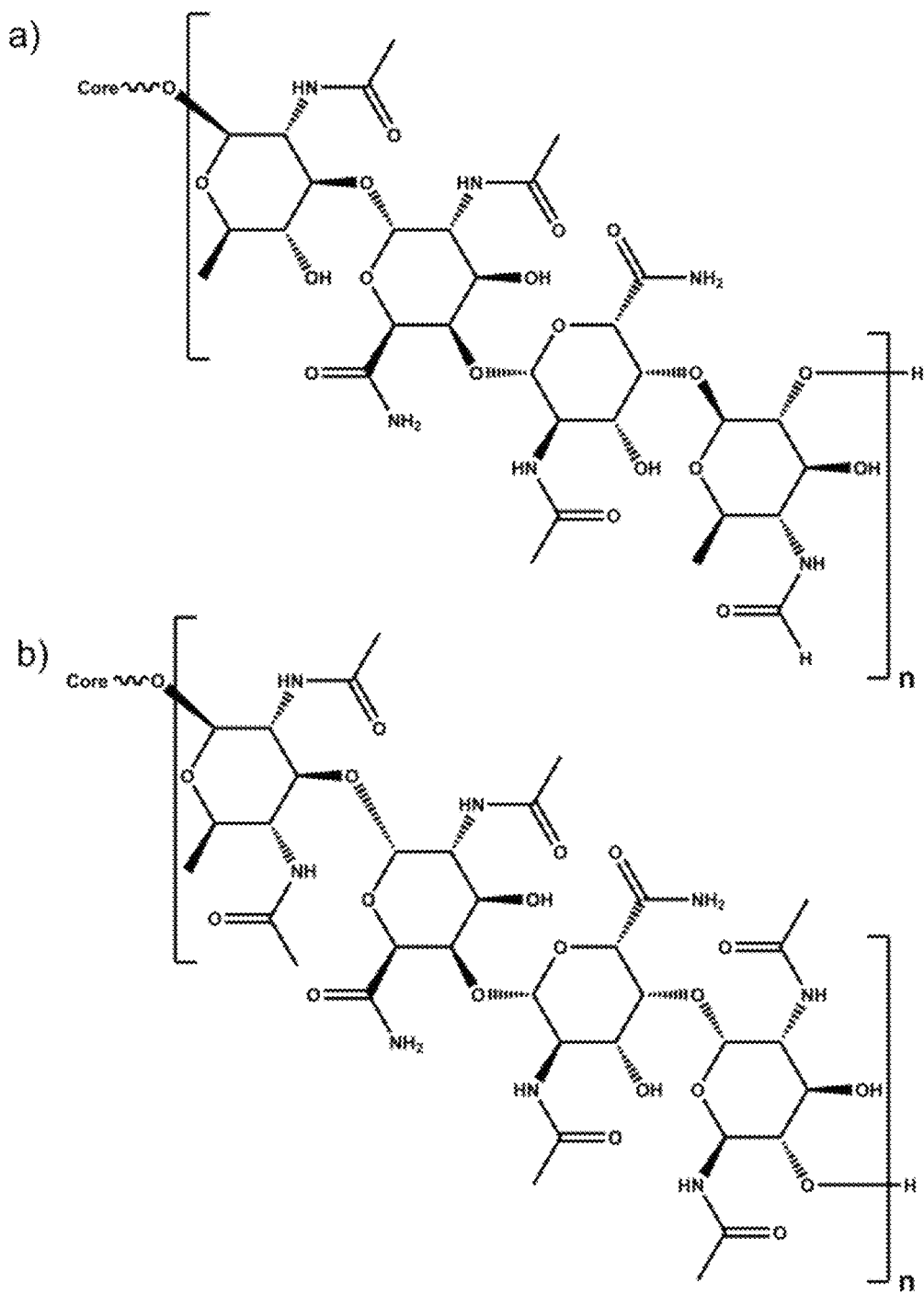

FIG. 14. Structure of the tetrasaccharide repeating unit in the O-antigen of a) *Francisella tularensis* and b) *Francisella novocida* (Vinogradov et al. (1991) *Carbohydr. Res.* 214: 289; Gunn & Ernst (2007) *Ann. N. Y. Acad. Sci.* 1105: 202). Despite the high structural similarity, release was highly specific to *Francisella tularensis* (see FIG. 6).

Figure 15:
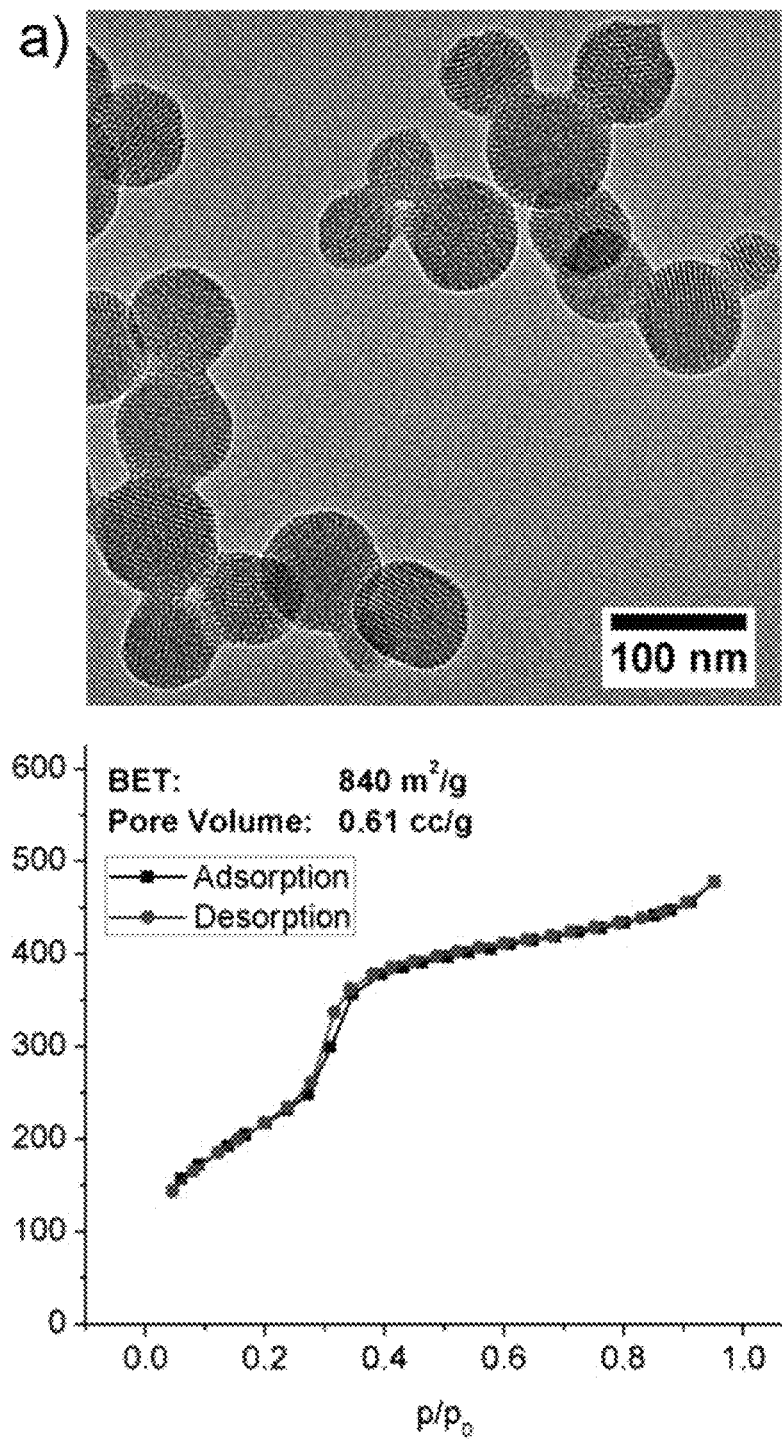

FIG. 15, panels a-d, show typical characterization data of APTES-functionalized MSN. Panel a) TEM micrograph showing the particle morphology and ordered mesoporosity. Panel b) Nitrogen sorption measurement showing a typical type IV isotherm, indicative of a mesoporous sample. A BET surface area of 840 $m^2$/g and a pore volume of 0.61 cc/g were calculated from the isotherms, confirming the high porosity of the sample. Panel c) DLS data and Zeta-potential measurement. The hydrodynamic diameter was 117 nm; a Zeta potential of +36 mV in di-Water at pH 7.0 indicates the successful functionalization with amine groups. Panel d) NLDFT pore size distribution calculated from the isotherms in b), giving a mesopore diameter of 3.8 nm.

Figure 16:
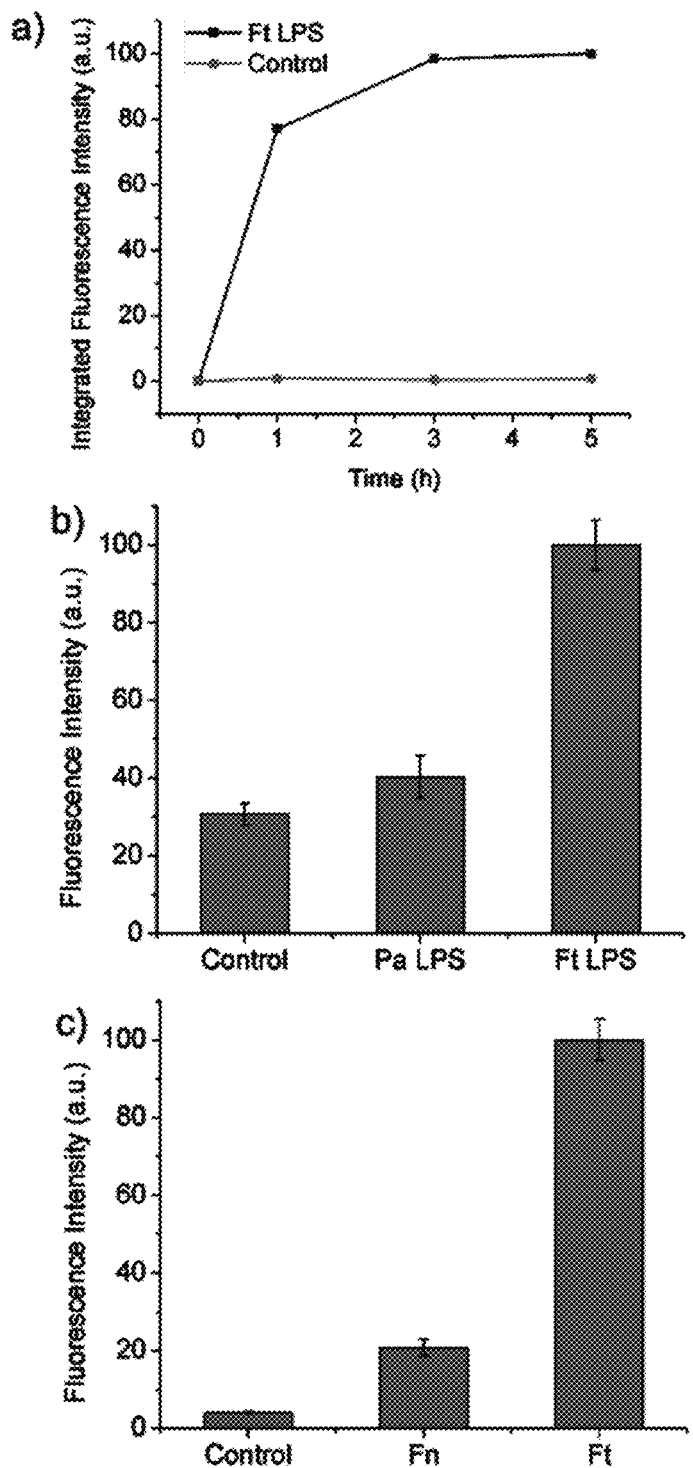

FIG. 16. Panel a) Time-based release of cargo (Hoechst 33342) in the presence (black squares) or absence (red dots) of 1 mg/ml purified Ft-LPS. Panel b) Nuclear staining intensity after release of Hoechst 33342 cargo triggered by incubation of MSNs with 1.0 mg/mL purified LPS from *Pseudomonas aeruginosa* (Pa LPS), 1.0 mg/mL *Francisella tularensis* (Ft LPS), and a control sample containing only PBS buffer for 1 h at 37° C. Panel c) Fluorescence intensity after release of a Hoechst 33342 cargo triggered by incubation of MSNs with live *Francisella novicida* bacteria (Fn), live *Francisella tularensis* bacteria (Ft), and a control sample containing only PBS for 1 h at 37° C.

DETAILED DESCRIPTION

In various embodiments a cargo delivery vehicle that provides highly specific release of a cargo contained therein in the presence of particular (e.g., predetermined) antigens or pathogens (or other moieties) bearing/presenting such antigens. In various embodiments, the drug delivery vehicles comprise a porous nanoparticle (e.g., a mesoporous silica nanoparticle (MSNP). One or more antigen(s) are attached to the surface of the nanoparticle and a cargo can be disposed inside the pores of the nanoparticle. When a loaded (cargo loaded) nanoparticle is contacted to an antibody that specifically (or preferentially) binds to the antigen the antibody binds to that antigen and effectively "caps" the particle sealing the cargo within the pores (see, e.g., FIGS. 1, and 2).

In the presence of the free antigen or a moiety (e.g., a pathogen) displaying the antigen, the antigen (free or displayed) competes with the antigen attached to the nanoparticle for binding by the antibodies capping the nanoparticle. This results in displacement of at least a portion of the capping antibodies thereby allowing cargo in the pores of the nanoparticle to leave (e.g., diffuse out of) the nanoparticle. The cargo is thus effectively delivered to the site of the antigen or, e.g., the site of pathogens bearing the antigen. Where the cargo is a therapeutic moiety (e.g., an antibiotic) this can result in increased concentrations of the moiety in the vicinity of the antigen (or pathogen bearing the antigen) with lower systemic exposure to the therapeutic moiety thereby increasing the available therapeutic window for the therapeutic moiety. Of course the cargo need not be limited to a therapeutic moiety. For example, in certain embodiments, the cargo can be a detectable moiety (e.g., a radiopaque moiety, a radioactive moiety, an MRI contrast agent, etc.) and be used to localize and/or quantify the target antigen (or microorganism bearing the target antigen).

As proof of principle, the Examples provided herein demonstrate a drug delivery vehicle (a cargo delivery platform) that features highly specific cargo release in vitro in the presence of the O-antigen of the lipopolysaccharide (LPS) of *Francisella tularensis* (Ft). Ft, the causative agent of tularemia, is a Tier 1 Select Agent of bioterrorism due to its high infectivity, capacity to cause serious morbidity and mortality (see, e.g., Saslaw et al. (1961) *Arch. Intern. Med.* 107: 702; Chocarro, A.; Gonzalez, A.; Garcia, I. Clin. Infect.

Dis. 2000, 31, 623; Feldman et al. (2001) *N. Engl. J. Med.* 345: 1601), and the relative ease with which it can be cultured on a large scale, weaponized, and dispersed into the environment. Ft was developed as a biological warfare agent during World War II by Japan and during the Cold War by both the U.S. and the former Soviet Union (see, e.g., Harris (1992) *Ann. N.Y. Acad. Sci.* 666: 21; Christopher et al. (1997) *JAMA,* 278: 412; Alibek & Handelman, *Biohazard: The Chilling True Story of the Largest Covert Biological Weapons Program in the World—Told from the Inside by the Man Who Ran It*, Reprint; Delta: New York, 2000). Because it can be fatal even with appropriate therapy, there is a need for both detection and responsive therapeutic treatment modalities such as our triggered, pathogen-responsive cargo delivery platform. Additionally, since numerous infectious diseases are caused by Gram-negative bacteria, which harbor LPS in their cell walls, the same design considerations and synthesis procedures can be applied to recognize and respond to many other pathogens.

As illustrated in the Examples provided herein, in one illustrative, but non-limiting embodiments, a prototypical drug delivery vehicle is provided where the vehicle comprises a porous nanoparticle (e.g., a mesoporous silica nanoparticle) comprising a plurality of pores and an outer surface through which the pores are disposed. When the vehicle is loaded, a cargo is disposed in the pores. One or more antigens are attached to the surface of said nanoparticle and antibodies that specifically bind the antigens are (non-covalently) bound to the antigens. In this configuration, the antibody inhibits diffusion of the cargo out of the pores and permits release of the cargo when the drug delivery vehicle is in the presence of the antigen or a moiety (e.g., a pathogen) displaying the antigen. In one embodiment, illustrated in the examples, the antigen comprises the O-antigen component of a *Francisella tularensis* lipopolysaccharide and the antibody comprises an intact monocolonal antibody (FM) that binds the *F. tularensis* O-antigen. In the illustrated embodiment, the antigen is attached to the nanoparticle by a linker comprising a silane.

The drug delivery vehicles are not limited to this particular antigen, and antibody, and linker. To the contrary, antigens characteristic of numerous microorganisms including, but not limited to other bacteria, viruses, parasites (including fungi), and the like are contemplated in which case the drug delivery vehicle will release the cargo in the presence of the targeted bacteria, virus, and/or parasite (or antigen therefrom). Additionally while capping is illustrated using a full-length antibody, in various embodiments the antibody can be an antibody fragment (e.g., Fab), a single chain antibody, a unibody, an affibody, and the like. In certain embodiments, the antibody can be replaced with a DNA or peptide aptamer that binds to the antigen and seals the pores in the nanoparticle. In certain embodiments the linker can be omitted (particularly where the antigen is large in which cases a portion of the antigen can function as a linker displaying the desired epitope which is bound by the antibody, aptamer, etc.). In certain embodiments different linkers such as are well known to those of skill in the art can readily be utilized.

In certain embodiments pharmaceutical formulations are provided where the formulations comprises a drug delivery vehicle as described herein and a pharmaceutically acceptable carrier/excipient.

Methods of treatment are also provided. In certain embodiments the methods of treatment comprise a method of treating a bacterial infection in a mammal, where the method involves administering to the mammal an effective amount of a drug delivery vehicle described herein that releases a cargo in the presence of the target bacterium and the cargo comprises an agent that is an anti-bacterial agent. In certain embodiments the infection comprises an infection by a gram negative bacterium (e.g., an infection by a gram negative bacterium such as *Franciscella, Acinetobacter, Actinobacillus, Bordetella, Brucella, Campylobacter, Cyanobacteria, Enterobacter, Erwinia, Escherichia coli, Helicobacter, Hemophilus, Klebsiella, Legionella, Moraxella, Neisseria, Pasteurella, Proteus, Pseudomonas, Salmonella, Serratia, Shigella, Treponema, Vibrio, Yersinia,* and the like).

In certain embodiments the methods of treatment comprise a method of treating a viral infection in a mammal, where the method involves administering to the mammal an effective amount of a drug delivery vehicle described herein that releases a cargo in the presence of the target virus and the cargo comprises an antiviral agent (e.g., as described herein).

In certain embodiments the methods of treatment comprise a method of treating a parasitic infection in a mammal, where the method involves administering to the mammal an effective amount of a drug delivery vehicle described herein that releases a cargo in the presence of the target parasite and the cargo comprises an agent that is an anti-parasitic agent (e.g., as described herein).

In certain embodiments the delivery vehicles described herein can readily be used for the detection and/or quantification of the presence of antigens, and in particular for the presence of, inter alia, various pathogens that bear the antigens used on the delivery vehicles. In one illustrative, but non-limiting embodiment the delivery vehicles can be designed to selectively and autonomously respond to a specific pathogenic biowarfare organism and signal its presence and/or amount. Pertinent to warfighter safety, this nanomaterial (delivery vehicle) is useful for field detection of disease-causing bacteria in general and in certain embodiments, various Tier 1 pathogens. In one illustrative, but non-limiting embodiment, the nanomaterial is useful for detection of the Tier 1 pathogen *Burkholderia pseudomallei* (Bp).

As explained above, the drug delivery vehicle can consist of mesoporous silica nanoparticles with signaling or therapeutic molecules trapped in the pores of the nanoparticle by stimulus-responsive caps that are opened by a specific molecule produced by the targeted pathogen. As described herein in Example 1, we have demonstrated the platform's utility and specificity in identifying the Tier 1 select agent *F. tularensis*. The specificity was based upon the highly specific interaction between a monoclonal antibody and the highly pathogen-specific O-Antigen of the lipopolysaccharide (LPS) of *F. tularensis*, leading to triggered release of signaling cargo molecules.

However, the delivery vehicles described herein can be uses as an autonomous amplified biosensing device where in the presence of a target antigen (e.g., a Bp capsular antigen) the delivery particle opens (releases the bound antibody) and exposes/releases a detectable label. In certain embodiments the detectable label comprises an enzyme that functions as an "amplifier" that results in catalytic production of fluorescent molecules that can then be readily detected. Traditional enzymatic amplification, such as ELISA, requires multiple steps. In contrast, in our design, the analyte recognition process exposes the enzyme amplifiers and turns on enzyme catalyzed fluorophore generation in a single step. This design eliminates the need for washing or separation procedures and can dramatically increase the detection sensitivity. In a previous study, we demonstrated an example of this type of design, which consisted of two components: a mesoporous silica matrix with encapsulated enzyme (porcine liver esterase, PLE) in the pores, and a pH-responsive supramolecular nanogate assembly to control access of the enzyme to its substrate (5-carboxyfluorescein diacetate, CFDA). CFDA does not fluoresce before undergoing hydrolysis, but the product is strongly fluorescent. We showed that acidification activates the nanogate, exposes the enzymes, and initiates an autonomously amplified chemical sensing process. Our rapid pathogen-specific diagnostic has the potential for employment in the field as point-of-care diagnosis of Bp or other pathogens.

As noted above, the delivery vehicles, when configured as a biosensing device need not be limited to the detection of *Burkholderia pseudomallei*. For example, in certain embodiments, the technology can be used to detect bioterrorism agents in the environment such as *Francisella tularensis* (tularemia), *Mycobacterium* (tuberculosis), *Bacillus anthracis* (anthrax), *Yersinia pestis* (plague), *Burkholderia pseudomallei* (melioidosis), *Coccidioides* spp. (coccidiomycosis,), *Aspergillus* spp. (aspergillosis), *Clostridium botulinum* (botulism), *Brucella* spp. (brucellosis), *Variola* spp. (smallpox), and the like.

This is readily accomplished by loading the pores with a cargo that could be detected such as a dye or fluorescent molecule and providing an antigen on the surface that is characteristic of one (or more) of these pathogens and capping a the delivery vehicle with an antibody that binds that antigen.

The vehicle is not limited to the detection of these pathogens and can be fabricated to detect essentially any pathogen in the environment, in a food, and the like.

Delivery Vehicle Antigen/Antibody—Target Organisms.

Delivery Vehicle Antigen(s).

As explained above, and in the examples provided herein, the delivery vehicles described herein exploit the binding interaction of an antibody (or an aptamer, etc.) and an antigen bound to a porous nanoparticle to effectively cap the nanoparticle trapping a cargo therein. In the presence of free antigen or moieties (e.g., microorganisms) displaying the antigen, the antibody is released from the nanoparticle thereby releasing the cargo. Thus, selection of an antigen and "cognate antibody (antibody that bind the antigen) determines the specificity of cargo release of the drug delivery vehicle.

In certain embodiments the cargo can comprise a moiety that kills a target organism bearing the antigen (e.g., one or more antibiotics) and the drug delivery vehicle acts to specifically or preferentially deliver the drug to the target organism. In certain embodiments the cargo can comprise a detectable label and the delivery vehicle can be used for the detection and/or quantification of target organism, e.g., in a biological sample.

Any of a wide variety of antigens can be exploited for this purpose and such antigens include but are not limited to bacterial antigens, viral antigens, and antigens from various parasites, including, but not limited to a protozoa, helminthes, nematodes, cestodes, trematodes, amoeba, fungi, and the like.

Figure 3:
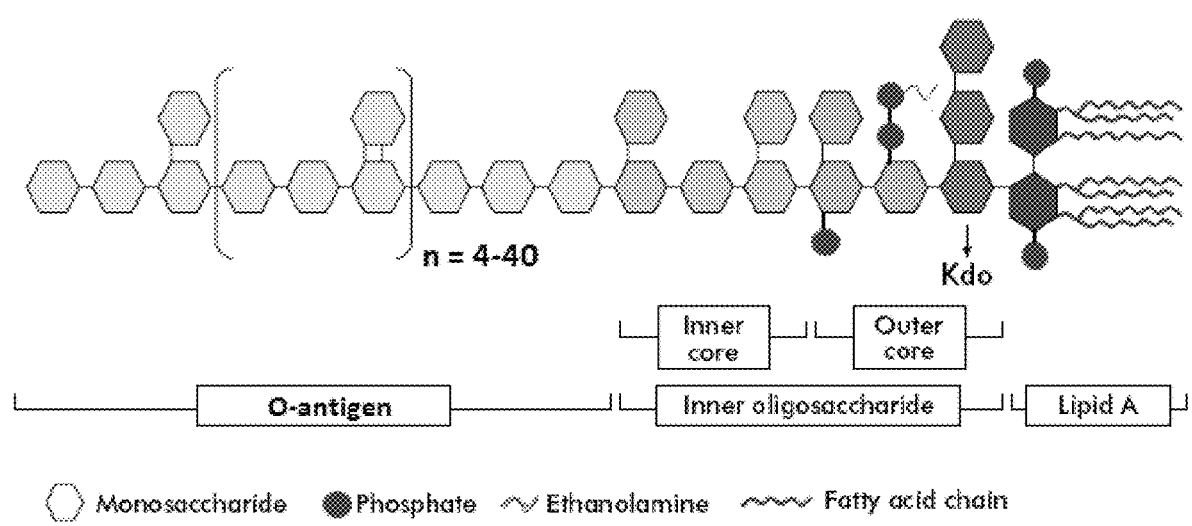
FIG. 3 illustrates a general structure for bacterial lipopolysaccharides. Abbreviations: KDO: 3 deoxy-α-D-mannooctulosonic acid.

One important antigen useful in the drug delivery vehicles described herein comprises a lipopolysaccharaide (LPS) or component thereof. Lipopolysaccharides (LPS), also known as lipoglycans and endotoxins, are large molecules consisting of a lipid and a polysaccharide composed of O-antigen, outer core and inner core joined by a covalent bond (see, e.g., FIG. 3). Lipopolysaccharides are typically found in the outer membrane of Gram-negative bacteria. The lipid A core is typically made up of a β-glucosamine-(1→6)-glucosamine-1-phosphate base with fatty acid esters attached to both carbohydrates. The acyl chain length and number of acyl groups can vary between bacterial species but are relatively conserved within a species. The inner polysaccharide core typically contains between 1 and 4 molecules of the KDO (3 deoxy-α-D-manno-octulosonic acid) attached to the disaccharide core. The KDO-containing inner core can also be modified with heptulose (ketoheptose) monosaccharides, the most common of which is L-glycero-α-D-manno-heptopyranose. The inner core glycan residues are typically phosphorylated or modified with phosphate-containing groups, e.g., pyrophosphate or 2 aminoethylphosphate. The outer core of the lipopolysaccharide contains more common hexoses, including glucose, galactose, and N-acetylglucosamine and is structurally more diverse than the inner core.

The O-antigen is a repeating oligosaccharide unit typically comprised of two to six sugars. The O-antigen is the primary structural constituent of lipopolysaccharide that differentiates bacteria. The distinctive O-antigen structures have been used to identify and assign serogroups to various bacteria (e.g., *Escherichia coli, Salmonella enterica, Vibrio cholerae*, and the like). The core section and the lipid A section of a lipopolysaccharide may have some variability in structure, while the O-antigen has a high degree of structural variability as well as variability in the number of repeating units.

As noted above, lipopolysaccharides are typically found in the outer membrane of Gram-negative bacteria and consequently drug delivery vehicles described herein comprising a LPS antigen and cognate antibody can be used to effectively deliver a cargo to a gram negative bacterium. In certain embodiments the antigen used in the drug-delivery vehicles described herein comprise the LPS O-antigen.

In certain embodiments, the LPS O-antigen utilized can be species and/or strain specific while in other embodiments a conserved LPS region/domain or a conserved O-antigen motif can be utilized which will provide broader specificity to the drug delivery vehicle.

The drug delivery vehicle described in the Examples provided herein utilizes the O-antigen from *Francisella tularensis*, however the drug delivery vehicles contemplated here are not so limited. LPS from essentially all gram negative bacteria are commercially available (e.g., LPS from *Bordetella pertussis, Salmonella Minnesota, Escherichia coli*, is available from LIST Biological Laboratories, Inc., and these and other LPSs can be purchased from numerous other suppliers). Isolation of O-antigen from LPS is readily done using standard protocols (see, e.g., Examples provided herein).

As explained above, selection of the particular LPS antigen can be used to "target" drug release to any strain, or species of gram negative bacterium or to various groups of gram negative bacteria. Where the cargo is an appropriate antibacterial agent the drug delivery vehicle can be used to inhibit and/or kill the target bacteria and thereby treat diseases caused by that bacterium.

Gram-negative bacteria are a group of bacteria that do not retain the crystal violet stain used in the gram-staining method of bacterial differentiation. They are typically characterized by their cell envelopes, which are composed of a thin peptidoglycan cell wall sandwiched between an inner cytoplasmic cell membrane and a bacterial outer membrane.

The gram negative bacteria are an important bacterial group implicated in numerous human and non-human animal diseases. The proteobacteria are a major phylum of gram-negative bacteria, including *Escherichia coli* (*E. coli*), *Salmonella, Shigella,* and other Enterobacteriaceae, *Pseudomonas, Moraxella, Helicobacter, Stenotrophomonas,* Bdellovibrio, acetic acid bacteria, *Legionella* etc. Other notable groups of gram-negative bacteria include the *cyanobacteria*, spirochaetes, green sulfur, and green non-sulfur bacteria. Medically relevant gram-negative cocci include the four types that cause a sexually transmitted disease (*Neisseria gonorrhoeae*), a meningitis (*Neisseria meningitidis*), and respiratory symptoms (*Moraxella catarrhalis, Haemophilus influenzae*). Medically relevant gram-negative bacilli include a multitude of species. Some of these cause primarily respiratory problems (e.g., *Klebsiella pneumoniae, Legionella pneumophila, Pseudomonas aeruginosa*), urinary problems (e.g., *Escherichia coli, Proteus mirabilis, Enterobacter cloacae, Serratia marcescens*), and gastrointestinal infections (e.g., *Helicobacter pylori, Salmonella enteritidis, Salmonella typhi*). Gram-negative bacteria associated with hospital-acquired infections include *Acinetobacter baumannii*, which cause bacteremia, secondary meningitis, and ventilator-associated pneumonia in hospital intensive-care units.

In certain embodiments the antigen used in the drug delivery vehicles contemplated herein is an antigen is an antigen characteristic of a gram negative bacterium selected from the group consisting of *Franciscella, Acinetobacter, Actinobacillus, Bordetella, Brucella, Campylobacter, Cyanobacteria, Enterobacter*, Envinia, *Escherichia coli, Helicobacter, Hemophilus, Klebsiella, Legionella, Moraxella, Neisseria, Pasteurella, Proteus, Pseudomonas, Salmonella, Serratia, Shigella, Treponema, Vibrio, Yersinia*, and the like. Accordingly, in certain embodiments the antigen comprises a bacterial lipopolysaccharide or a domain or fragment thereof from any one or more of these microorganisms. In certain embodiments the antigen comprises the O-antigen of a lipopolysaccharide from any one or more of these microorganisms.

The antigens comprising the drug delivery vehicles described herein need not be limited to gram positive antigens. Thus, for example, in certain embodiments the antigens can be derived from, inter alia, gram negative bacteria. Generally speaking, six gram positive genera are typically pathogenic in humans. Two of these, *Streptococcus* and *Staphylococcus*, are cocci (sphere-shaped). The remaining organisms are bacilli (rod-shaped) and can be subdivided based on their ability to form spores. The non-spore formers are *Corynebacterium* and *Listeria* (a coccobacillus), whereas *Bacillus* and *Clostridium* produce spores. The spore-forming bacteria can again be divided based on their respiration: *Bacillus* is a facultative anaerobe, while *Clostridium* is an obligate anaerobe. Gram-positive bacteria are capable of causing serious and sometimes fatal infections in newborn infants.

Illustrative pathogenic gram positive bacteria include, but are not limited to *Bacteroides fragilis* (bacilli that are opportunistic human pathogens, causing infections of the peritoneal cavity, e.g., after gastrointestinal surgery and appendicitis via abscess formation), *Clostridium difficile* (an anaerobic, spore-forming *bacillus* that is responsible for the development of antibiotic-associated diarrhea and colitis), *Corynebacterium jeikeium* (an opportunistic pathogen primarily of immunocompromised (neutropenic) patients.

In certain embodiments the antigen used in the drug delivery vehicles comprises a gram positive coat protein, or in the case of spore-forming gram positive bacteria, a spore polysaccharide and/or protein.

In certain embodiments the antigen used in the drug delivery vehicles comprises a viral antigen and the drug delivery vehicle releases its cargo in the presence of the target virus or viral antigen. Where the cargo in such a vehicle comprises an antiviral agent, the drug delivery vehicle can be used to treat a viral infection.

A number of pathogenic viruses are well known and well characterized and antigens from these viruses are readily available. For example, antigens characteristic of Zika virus include, but are not limited to Zika envelope domain 3, and Zika NS1, antigens characteristic of Ebola include, but are not limited o Ebola Zaire glycoprotein, Ebola zaire EP40, antigens characteristic of encephalitis virus (e.g., Japanese encephalitis virus) include, but are not limited to the virus ENV protein, antigens characteristic of tick-borne encephalitis virus include, but are not limited to GE and NS3, antigens characteristic of Cytomegalo virus include, but are not limited to gB, Pp150, Pp28, Pp52, Pp65, and the like, antigens characteristic of dengue virus include but are not limited to 1 &3 fused envelope protein, 1 & 4 fused envelope protein, and the like. These antigens are illustrative and non-limiting. Numerous suitable viral and bacterial antigens can readily be identified in the Protogen database (see, www.violinet.org/protegen/), and the like.

In certain embodiments the whole virus capsid, or a fragment thereof, can be attached to the nanoparticle to function as an antigen.

In certain embodiments the antigen comprise an antigen characteristic of a virus selected from the group consisting of Dengue virus (Dengue fever), Ebola virus (Hemorrhagic fever), Herpes simplex virus type 1 and type 2 (Herpes), Human Immunodeficiency Virus (AIDS), Human papillomavirus (HPV), Influenza virus (Influenza), Japanese encephalitis virus (Japanese encephalitis), Marburg virus (Hemorrhagic fever), Pseudorabies virus (Aujeszky's disease), Rotavirus (Severe diarrhea). In certain embodiments the antigen comprises a coat protein (or fragment thereof) of one of these viruses. In certain embodiments the antigen comprise a whole viral capsid or fragment thereof of one of these viruses.

In certain embodiments the antigen comprises an antigen characteristic of a parasite. Illustrative parasites include, but are not limited to protozoa, helminthes, nematodes, cestodes, trematodes, amoeba, fungi and the like. In certain embodiments illustrative, but non-limiting embodiments the antigen comprises an antigen characteristic of a parasite such as *Babesia bovis* (Babesiosis), *Eimeria tenella* (hemorrhagic cecal coccidiosis), *Entamoeba histolytica* (Amebiasis), *Leishmania amazonensis* (Leishmaniasis), *Leishmania donovani* (Visceral leishmaniasis), *Leishmania major* (Cutaneous leishmaniasis), *Neospora caninum* (Neosporosis), *Plasmodium* spp. (Malaria), *Toxoplasma gondii* (Toxoplasmosis), *Trypanosoma cruzi* (Chagas Disease), *Histoplasma capsulatum* (histoplasmosis), *Blastomyces dermatitidis* (blastomycosis), *Coccidioides immitis* or *Coccidioides posadasii* (Coccidioidomycosis), *Candida* spp. (Candidiasis), *Aspergillus* spp. (Aspergillosis), *Mucor* spp., *Rhizopus* spp., *Absidia* spp. and *Cunninghamella* spp. (Mucormycosis), *Fusarium* spp. (Fusariosis), and the like. In certain embodiments the antigen comprises a surface protein from any of these genuses or species or a fragment thereof.

Antibodies that Bind the Antigen.

As explained above, the porous nanoparticles are sealed (capped) by antibodies that bind (e.g., that specifically) bind to the antigen attached to the nanoparticle.

In certain embodiments the antibody is a full length (intact) immunoglobulin. In certain embodiments, the antibody comprises an intact immunoglobulin, or an F(ab)'$_2$, or a Fab, or a single chain antibody, or a diabody, or and affibody, or a unibody, or a nanobody.

In various embodiments antibodies that bind to the desired antigen are commercially available or can be fabricated to order by custom antibody suppliers (see, e.g. ThermoFisher, Inc., Pacific Antibody, Inc., and the like).

Antibodies that bind to the desired antigen can readily be fabricated using methods well known to those of skill in the art. In certain embodiments the antibodies include, but are not limited to, polyclonal antibodies, monoclonal antibodies (including, but not limited to IgG, IgA, IgM isotypes), as well as antibodies existing in a variety of other forms including, for example, Fv, Fab, and (Fab')$_2$, as well as bi-functional (e.g., bi-specific) hybrid antibodies, diabodies and other multimeric antibodies, single chain antibodies, unibodies, affibodies, nanobodies, and the like.

Monoclonal Antibody Production.

Monoclonal antibodies that bind the antigen to be used in the drug delivery vehicle can be produced using a variety of known techniques, such as the standard somatic cell hybridization technique described by Kohler and Milstein (1975) *Nature* 256: 495-497, viral or oncogenic transformation of B lymphocytes, or phage display technique using libraries of human antibody genes. In certain embodiments, the antibodies are fully human monoclonal antibodies.

Accordingly, in one embodiment, a hybridoma method is used for producing an antibody that binds the antigen to be used in the drug delivery vehicle. In this method, a mouse or other appropriate host animal can be immunized with an antigen described herein in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (see, e.g., Goding, Monoclonal Antibodies: Principles and Practice, pp. 59-103 (Academic Press, 1986)).

In various embodiments immortalized cell lines are usually transformed mammalian cells, particularly myeloma cells of rodent, bovine or human origin. In certain embodiments rat or mouse myeloma cell lines are employed. The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells Desirable immortalized myeloma cells include, but are not limited to, those that fuse efficiently, support stable high-level production of antibody by the selected antibody-producing cells, and are sensitive to a medium such as HAT medium. Among these are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (see, e.g., Kozbor (1984) *J. Immunol.*, 133: 3001; Brodeur et al. (1987) *Monoclonal Antibody Production Techniques and Applications*, pp. 51-63 (Marcel Dekker, Inc., New York).

Culture medium in which hybridoma cells are growing can be assayed for production of monoclonal antibodies directed against the target antigen.

After hybridoma cells are identified that produce antibodies of the desired specificity, affinity, and/or activity, the clones may be subcloned by limiting dilution procedures and grown by standard methods (see, e.g., Goding, Monoclonal Antibodies: Principles and Practice, pp. 59-103 (Academic Press, 1986)). Suitable culture media for this purpose include, for example, D-MEM or RPMI-1640 medium.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

In certain embodiments, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies directed against the antigen to be used in the drug delivery vehicle can also be made by recombinant DNA methods, such as those disclosed in U.S. Pat. No. 4,816,567. DNA encoding the monoclonal antibodies is readily isolated and sequenced using conventional procedures (e.g., by using oligonucleotide probes that specifically bind to genes encoding the heavy and light chains of murine antibodies). The hybridoma cells can serve as a source of such DNA. Once isolated, the DNA can be placed into expression vectors, which are then transfected into host-cells such as *E. coli* cells, simian COS cells, Chinese hamster ovary (CHO) cells, or myeloma cells that do not otherwise produce immunoglobulin protein, in order to synthesize monoclonal antibodies in such recombinant host-cells. Illustrative articles on recombinant expression in bacteria of DNA encoding the antibody include Skerra et al. (1993) *Curr. Opin. Immunol.*, 5: 256-262, Pliickthun (1992) *Immunol. Rev.* 130: 151-188, and the like.

In another illustrative embodiment, antibodies that bind the antigen to be used in the drug delivery vehicle can be isolated from antibody phage libraries generated using the techniques described in, for example, McCafferty et al. (1990) *Nature*, 348: 552-554, Clackson et al. (1991) *Nature*, 352: 624-628; Marks et al. (1991) *J. Mol. Biol.*, 222:581-597, Hoet et al. (2005) *Nature Biotechnology* 23: 344-348, U.S. Pat. Nos. 5,223,409; 5,403,484; and 5,571,698; 5,427,908, 5,580,717, 5,969,108, 6,172,197, 5,885,793, 6,521,404, 6,544,731, 6,555,313; 6,582,915, 6,593,081, and the like.

Additionally, production of high affinity (nM range) human antibodies by chain shuffling (Marks et al. (1992) *Bio/Technology*, 10:779-783, as well as combinatorial infection and in vivo recombination as a strategy for constructing very large phage libraries (Waterhouse et al. (1993) *Nuc. Acids. Res.*, 21: 2265-2266) may also be used.

In one illustrative embodiment, the monoclonal antibody that binds the antigen to be used in the drug delivery vehicle is produced using the phage display technique described by Hoet et al. (2005) *Nature Biotechnology* 23: 344-348. This technique involves the generation of a human Fab library having a unique combination of immunoglobulin sequences isolated from human donors and having synthetic diversity in the heavy-chain Fabs CDRs is generated. The library is then screened for Fabs that bind to the desired antigen.

In yet another embodiment, human monoclonal antibodies directed against the antigen to be used in the drug delivery vehicle can be generated using transgenic or transchromosomic mice carrying parts of the human immune system rather than the mouse system (see e.g., Lonberg et al. (1994) *Nature* 368(6474): 856-859; Lonberg, (1994) *Handbook of Experimental Pharmacology* 113: 49-101; Lonberg and Huszar (1995) *Intern. Rev. Immunol.* 13: 65-93, and Harding and Lonberg (1995) *Ann. N.Y. Acad. Sci.* 764:536-546. See also U.S. Pat. Nos. 5,545,806; 5,569,825; 5,625,126; 5,633,425; 5,789,650; 5,877,397; 5,661,016; 5,814,318; 5,874,299; 5,770,429; and 5,545,807, and PCT Publication Nos. WO 92/03918, WO 93/12227, WO 94/25585, WO 97/13852, WO 98/24884; WO 99/45962; and WO 01/14424.

In another illustrative embodiment, human antibodies human monoclonal antibodies that bind the antigen to be used in the drug delivery vehicle can be raised using a mouse that carries human immunoglobulin sequences on transgenes and transchomosomes, such as a mouse that carries a human heavy chain transgene and a human light chain transchromosome (see e.g., PCT Publication WO 02/43478).

Alternative transgenic animal systems expressing human immunoglobulin genes are available in the art and can be used to raise antibodies that bind the antigen to be used in the drug delivery vehicle. For example, an alternative transgenic system referred to as the Xenomouse (Abgenix, Inc.) can be used. Such mice are described in, for example, U.S. Pat. Nos. 5,939,598; 6,075,181; 6,114,598; 6, 150,584 and 6,162,963.

Additionally, alternative transchromosomic animal systems expressing human immunoglobulin genes are available in the art and can be used to raise antibodies that bind the antigen to be used in the drug delivery vehicle. For example, mice carrying both a human heavy chain transchromosome and a human light chain tranchromosome can be used; as described in Tomizuka et al. (2000) *Proc. Natl. Acad. Sci. USA* 97: 722-727. Cows carrying human heavy and light chain transchromosomes have been described in the art (Kuroiwa et al. (2002) *Nature Biotechnology* 20: 889-894) and can be used to raise antibodies that bind the antigen to be used in the drug delivery vehicle.

Antibody Fragments

In certain embodiments, antibody fragments of the antibodies that bind to the antigen to be used in the drug delivery vehicle are provided. Various methods are available for the production of antibody fragments. In certain embodiments fragments can be derived via proteolytic digestion of intact antibodies (see, e.g., Morimoto et al. (1992) *J. Biochem. Biophys. Meth.* 24: 107-117); Brennan et al. (1985) *Science* 229: 81; etc.). In certain embodiments these fragments can also be produced directly by recombinant host-cells, for example, using nucleic acids encoding the antibody fragments. Fab, Fv and scFv antibody fragments can all be expressed in and secreted from *E. coli*, thus allowing the straightforward production of large amounts of these fragments.

In certain embodiments the desired antibodies can also be isolated from the antibody phage display libraries. In certain embodiments Fab' fragments containing a cysteine (to provide Fab'-SH fragments) can be expressed in *E. coli* (or other expression system(s) and chemically coupled to form F(ab')$_2$ fragments (see, e.g., Carter et al. (1992) *Bio/Technology* 10: 163-167). In another approach, F(ab')$_2$ fragments can be isolated directly from recombinant host-cell culture.

In certain embodiments, the antibody can be a single chain Fv fragment (scFv), e.g., as described in PCT Pub. No: WO 93/16185, and U.S. Pat. Nos. 5,571,894 and 5,587,458. The antibody that binds the antigen to be used in the drug delivery carrier can also be a "linear antibody," e.g., as described in U.S. Pat. No. 5,641,870 and as described below. In certain embodiments the linear antibody fragments can be monospecific and in other embodiments, bispecific.

Nanobodies.

In certain embodiments the antibodies that bind the antigen to be used in the drug delivery vehicle are provided as nanobodies (sometimes referred to as camelid antibodies). Nanobodies are single domain antibodies (sdAb) typically consisting of a single monomeric variable antibody domain. Like whole antibodies (intact immunoglobulins), nanobodies are able to bind selectively to a specific antigen. With a molecular weight typically ranging from about 12 kDa to about 15 kDa, the single-domain nanobodies are much smaller than intact immunoglobulins which are typically composed of two heavy protein chains and two light chains. Nanobodies are also typically smaller than Fab fragments (~50 kDa, one light chain and half a heavy chain) and single-chain variable fragments (~25 kDa, two variable domains, one from a light and one from a heavy chain). Methods of producing nanobodies are described, inter alia, by Harmsen and Haard (2007) *Appl. Microbiol. Biotechnol.* 77 (1): 13-22).

Initially, nanobodies were engineered from heavy-chain antibodies found in camelids. These are called $V_HH$ fragments. Cartilaginous fishes also have heavy-chain antibodies (immunoglobulin new antigen receptor (IgNAR)'), from which single-domain antibodies called $V_{NAR}$ fragments can be obtained. An alternative approach is to split the dimeric variable domains from a common humans or other mammals (e.g., mice, rabbits, etc.) into monomers. Although most research into single-domain antibodies is based on heavy chain variable domains, nanobodies derived from light chains have also been shown to bind specifically to target epitopes (see, e.g., Möller et al. (2010) *J. Biol. Chem.* 285(49): 38348-38361). Single-domain camelids antibodies have been shown to be just as specific as a regular antibody and in some cases they are more robust. As well, they are easily isolated using the same phage panning procedure used for traditional antibodies, allowing them to cultured in vitro in large concentrations. The smaller size and single domain make these antibodies easier to transform into bacterial cells for bulk production, making them particularly useful.

Typically the single-domain antibody is a peptide chain about 110 amino acids long, comprising one variable domain (VH) of a heavy-chain antibody, or of a common IgG. These peptides have similar affinity to antigens as whole antibodies, but are more heat-resistant and stable towards detergents and high concentrations of urea. Those derived from camelid and fish antibodies are less lipophilic and more soluble in water, which, without being bound to a particular theory, is believed to be due to their complementarity determining region 3 (CDR3), which forms an extended loop covering the lipophilic site that normally binds to a light chain (see, e.g., Dolk et al. (2005) *Appl. Environ. Microbiol.* 71(1): 442-450; Stanfield et al. (2004) *Science,* 305(5691): 1770-1773).

The comparatively low molecular mass of nanobodies often leads to better permeability in tissues, and to a short plasma half-life since they are eliminated renally. Unlike whole antibodies, they do not show complement system triggered cytotoxicity because they lack an Fc region. However, in certain embodiments, it is contemplated that an immunoglobulin Fc region (or variant Fc region) can be fused to the nanobody to provide additional functionality. Camelid and fish derived sdAbs are able to bind to hidden antigens that may not be accessible to whole antibodies, for example to the active sites of enzymes. It is believed that this property has been shown to result from their extended CDR3 loop, which is able to penetrate such sites (see, e.g., Stanfield et al. (2004) Science 305(5691): 1770-1773; Desmyter et al. (1996) Nat. Struct. Biol. 3(9): 803-811).

In certain embodiments a single-domain antibody can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen.

In another embodiment a gene library from animals that have not been immunized beforehand is utilized. Such naïve libraries usually contain only antibodies with low affinity to the desired antigen. Accordingly affinity maturation by, for example, random mutagenesis may be utilized as an additional step.

When the most potent clones have been identified, their DNA sequence can be optimized, for example to improve their stability towards enzymes. Another goal is humanization to prevent immunological reactions of the human organism against the antibody. Humanization is generally not problematic because of the homology between camelid $V_HH$ and human $V_H$ fragments.

Typically, the final step in nanobody preparation is the translation of the optimized single-domain antibody in *E. coli*, *Saccharomyces cerevisiae* or other suitable organisms.

In certain embodiments nanobodies can also be produced from conventional antibodies, e.g. mammalian (e.g., murine or human) IgG with four chains.

Unibodies.

In certain embodiments the antibodies that bind the antigen to be used in the drug delivery vehicle(s) described herein are used to produce unibodies having the same or similar binding specificity. Unibodies are a stable, smaller antibody format with an anticipated longer therapeutic window than certain small antibody formats. In certain embodiments unibodies are produced from IgG antibodies (e.g., IgG4) by eliminating the hinge region of the antibody. Unlike the full size IgG4 antibody, the half molecule fragment is very stable and is termed a unibody. Halving the IgG4 molecule leaves only one area on the unibody that can bind to a target. Methods of producing unibodies are described in detail in PCT Publication WO2007/059782 and by Kolfschoten et al. (2007) Science 317: 1554-1557.

Affibodies.

In certain embodiments the antibodies that bind the antigen to be used in the drug delivery vehicle(s) described herein are used to construct affibody molecules that bind the target antigen. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of affibodies and methods of production are known to those of skill (see, e.g., U.S. Pat. No. 5,831,012).

The foregoing descriptions are illustrative and non-limiting. Using the teachings provided herein drug delivery vehicles comprising different antigens, different antibodies, and different methods of coupling the antigen(s) to the nanoparticle will be available to one of skill in the art.

Cargos.

The term "cargo" as used herein refers to any moiety that can be contained in the pores of a nanoparticle comprising the drug delivery vehicle and that is to be delivered/released in the presence of the target antigen (or microorganism/pathogen bearing the target antigen). Illustrative cargos include, but are not limited to one or more antibacterial agents, antiviral agents, and/or antiparasitic agents, e.g., as described herein. Thus, for example, where the drug delivery vehicle is "targeted to" bacteria, in certain embodiments the cargo can comprise one or more antibacterial compounds. Where the drug delivery vehicle is "targeted to" viruses, in certain embodiments the cargo can comprise one or more antiviral compounds. Where the drug delivery vehicle is "targeted to" bacteria, in certain embodiments the cargo can comprise one or more anti-parasitic compounds.

Antibacterial Compounds.

Illustrative antibacterial compounds that can be included as cargo in the drug delivery vehicles contemplated herein include, but are not limited to Penicillins, Tetracyclines, Cephalosporins, Quinolones, Lincomycins, Macrolides, Sulfonamides, Glycopeptides, Aminoglycosides, Carbapenems, and the like. Illustrative penicillins include, but are not limited to penicillin V potassium, amoxicillin, amoxicillin/clavulanate, and the like.

Illustrative tetracyclines include, but are not limited to doxycycline, tetracycline, minocycline, and the like. Illustrative cephalosporins include, but are not limited to cefadroxil, cefazolin, cefazolin, cefdinir, cefditoren, cefepime, cefixime, cefoperazone, cefotaxime, cefotetan, cefoxitin, cefpodoxime, cefprozil, ceftizoxime, ceftriaxone, cefuroxime, cephalexin, cephradine, loracarbef, loracarbef, and the like. Illustrative quinolones include, but are not limited to lomefloxacin, ofloxacin, norfloxacin, gatifloxacin, ciprofloxacin, moxifloxacin, ciprofloxacin, levofloxacin, gemifloxacin, delafloxacin, cinoxacin, nalidixic acid, trovafloxacin, sparfloxacin, and the like. Illustrative lincomycins include, but are not limited to clindamycin, lincomycin, and the like. Illustrative macrolides include, but are not limited to erythromycin, azithromycin, clarithromycin, fidaxomicin, and the like. Illustrative sulfonamides include, but are not limited to sulfamethoxazole/trimethoprim, sulfisoxazole, and the like. Illustrative glycopeptides include, but are not limited to vancomycin, oritavancin, dalbavancin, telavancin, and the like. Illustrative aminoglycosides, include, but are not limited to paromomycin, tobramycin, gentamicin, amikacin, kanamycin, neomycin, and the like. Illustrative carbapenems include, but are not limited to doripenem, meropenem, ertapenem, cilastatin/impenem, and the like.

In certain embodiments the antibiotic cargos comprise compounds (agents) known to be effective against gram negative bacteria. Illustrative antibiotics effective against gram negative bacteria include, but are not limited to a cephalosporin (e.g., ceftriaxone-cefotaxime, ceftazidime, and others), a fluoroquinolone (e.g., ciprofloxacin, levofloxacin), an aminoglycosides (e.g., gentamicin, amikacin), imipenem, a broad-spectrum penicillin with or without β-lactamase inhibitor(s) (e.g., amoxicillin-clavulanic acid, piperacillin-tazobactam), trimethoprim-sulfamethoxazole), and the like.

Antiviral Agents.

In certain embodiments the cargo in the drug delivery carriers described herein comprises a one or more antiviral agents. Illustrative antiviral agents include, but are not limited to:

1) adamantane antivirals (e.g., amantadine, rimantadine, and the like);
2) antiviral boosters (e.g., ritonavir, cobicistat, and the like);
3) antiviral interferons (e.g., peginterferon alfa-2b, peginterferon alpha-2a, and the like);
4) chemokine receptor antagonists (e.g., maraviroc, and the like);
5) integrase strand transfer inhibitors (e.g., raltegavvir, dolutegravir, elvitegravir, and the like);
6) neuraminidase inhibitors (e.g., zanamivir (RE-LENZA®), oseltamivir (TAMIFLU®), peramivir (RAPIVAB®), and the like);
7) NNRTIs (e.g., etravirine, efavirenz, nevirapine, rilpivirine, delavirdine, nevapine, and the like);
8) NSSA inhibitors (e.g., daclatasvir, and the like);
9) nucleoside reverse transcriptase inhibitors (NRTIs) (e.g., entecavir, lamivudine, adefovir, didanosine, abacavir, tenofovir, lamivudine, zidovudine, stavudine, emtricitabine, zalcitabine, telbivudine, alafenamide, didanosine, and the like);
10) protease inhibitors (e.g., boceprevir, simeprevir, lopinavir, fosamprenavir, darunavir, telaprevir, tipranavir, ritonavir, atazanavir, nelfinavir, amprenavir, inndinavir, saquinavir, and the like);
11) purine nucleosides (e.g., ribavirin, valacyclovir, famiclovir, acyclovir, rvalganciclovir, gancilovir, cidofovir, and the like);
12) antiviral combinations (e.g., abacavir/lamivudine, emtricitabine/rilpivirine/tenofovir alafenamide, cobicistat/elvitegravir/emtricitabine/tenofovir, glecaprevir/pibrentasvir, efavirenz/emtricitabine/tenofovir, abacavir/lamivudine/zidovudine, emtricitabine/tenofovir, elbasvir/grazoprevir, ledipasvir/sofosbuvir, emtricitabine/rilpivirine/tenofovir, abacavir/dolutegravir/lamivudine, emtricitabine/tenofovir alafenamide, sofosbuvir/velpatasvir, cobicistat/elvitegravir/emtricitabine/tenofovir alafenamide, dasabuvir/ombitasvir/paritaprevir/ritonavir, lamivudine/zidovudine, cobicistat/darunavir, emtricitabine/tenofovir, emtricitabine/lopinavir/ritonavir/tenofovir, emtricitabine/nelfinavir/tenofovir, bictegravir/emtricitabine/tenofovir alafenamide, lamivudine/tenofovir, atazanavir/cobicistat, dolutegravir/rilpivirine, efavirenz/lamivudine/tenofovir, ombitasvir/paritaprevir/ritonavir, dasabuvir/ombitasvir/paritaprevir/ritonavir, and sofosbuvir/velpatasvir/voxilaprevir, and the like);
13) Various miscellaneous antivirals (e.g., sofobuvir, enfuvirtide, foscarnet, letermovir, ibalizumab, formivirsen, and the like).

Antiparasitics.

In certain embodiments the cargo in the drug delivery carriers described herein comprises a one or more antiparasitic agents. Illustrative antiparasitic agents include, but are not limited to broad spectrum antiparasitics such as nitazoxanide, and the like.

In certain embodiments the antiparasitic comprises an antiprotozoal. Antiprotozoals include, but not limited to Melarsoprol (e.g., for treatment of sleeping sickness caused by *Trypanosoma brucei*) Eflornithine (e.g., for sleeping sickness) Metronidazole (e.g., for vaginitis caused by *Trichomonas*) Tinidazole (e.g., for intestinal infections caused by *Giardia lamblia*) Miltefosine (e.g., for the treatment of visceral and cutaneous leishmaniasis and Chagas disease), antinematode agents.

In certain embodiments the antiparasitic comprises an antihelmenthic. Illustrative antihelmenthics include but are not limited to benzimidazoles (e.g., albendazole (e.g., effective against threadworms, roundworms, whipworms, tapeworms, hookworms), mebendazole (e.g., effective against pinworms, roundworms and hookworms, and most nematodes), thiabendazole (e.g., effective against roundworms, hookworms), fenbendazole (e.g., effective against gastrointestinal parasites), triclabendazole (e.g., effective against liver flukes), flubendazole (e.g., effective against most intestinal parasites), abamectin (e.g., effective against most common intestinal worms, except tapeworms) Diethylcarbamazine (e.g., effective against *Wuchereria bancrofti, Brugia malayi, Brugia timori*, tropical pulmonary eosinophilia, loiasis and for lymphatic filariasis), Ivermectin (e.g., effective against most common internal parasites (e.g., except tapeworms) and effective for prevention of river blindness). Still other antiparasitics include, but are not limited to suramin (e.g., for treatment of human sleeping sickness caused by trypanosomes), levamisole, salicylanilides (e.g., niclosamide—effective against tapeworms, and the like.

In certain embodiments the antiparasitic comprises an antinematode. Illustrative anti-nematodes include, but are not limited to mebendazole, pyrantel pamoate, thiabendazole, diethylcarbamazine, ivermectin, and the like.

In certain embodiments the antiparasitic comprises an anticestode. Illustrative anticestodes include, but are not limited to niclosamide, praziquantel, albendazole, and the like.

In certain embodiments the antiparasitic comprises an anti-trematode (e.g., praziquantel, and the like).

In certain embodiments the antiparasitic comprises an anti-amoebic. Illustrative anti-amoebics include, but are not limited to rifampin, amphotericin B, and the like.

In certain embodiments the antiparasitic comprises an antifungal agent. Illustrative antifungal agents are shown in Table 1

TABLE 1

Illustrative antifungal drugs and target fungal infections.

| Antifungal | Target Infection |
| --- | --- |
| Amphotericin B | Most fungal infections |
| Anidulafungin | Candidiasis, including candidemia |
| Caspofungin | Aspergillosis, Candidiasis, including candidemia |
| Fluconazole | Mucosal and systemic candidiasis, Cryptococcal meningitis, Coccidioidal meningitis |
| Flucytosine | Candidiasis (systemic), Cryptococcosis |
| Isavuconazole† | Aspergillosis, Mucormycosis |
| Itraconazole | Dermatomycosis, Histoplasmosis, blastomycosis, coccidioidomycosis, sporotrichosis |
| Micafungin | Candidiasis, including candidemia |
| Posaconazole | Prophylaxis for invasive aspergillosis and candidiasis, Oral candidiasis. Oral candidiasis refractory to itraconazole |
| Voriconazole | Invasive aspergillosis, Candidiasis, Fusariosis, Scedosporiosis |

Detectable Labels

In certain embodiments the cargo comprises one or more detectable labels. Detectable labels include any composition detectable by spectroscopic, photochemical, biochemical, immunochemical, electrical, optical or chemical means. Useful labels include, but are not limited to, radiolabels (e.g., $^{3}H$, $^{125}I$, $^{35}S$, $^{14}C$, or $^{32}P$), enzymatic labels such as is commonly used in an ELISA (e.g., horseradish peroxidase (HRP), alkaline phosphatase (AP), glucose oxidase, an esterase (e.g., liver esterase), and the like), enzymatic label substrates (e.g., 5-carboxyfluorescein diacetate for an esterase, 3,3',5,5'-tetramethylbenzidine (TMB), 3,3'-diaminobenzedine (DAB), 2,2'-azino-bis(3-ethylbenzothiazoline-6-sulphonic acid (ABTS), (o-phenylenediamine dihydrochloride (OPD), Amplex Red, 3-amino-9-ethylcarbazole (AEC), homovanillic acid, luminol for a horse radish peroxidase, VECTOR Red, VECTOR Blue, 5-bromo-4-chloro-3-indolyl phosphate/nitroblue tetrazolium, and the like for an alkaline phosphatase, nitrotetrazolium blude chloride, 3-nitrotetrazolium bule chloride, tetranitroblue tetrazolium chloride, and the like for a glucose oxidase, and the like), fluorescent dyes (e.g., fluorescein isothiocyanate, texas red, rhodamine, green fluorescent protein), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}Tc$, $^{203}Pb$, $^{67}Ga$, $^{68}Ga$, $^{72}As$, $^{111}In$, $^{113m}In$, $^{97}Ru$, $^{62}Cu$, $^{64l}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{12}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$, and $^{111}Ag$.

Means of detecting such labels are well known to those of skill in the art. Thus, for example, certain radiolabels may be detected using photographic film, scintillation detectors, PET imaging, Mill, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The foregoing cargos are illustrative and non-limiting. Using the teachings provided herein, numerous other cargos can be incorporated into the drug delivery vehicles described herein.

Fabricating Drug Delivery Vehicles

In general the drug delivery vehicles described herein are fabricated by providing a porous nanoparticle (e.g., a mesoporous silica nanoparticle, or other porous particle) comprising a plurality of pores and an outer surface through which the pores are disposed and an antigen attached to the surface of the nanoparticle. A cargo is loaded into the pores comprising the nanoparticle and then the nanoparticle is contacted with an antibody that binds to the antigen thereby sealing the cargo into the pores of the nanoparticle.

Nanoparticles.

In various embodiments nanoparticle drug carriers described herein comprises a porous silica nanoparticle (e.g., a silica body having a surface and defining a plurality of pores that are suitable to receive molecules therein) with one or more antigens attached to the outer surface. In certain embodiments the silica nanoparticle can be a mesoporous silica nanoparticle. The fact that the nanoparticle is referred to as a silica nanoparticle does not preclude materials other than silica from also being incorporated within the silica nanoparticle. In some embodiments, the nanoparticle may be substantially spherical with a plurality of pore openings through the surface providing access to the pores. However, in various embodiments the silica nanoparticle can have shapes other than substantially spherical shapes. Thus, for example, in certain embodiments the nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm. In other embodiments, the pore diameters are between 1.5 and 2.5 nm. Silica nanoparticles having other pore sizes may be prepared, for example, by using different surfactants or swelling agents during the preparation of the silica nanoparticles.

In various embodiments the nanoparticles can include particles as large (e.g., average or median diameter (or other characteristic dimension) as about 1000 nm. However in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticle range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm. In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization technique.

Illustrative mesoporous silica nanoparticles include, but are not limited to MCM-41, MCM-48, and SBA-15 (see, e.g., Katiyaret al. (2006) *J. Chromatog.* 1122(1-2): 13-20).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (see, e.g., Trewyn et al. (2007) *Chem. Eng. J.* 137(1): 23-29. In certain embodiments mesoporous particles can also be synthesized using a simple sol-gel method (see, e.g., Nandiyanto, et al. (2009) *Microporous and Mesoporous Mat.* 120(3): 447-453, and the like). In certain embodiments tetraethyl orthosilicate can also be used with an additional polymer monomer (as a template). In certain embodiments 3-mercaptopropyl)trimethoxysilane (MPTMS) is used instead of TEOS.

In certain embodiments the mesoporous silica nanoparticles are cores were synthesized by a modification of the sol/gel procedure described by Meng et al. (2015) *ACS Nano*, 9(4): 3540-3557. To synthesize a batch of ~500 mg of MSNP, 50 mL of CTAC is mixed with 150 mL of $H_2O$ in a flask (e.g., a 500 mL conical flask), followed by stirring (e.g., at 350 rpm for 15 min at 85° C.). This us followed by the addition of 8 mL of 10% triethanolamine for 30 min at the same temperature. Then, 7.5 mL of the silica precursor, TEOS, is added dropwise at a rate of 1 mL/min using a peristaltic pump. The solution is stirred at 350 rpm at 85° C. for 20 min, leading to the formation particles with a primary size of ~65 nm. The surfactant can be removed by washing the particles with a mixture of methanol/HCl (500:19 v/v) at room temperature for 24 h. The particles can be centrifuged at 10 000 rpm for 60 min and washed three times in methanol.

While the drug delivery vehicles described herein have been demonstrated with respect to the porous silica nanoparticles (e.g., mesoporous silica), it will be recognized that similar drug delivery vehicles can utilize other porous nanoparticles. Numerous other mesoporous materials that can be used in drug delivery nanoparticles are known to those of skill in the art. For example, in certain embodiments mesoporous carbon nanoparticles could be utilized. Mesoporous carbon nanoparticles are well known to those of skill in the art (see, e.g., Huang et al. (2016) Carbon, 101: 135-142; Zhu et al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by Meng et al. (2006) *Chem. Mat.* 6(18): 4447-4464 and in the references cited therein.

The nanoparticles described herein are illustrative and non-limiting. Using the teachings provided herein numerous other drug delivery nanoparticles will be available to one of skill in the art.

Attachment of the Antigen to the Nanoparticle.

The antigen(s) used in the drug delivery carriers contemplated here can be attached to the nanoparticles by any of a number of methods well known to those of skill in the art. In certain embodiments the antigen can be attached directly to the nanoparticle. This can be particularly suitable where the antigen is larger than the epitope bound by the antibody and a portion of the antigen can function as a linker effectively displaying the epitope for binding by the antibody.

In certain embodiments the antigen is attached to the nanoparticle by a linker. Methods of chemically conjugating moieties to each other are well known to those of skill in the art. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982. Thus, the antigen can comprise or can be functionalized to comprise one or more reactive moieties, that facilitates the interaction of the antigen with a linker. In certain embodiments, the antigen and the nanoparticle form a conjugate in the absence of a linker, wherein the conjugate may be direct, e.g., by covalent bond.

Useful reactive moieties or functional groups used for conjugate chemistries herein depend on the antigen and nanoparticle material(s), and include, but are not limited to: a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; b) hydroxyl groups which can be converted to esters, ethers, aldehydes, etc.; c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; d) dienophile groups which are capable of participating in Diels-Alder reactions such as, for example, maleimido groups; e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; f) sulfonyl halide groups for subsequent reaction with amines, for example, to form sulfonamides; g) thiol groups, which can be converted to disulfides, reacted with acyl halides, or bonded to metals such as gold; (h) amine or sulfhydryl groups, which can be, for example, acylated, alkylated or oxidized; i) alkenes, which can undergo, for example, cycloadditions, acylation, Michael addition, etc.; j) epoxides, which can react with, for example, amines and hydroxyl compounds; k) phosphoramidites and other standard functional groups useful in nucleic acid synthesis; l) metal silicon oxide bonding; m) metal bonding to reactive phosphorus groups (e.g. phosphines) to form, for example, phosphate diester bonds; and n) sulfones, for example, vinyl sulfone.

The reactive functional groups can be chosen such that they do not participate in, or interfere with, the binding interaction of the antibody and the antigen when the antigen is attached to the nanoparticle.

In one illustrative, but non-limiting embodiment the antigen is attached to the nanoparticle using a silane (e.g., by functionalizing the nanoparticle with 3-(aminopropyl)triethoxysilane (APRES).

Loading of the Drug Delivery Vehicle.

The nanoparticle can be loaded by any of a number of methods well known to those of skill in the art. In certain embodiments the nanoparticles are loaded passively by simply soaking the nanoparticles in a solution containing the cargo molecule(s), e.g., as described herein in the Examples. In certain embodiments the surface of the pores of the nanoparticle can be modified with charged moieties to facilitate the loading of both negatively or positively charged molecules.

The loading efficiency of nanoparticles typically depends on factors such as electrostatic interactions between the nanoparticle and the loaded substance, surface tension and pH of the solute, concentration of loaded compound, time, temperature and the sizes of the pores (see, e.g., Liu et al. (2013) *Nanotechnology*, 24(41): 415501; Salonen et al. (2005) *J. Controlled Release*, 108: 362-374; Serda et al. (2011) *Biochimica et Biophysica Acta*, 1810: 317-329; and the like), and various loading methods can exploit these factors to optimize loading.

In certain embodiments loading can be accomplished using a passive incipient wetness method, by introducing a concentrated solution containing the cargo into a dry pellet of lyophilized nanoparticles particles to allow for passive capillary force to pull the liquid into pores (see, e.g., Serda et al. supra.). Other illustrative, but non-limiting loading procedures generally involve exposure of the loaded materials to organic solvents, including slow evaporation, melting, spray drying or rotary evaporation (see, e.g., Limnell et al. (2011) *J. Pharmaceut. Sci.* 100: 3294-3306).

In another illustrative, but non-limiting embodiment, loading can be accomplished using the application of low pressure with or without centrifugation (see, e.g., Lenoard et al. (2014) *Mesoporous Biomater.* 1(1): 10.2478; and the like).

These methods of loading cargo into the drug delivery vehicles described here are illustrative and non-limiting. Using the teachings provided herein, numerous other loading methods will be available to one of skill in the art.

Capping/Sealing of the Drug Delivery Vehicle.

After loading of the nanoparticle the pores are sealed by contacting antibodies that specifically bind the antigen on the surface of the nanoparticles to those nanoparticles. The antibodies bind the antigen effectively capping the nanoparticle and sealing the cargo in the pores. The antibodies are contacted with the nanoparticles under conditions where the antibodies are capable of binding the cognate antigen. Such conditions are well known to those of skill in the art. In one illustrative, but non-limiting embodiment, capping is accomplished by incubating the loaded nanoparticles in the presence of the antibody and BSA in PBS buffer, e.g., as illustrated in the examples.

Pharmaceutical Formulations, Administration and Therapy

Pharmaceutical Formulations.

In some embodiments, the drug delivery vehicles described herein are administered alone or in a mixture with a physiologically-acceptable carrier (such as physiological saline or phosphate buffer) selected in accordance with the route of administration and standard pharmaceutical practice. For example, when used as an injectable, the drug delivery vehicles can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In certain embodiments, in compositions comprising saline or other salt-containing carriers, the carrier is added following drug delivery vehicle formation. Thus, after the drug delivery vehicle is formed and loaded with suitable drug(s), the drug delivery vehicle can be diluted into pharmaceutically acceptable carriers such as normal saline. These compositions may be sterilized by conventional, well-known sterilization techniques. The resulting aqueous solutions, suspensions, dispersions, emulsions, etc., may be packaged for use or filtered under aseptic conditions. In certain embodiments the drug delivery vehicles are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

In various embodiments, the concentration of drug delivery vehicles in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, drug delivery vehicles composed of irritating components may be diluted to low concentrations to lessen inflammation at the site of administration. The amount of drug delivery vehicles administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

In some embodiments, pharmaceutical formulations comprising drug delivery vehicles described herein additionally incorporate a buffering agent. The buffering agent may be any pharmaceutically acceptable buffering agent. Buffer systems include, but are not limited to citrate buffers, acetate buffers, borate buffers, and phosphate buffers. Examples of buffers include, but are not limited to citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate, benzoic acid, and the like.

In some embodiments, pharmaceutical formulations comprising drug delivery vehicles described herein additionally incorporate a chelating agent. The chelating agent may be any pharmaceutically acceptable chelating agent. Chelating agents include, but are not limited to ethylene diaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid (e.g., citric acid monohydrate) and derivatives thereof. Derivatives of citric acid include anhydrous citric acid, trisodiumcitrate-dihydrate, and the like. Still other chelating agents include, but are not limited to, niacinamide and derivatives thereof and sodium deoxycholate and derivatives thereof.

In some embodiments, pharmaceutical formulations comprising drug delivery vehicles described herein additionally incorporate a bioactive agent and can contain an antioxidant. The antioxidant may be any pharmaceutically acceptable antioxidant. Antioxidants are well known to those of ordinary skill in the art and include, but are not limited to, materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, sodium sulfite and N-acetyl cysteine. In certain embodiments such materials, when present, are typically added in ranges from 0.01 to 2.0%.

In some embodiments, pharmaceutical formulations comprising drug delivery vehicles described herein are formulated with a cryoprotectant. The cryoprotecting agent may be any pharmaceutically acceptable cryoprotecting agent. Common cryoprotecting agents include, but are not limited to, histidine, polyethylene glycol, polyvinyl pyrrolidine, lactose, sucrose, mannitol, polyols, and the like.

In some embodiments, pharmaceutical formulations comprising drug delivery vehicles described herein are formulated with an isotonic agent. The isotonic agent can be any pharmaceutically acceptable isotonic agent. This term is used in the art interchangeably with iso-osmotic agent, and is known as a compound that is added to the pharmaceutical preparation to increase the osmotic pressure, e.g., in some embodiments to that of 0.9% sodium chloride solution, which is iso-osmotic with human extracellular fluids, such as plasma. Illustrative isotonicity agents include, but are not limited to, sodium chloride, mannitol, sorbitol, lactose, dextrose and glycerol.

In certain embodiments pharmaceutical formulations of the drug delivery vehicles may optionally comprise a preservative. Common preservatives include, but are not limited to, those selected from the group consisting of chlorobutanol, parabens, thimerosol, benzyl alcohol, and phenol. Suitable preservatives include but are not limited to: chlorobutanol (e.g., 0.3-0.9% w/v), parabens (e.g., 0.01-5.0%), thimerosal (e.g., 0.004-0.2%), benzyl alcohol (e.g., 0.5-5%), phenol (e.g., 0.1-1.0%), and the like.

In some embodiments, pharmaceutical formulations comprising drug delivery vehicles are formulated with a humectant, e.g., to provide a pleasant mouth-feel in oral applications. Humectants known in the art include, but are not limited to, cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration and Therapy

The cargo (e.g., drug) loaded drug delivery vehicles can be administered to a subject (e.g., patient) by any of a variety of techniques.

In certain embodiments the pharmaceutical formulations are administered parenterally, e.g., intraarticularly, intravenously, intraperitoneally, subcutaneously, or intramuscularly. In some embodiments, the pharmaceutical compositions are administered intravenously, intraarteraly, or intraperitoneally by a bolus injection. Particular pharmaceutical formulations suitable for this administration are found in Remington's Pharmaceutical Sciences, Mack Publishing Company, Philadelphia, Pa., 17th ed. (1985). Typically, the formulations comprise a solution of the drug delivery vehicles suspended in an acceptable carrier, preferably an aqueous carrier. As noted above, suitable aqueous solutions include, but are not limited to physiologically compatible buffers such as Hanks solution, Ringer's solution, or physiological (e.g., 0.9% isotonic) saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc., e.g., as described above.

In other methods, the pharmaceutical formulations containing drug delivery vehicles described herein may be contacted with the target tissue by direct application of the preparation to the tissue. The application may be made by topical, "open" or "closed" procedures. By "topical" it is meant the direct application of the pharmaceutical preparation to a tissue exposed to the environment, such as the skin, oropharynx, external auditory canal, and the like. Open procedures are those procedures that include incising the skin of a patient and directly visualizing the underlying tissue to which the pharmaceutical formulations are applied. This is generally accomplished by a surgical procedure, such as a thoracotomy to access the lungs, abdominal laparotomy to access abdominal viscera, or other direct surgical approaches to the target tissue. Closed procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrizamide imaging of the spinal cord. Alternatively, the preparations may be administered through endoscopic devices. In certain embodiments the pharmaceutical formulations are introduced via a cannula.

In certain embodiments the pharmaceutical formulations comprising drug delivery vehicles described herein are administered via inhalation (e.g., as an aerosol). Inhalation can be a particularly effective delivery rout for administration to the lungs and/or to the brain. For administration by inhalation, the drug delivery vehicles are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In certain embodiments, the drug delivery vehicles described herein are formulated for oral administration. For oral administration, suitable formulations can be readily formulated by combining the drug delivery vehicle(s) with pharmaceutically acceptable carriers suitable for oral delivery well known in the art. Such carriers enable the active agent(s) described herein to be formulated as tablets, pills, dragees, caplets, lozenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethylcellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

In various embodiments the drug delivery vehicle(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45), amphiphilic materials such as Suppocire AP and polyglycolized glyceride, and the like). The base is selected and compounded for a desired melting/delivery profile.

The route of delivery of drug delivery vehicles can also affect their distribution in the body. Passive delivery of drug delivery vehicles involves the use of various routes of administration e.g., parenterally, although other effective administration forms, such as intraarticular injection, inhalant mists, orally active formulations, transdermal iontophoresis, or suppositories are also envisioned. Each route produces differences in localization of the drug delivery vehicles.

Because dosage regimens for pharmaceutical agents are well known to medical practitioners, the amount of the drug delivery vehicle formulations that is effective or therapeutic for the treatment of a disease or condition in mammals and particularly in humans will be apparent to those skilled in the art. The optimal quantity and spacing of individual dosages of the formulations herein will be determined by the nature and extent of the condition being treated, the form, route and site of administration, and the particular patient being treated, and such optima can be determined by conventional techniques. It will also be appreciated by one of skill in the art that the optimal course of treatment, e.g., the number of doses given per day for a defined number of days, can be ascertained by those skilled in the art using conventional course of treatment determination tests.

In certain embodiments the drug delivery vehicles and/or pharmaceutical formations thereof can be used therapeutically in animals (including man) in the treatment of various infectious diseases caused by, inter alia, bacteria, viruses, parasitic microorganisms, and the like including conditions that require: (1) repeated administrations, (2) the sustained delivery of the drug in its bioactive form, or (3) the decreased toxicity with suitable efficacy compared with the free drug in question. In various embodiments the drug delivery vehicles and/or pharmaceutical formations thereof are administered in a therapeutically effective dose. The term "therapeutically effective" as it pertains to the drug delivery vehicles described herein and formulations thereof means that a biologically active substance present or and/or in the drug delivery vehicle provided/released in a manner sufficient to achieve a particular medical effect for which the biologically active substance (therapeutic agent) is intended. Examples, without limitation of desirable medical effects that can be attained are chemotherapy, antibiotic therapy, and regulation of metabolism. Thus, for example, therapeutically effective dose for treating an infection can be a dose (and/or dosage regimen) sufficient to inhibit the growth and/or proliferation of a pathogen, and/or to kill a pathogen, and/or to mitigate one or more symptoms produced by the pathogen.

Exact dosages will vary depending upon such factors as the particular therapeutic agent and desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the drug delivery vehicle(s) can be approximately equal to that employed for the free drug. However as noted above, the drug delivery vehicles described herein can significantly reduce the toxicity of the drug(s) administered thereby and significantly increase a therapeutic window. Accordingly, in some cases dosages in excess of those prescribed for the free drug will be utilized.

In certain embodiments, the dose of encapsulated drug administered at a particular time point will be in the range from about 1 to about 1,000 $mg/m^2/day$, or to about 800 $mg/m^2/day$, or to about 600 $mg/m^2/day$, or to about 400 $mg/m^2/day$. For example, in certain embodiments a dosage (dosage regiment) is utilized that provides a range from about 1 to about 350 $mg/m^2/day$, 1 to about 300 $mg/m^2/day$, 1 to about 250 $mg/m^2/day$, 1 to about 200 $mg/m^2/day$, 1 to about 150 $mg/m^2/day$, 1 to about 100 $mg/m^2/day$, from about 5 to about 80 $mg/m^2/day$, from about 5 to about 70 $mg/m^2/day$, from about 5 to about 60 $mg/m^2/day$, from about 5 to about 50 $mg/m^2/day$, from about 5 to about 40 $mg/m^2/day$, from about 5 to about 20 $mg/m^2/day$, from about 10 to about 80 $mg/m^2/day$, from about 10 to about 70 $mg/m^2/day$, from about 10 to about 60 $mg/m^2/day$, from about 10 to about 50 $mg/m^2/day$, from about 10 to about 40 $mg/m^2/day$, from about 10 to about 20 $mg/m^2/day$, from about 20 to about 40 $mg/m^2/day$, from about 20 to about 50 $mg/m^2/day$, from about 20 to about 90 $mg/m^2/day$, from about 30 to about 80 $mg/m^2/day$, from about 40 to about 90 $mg/m^2/day$, from about 40 to about 100 mg/m²/day, from about 80 to about 150 mg/m²/day, from about 80 to about 140 mg/m²/day, from about 80 to about 135 mg/m²/day, from about 80 to about 130 mg/m²/day, from about 80 to about 120 mg/m²/day, from about 85 to about 140 mg/m²/day, from about 85 to about 135 mg/m²/day, from about 85 to about 135 mg/m²/day, from about 85 to about 130 mg/m²/day, or from about 85 to about 120 mg/m²/day. In certain embodiments the does administered at a particular time point may also be about 130 mg/m²/day, about 120 mg/m²/day, about 100 mg/m²/day, about 90 mg/m²/day, about 85 mg/m²/day, about 80 mg/m²/day, about 70 mg/m²/day, about 60 mg/m²/day, about 50 mg/m²/day, about 40 mg/m²/day, about 30 mg/m²/day, about 20 mg/m²/day, about 15 mg/m²/day, or about 10 mg/m²/day.

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician. Skilled artisans will be able to optimize effective local dosages without undue experimentation in view of the teaching provided herein.

Multiple doses (e.g., continuous or bolus) of the compositions as described herein may also be administered to individuals in need thereof of the course of hours, days, weeks, or months. For example, but not limited to, 1, 2, 3, 4, 5, or 6 times daily, every other day, every 10 days, weekly, monthly, twice weekly, three times a week, twice monthly, three times a month, four times a month, five times a month, every other month, every third month, every fourth month, etc.

Kits.

In certain embodiments, kits are containing the drug delivery vehicles described herein or pharmaceutical formulations thereof are provided. The kits typically comprise a container containing drug-loaded drug delivery carrier as described herein Additionally, in certain embodiments, the kits can include instructional materials disclosing means of use of the drug-loaded carrier, e.g., in the treatment of an infection caused by a pathogen.

In addition, the kits optionally include labeling and/or instructional materials providing directions (e.g., protocols) for the use of the drug delivery vehicles described herein, e.g., alone or in combination for the treatment of various diseases. Instructional materials can also include recommended dosages, description(s) of counterindications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

A Pathogen-Specific Cargo Delivery Platform Based on Mesoporous Silica Nanoparticles Making a drug delivery platform pathogen-specific poses several challenges. First, it is necessary to consider the "container" used to hold the payload that later is to be released specifically in the presence of the target pathogen. Here, we chose mesoporous silica nanoparticles (MSNs) as the carriers due to their large internal pore volume and surface area, tunable particle size, pore size, and morphology, and huge flexibility for chemical modifications.[9-13] Next, one needs to address how a gatekeeping mechanism can be designed and implemented on this carrier that can act as a cap on the cargo-loaded pores and releases the cargo selectively in response to a specific pathogen. In nature, one way that highly selective recognition of target pathogens is achieved is through antibody-antigen interactions, and indeed, MSN-antibody conjugates have been reported that were used for analyte detection,[14-17] theranostics/imaging,[17-22] or cell targeting.[23-28] However, these examples demonstrate a specific recognition of an antigen by the MSN-antibody conjugate, but the recognition event itself does not stimulate a signal or killing response, i.e., there is no antigen-responsive gatekeeping mechanism that would selectively control cargo release only in the presence of a specific antigen or pathogen.

A design that can be used to achieve a proactive response is one in which the antibody is bound to antigens immobilized on the surface of the MSNs, consequently acting as a "cap" that hinders the diffusion of cargo from the pores of the container. By subtle manipulation of the surface-bound antigen such that the affinity of the antibody binding to it is reduced, the antigen produced by the target pathogen can compete effectively for binding to the gatekeeper antibody, leading to displacement of the antibody, pore uncapping, and cargo release (see, e.g., FIGS. 1, and 2). For the triggering event to occur, a way to "tune" the rather strong noncovalent antibody-antigen interaction is required such that a competitive displacement of the antibody cap occurs even at low antigen concentrations, and at the same time there is minimal nonspecific cargo release due to "leakage" from the delivery platform.

Figure 1:
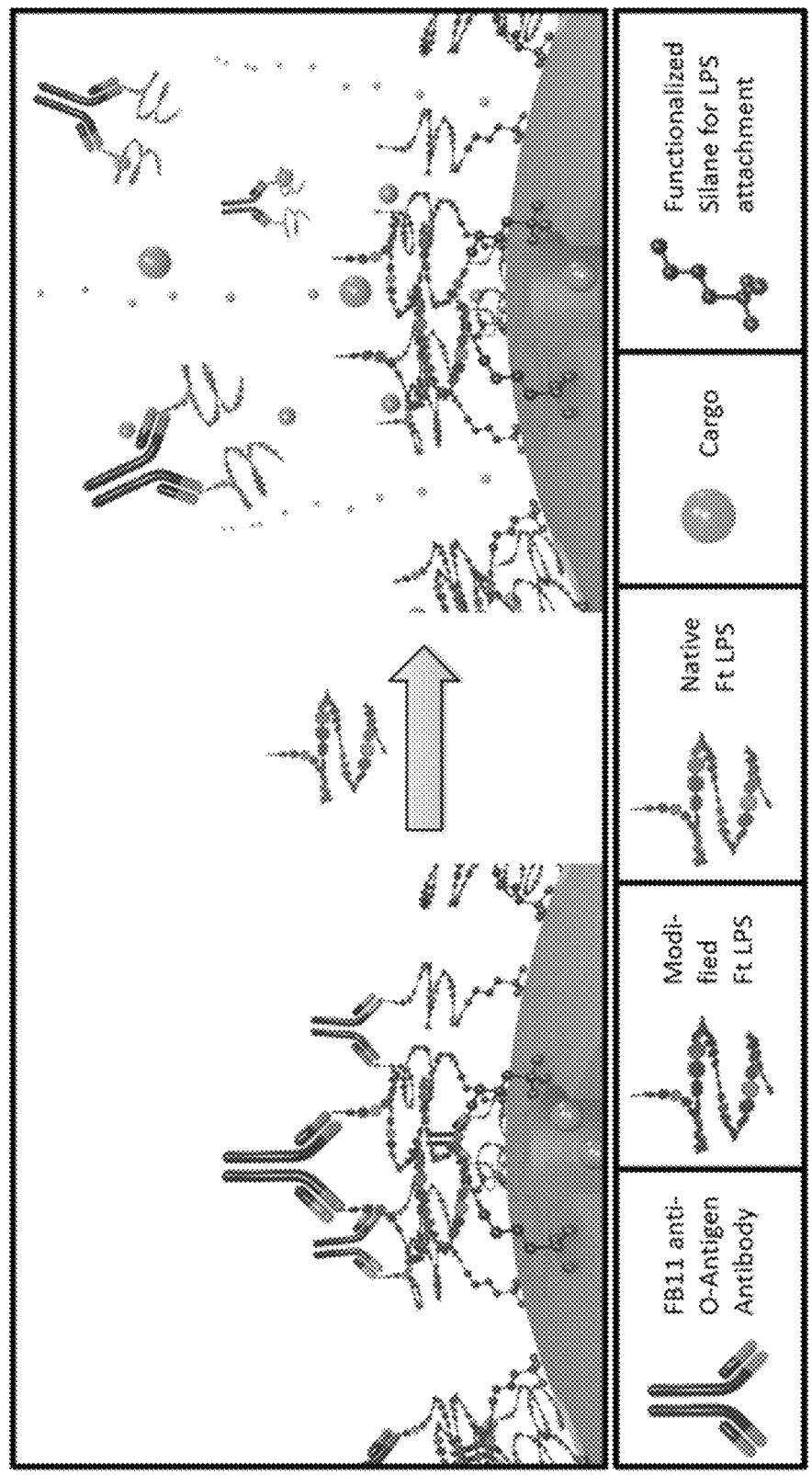
FIG. 1 shows a schematic representation of the triggered release of cargo (orange spheres) loaded into pores due to a competitive displacement of the antibody (green) that caps the pore by naturally occurring *Francisella tularensis* LPS (blue).
Figure 2:
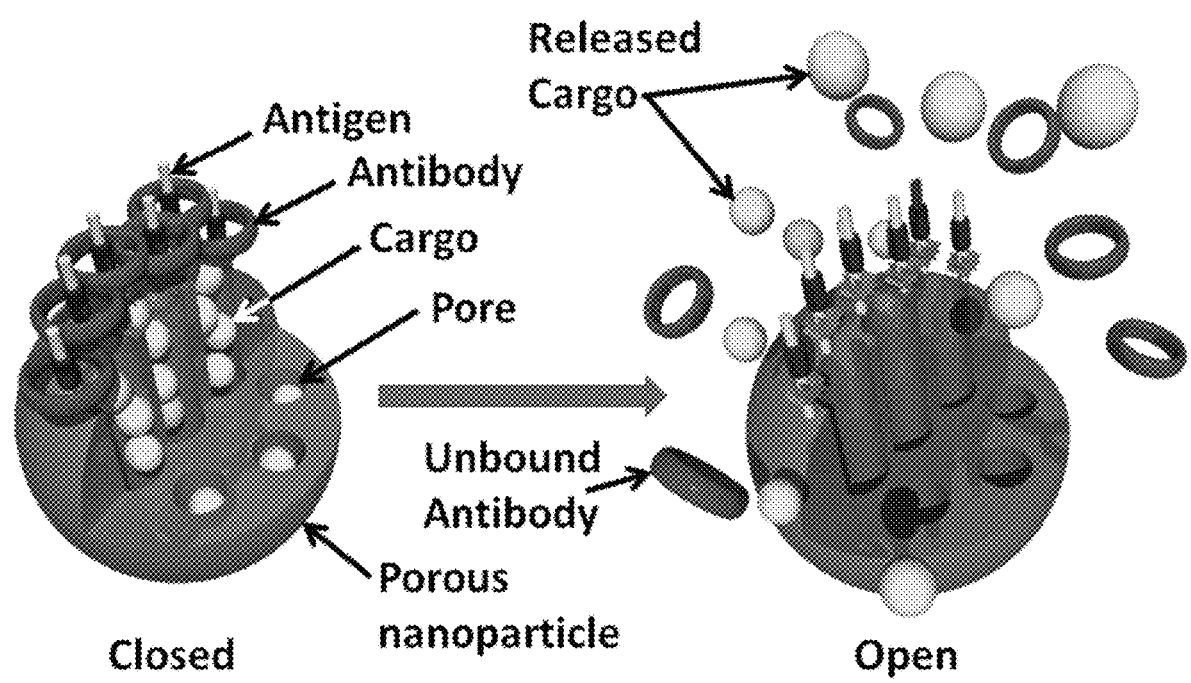
FIG. 2 schematically illustrates various design features of a delivery vehicle as described herein. As illustrated, the delivery vehicle can release a cargo in response to the presence of a specific antigen, e.g., in response to a pathogen bearing the antigen. In various illustrative, but non-limiting embodiments the cargo can either provide a signal (e.g. an optical change) and/or a threat eliminator (e.g. an antibiotic).

For our platform, we used the interaction of the FB11 antibody with a derivative of the O-antigen of Ft (*Francisella tularensis*) LPS immobilized on the nanoparticle surface for selective, pathogen-induced cargo release in our gated nanoparticle design. In the presence of the O-antigen that is naturally produced and shed by Ft (FIG. 7), a competitive displacement of the antibody cap takes place, which leads to pore uncapping and cargo release (FIG. 1).

Experimental

Unfunctionalized MSNs were synthesized according to a published procedure.[32] Functionalization was done by refluxing the unfunctionalized nanoparticles with the respective trialkoxysilane in dry toluene under an inert atmosphere of dry nitrogen overnight. The CTAB template was extracted from the pores using two extraction steps with ethanolic ammonium nitrate and in some cases ethanolic HCl solutions. The O-antigen was coupled to amine-functionalized MSNs through 1-ethyl-3-(3-dimethylaminopropyl)carbodiimide/N-hydroxy-succinimide (EDC/NHS) amidation or to 3-isocyanatopropyl triethoxysilane (ICPTES)-functionalized MSNs in dry dimethylsulfoxide (DMSO) in the presence of Zr(acac).[4] In some cases, the O-antigen attached to the MSNs was acetylated with acetic anhydride in dry pyridine in the presence of catalytic amounts of 4-(dimethylamino)-pyridin (DMAP). Cargo was loaded into the MSNs by soaking the samples in an aqueous solution of the cargo on a shaker overnight. Antibody capping was done by incubating the samples in the presence of FB11 anti-O-antigen antibody and BSA in PBS buffer.

The wzy gene, which codes for O-antigen polymerase, was deleted from *F. tularensis* live vaccine strain (LVS) by the method of allelic exchange as described.[33]

LPS and purification of the O-antigen tetrasaccharide was done employing a modification of the methods of Vinogradov et al.[34]

Detailed experimental procedures and further details on the employed materials and characterization methods can be found in the Supplemental Materials provided below.

Results and Discussion

It has been shown that the FB11 antibody recognizes a specific tetrasaccharide sequence at the end of the O-antigen polysaccharide chain of the Ft-LPS.[35] In our first attempts at pathogen-specific cargo release, we followed a protocol from Vinogradov et al. to hydrolytically cleave purified LPS from *Francisella tularensis* live vaccine strain (Ft-LVS-LPS) and extracted the immunoreactive tetrasaccharide units.[34] However, the hydrolysis of the LPS always led to a decrease in immunogenicity, and triggered release of a model drug was not observed after attaching the tetrasaccharides to the nanoparticles by coupling one of the free OH groups to glycidoxypropyl or isocyanatopropyl groups on the silica surface, capping with FB11 antibody, and adding pristine Ft-LVS-LPS. We also tried longer O-antigen fragments consisting of 2-3 and >5 tetrasaccharide units (obtained from a partial hydrolysis of the LPS), but again, triggered release was not observed.

Figure 4:
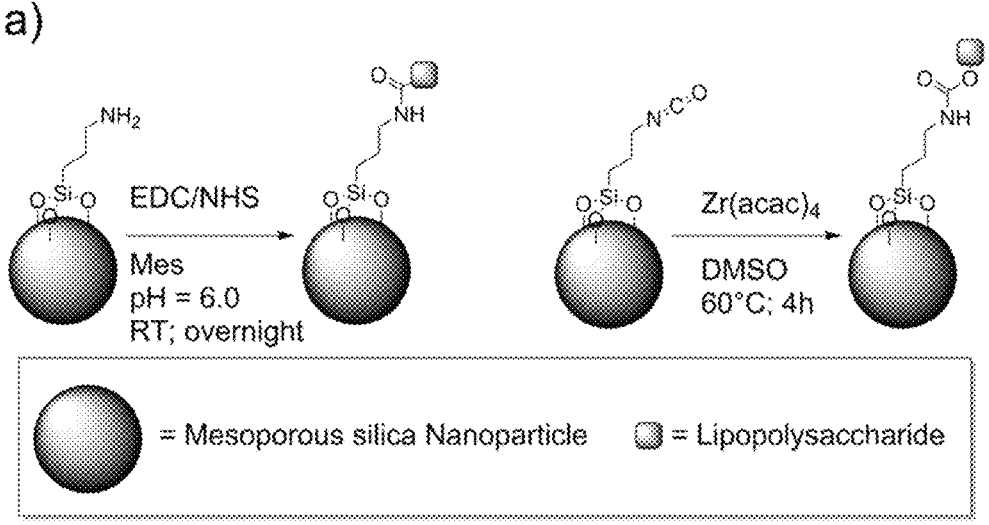
FIG. 4. Panel a) Chemical attachment strategies to bind Ft-LVS-LPS to the surface of MSNs. Panel b) Phase contrast (upper part of each panel) and fluorescence (lower part of each panel) microscopy images recorded at fixed exposure and gain settings after Texas Red conjugated GAM immunostaining. (A) Isocyanato-functionalized MSNs with covalently bound LPS that were also incubated with FB11 antibody. (B) Amine-functionalized MSNs with covalently bound LPS that were also incubated with FB11 antibody. (C) Isocyanato-functionalized MSNs with covalently bound LPS, but without FB11 antibody. (D) Amine-functionalized MSNs with covalently bound LPS, but without FB11 antibody. (E) Isocyanato-functionalized MSNs without LPS, incubated with FB11 antibody. (F) Amine-functionalized MSNs without LPS, incubated with FB11 antibody. (G) Isocyanato-functionalized MSNs without LPS and without FB11 antibody. (H) Amine-functionalized MSNs without LPS and without FB11 antibody. The magnification is identical for all images (scale bar: 10 µm).
Figure 4:
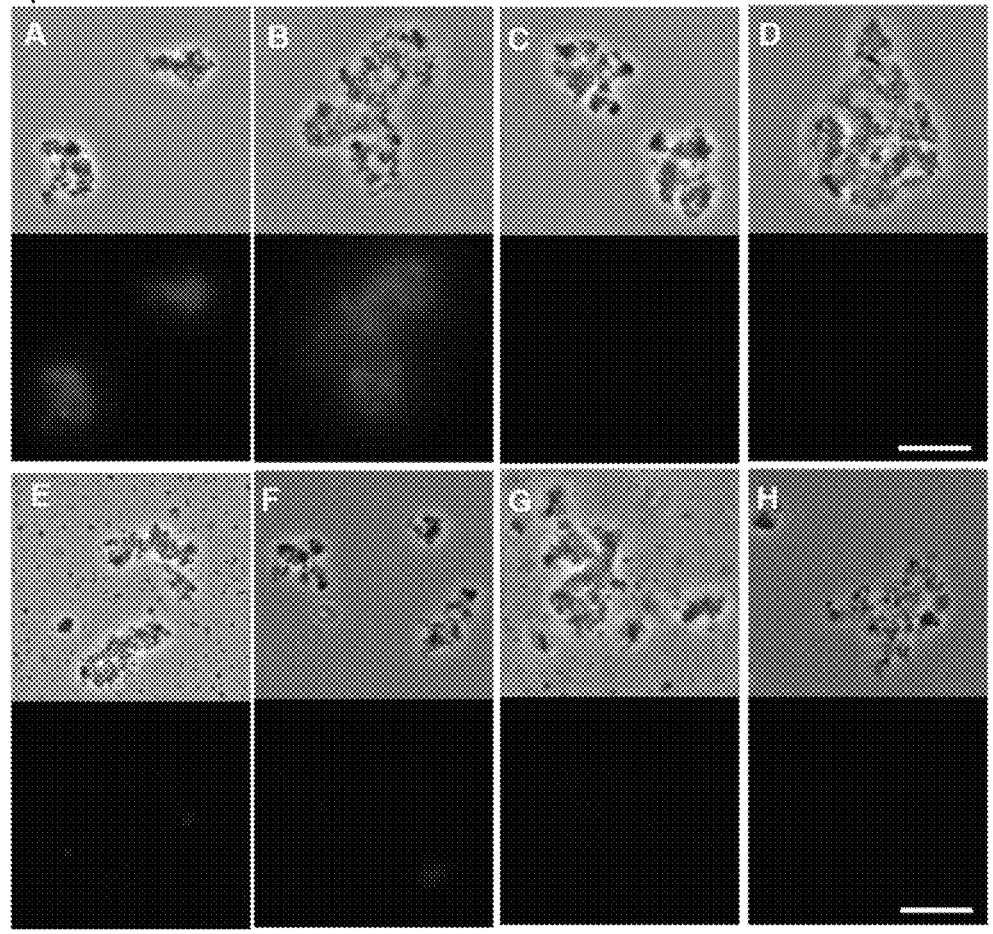

As we assumed that the loss of immunogenicity of the O-antigen tetrasaccharide that occurred in the hydrolysis steps (and presumably also in the attachment of the antigen to the nanoparticle surface) interfered with successful antibody capping, we next tried coupling the unmodified, unhydrolyzed Ft-LVS-LPS to the nanoparticles. Two different attachment strategies were developed: one involved binding of the carboxylic acid group of a Kdo sugar (3-deoxy-D-manno-oct-2-ulosonic acid) in the core region of the Ft-LVS-LPS to aminopropyl-functionalized MSNs through an EDC/NHS amidation reaction; the other strategy again used the attachment of sugar OH groups to isocyanatopropyl-functionalized MSNs in the presence of a Lewis acid (zirconium(IV) acetylacetonate) in a dipolar-aprotic, anhydrous solvent (DMSO) (FIG. 4, panel a). To confirm successful attachment of the Ft-LVS-LPS to the surface of the nanoparticles and to ensure that the immunogenicity and antibody-binding capability of the Ft-LVS-LPS were retained during the coupling reactions, we used an immunostaining assay to detect the presence of the FB11 antibody that was binding the antigen on the nanoparticle surface (FIG. 4, panel b). Several control experiments were also carried out to make sure that both the antigen and antibody were bound to the MSNs. No immunostaining was observed when either the O-antigen attachment step, the FB11 binding step, or both were omitted, proving that there is no nonspecific binding of the FB11 antibody to the unfunctionalized MSN surface and also no nonspecific binding of the fluorescent secondary goat-anti-mouse (GAM) immunostaining antibody to the unfunctionalized MSN surface or the Ft-LVS-LPS. From these data, we concluded that both Ft-LVS-LPS antigen attachment and FB11 antibody binding to surface-bound Ft-LVS-LPS were successful.

Figure 8:
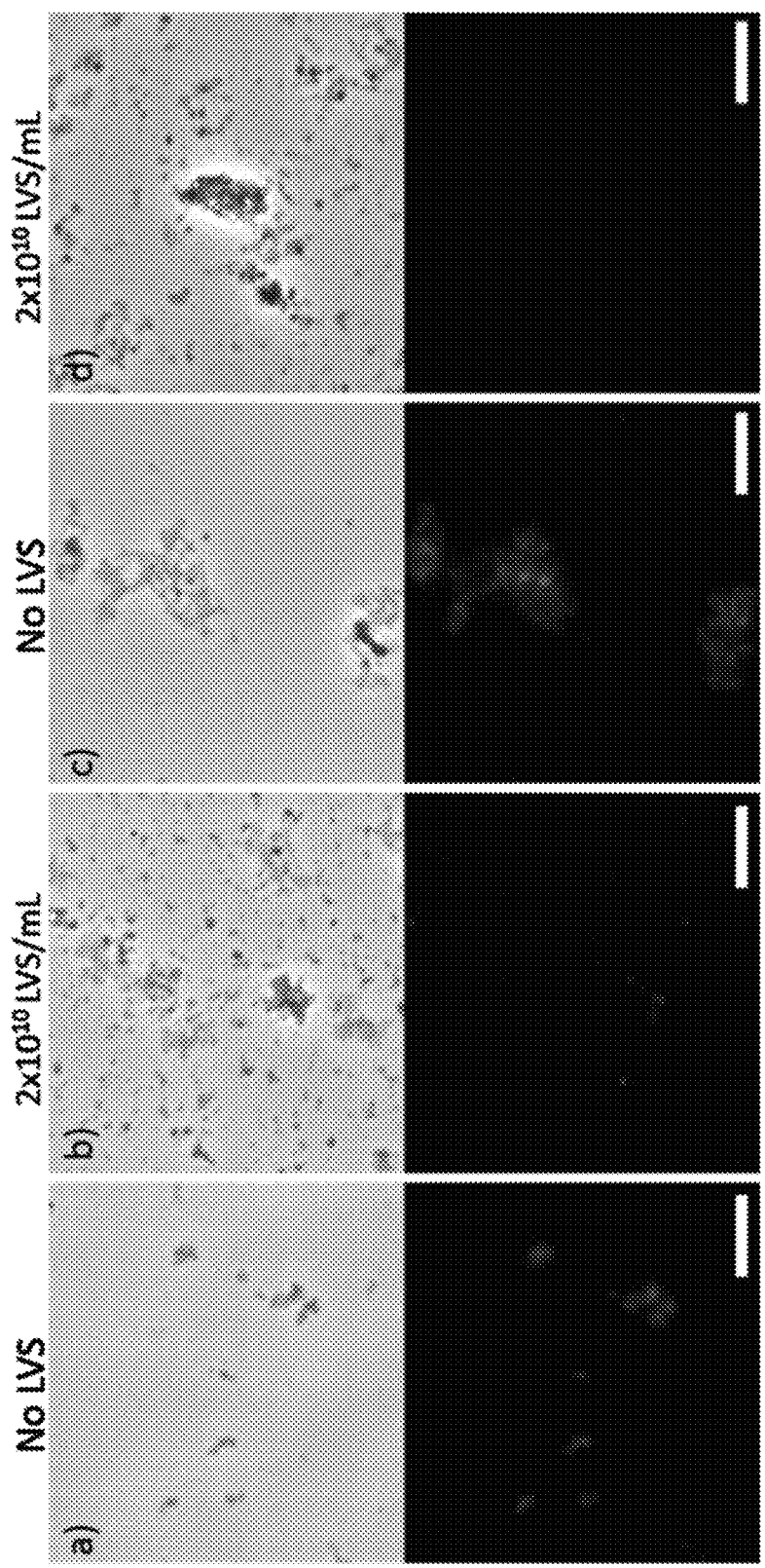
FIG. 8. Panel a) Immunostaining of unloaded, ICPTES-functionalized, Ft-LVS-LPS coated and FB11 antibody-capped MSN incubated in TSBC for 5 h at room temperature (no bacteria, control sample). Panel b) Immunostaining of the same particles as in a), incubated for 5 h at room temperature in TSBC with $2 \times 10^{10}$ live *Francisella tularensis* Live Vaccine Strain bacteria. Panel c) Immunostaining of unloaded, APTES-functionalized, Ft-LVS-LPS coated and FB11 antibody-capped MSN incubated in TSBC for 5 h at room temperature (no bacteria, control sample). Panel d) Immunostaining of the same particles as in c), incubated for 5 h at room temperature in TSBC with $2 \times 10^{10}$ live *Francisella tularensis* Live Vaccine Strain bacteria. Top: brightfield-images. Bottom: Red fluorescence from Texas Red conjugated GAM secondary staining antibodies. The presence of strong red fluorescence in panels a) and c) indicates the successful attachment of Ft-LVS-LPS, while the absence of red fluorescence in panels b) and d) indicates the successful displacement of FB11 antibodies from the MSN surface in the presence of *Francisella tularensis* Live Vaccine Strain bacteria in vitro. Fixed exposure and gain settings were used for the fluorescence images. Scale bars are 5 µm.
Figure 9:
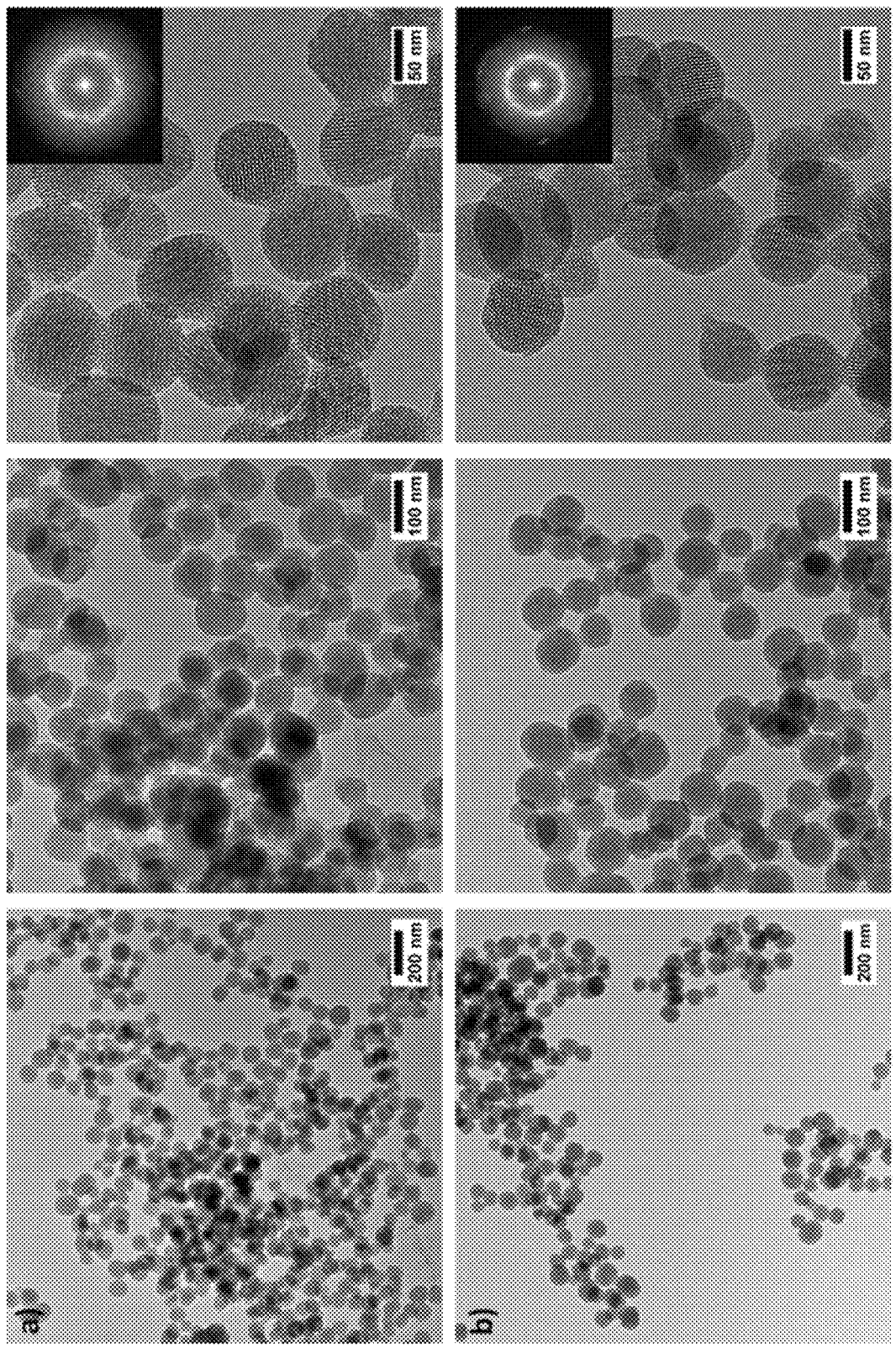
FIG. 9. TEM images of APTES-functionalized MSN panel a) before and panel b) after acetylation, showing that the particle morphology and pore structure are unaffected by the treatment. Insets are FFT images of the right micrographs, demonstrating that the ordered porous structure is preserved after acetylation.
Figure 10:
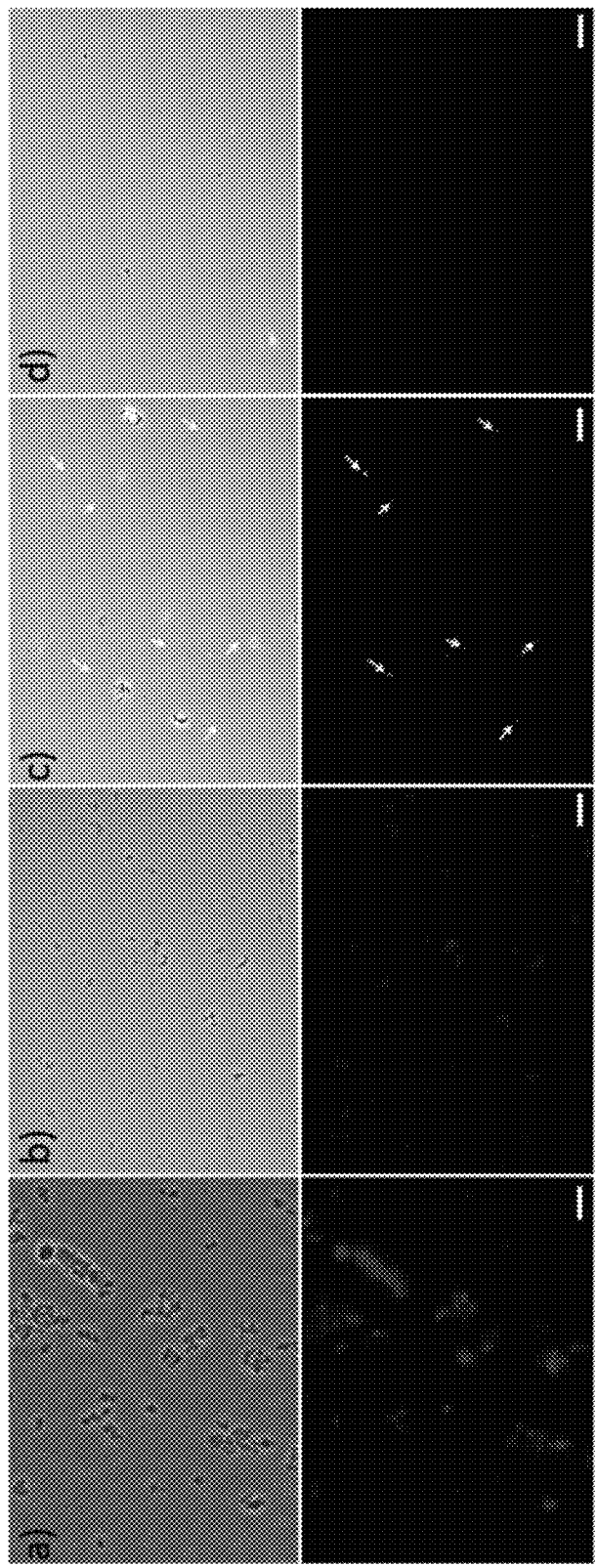
FIG. 10. Panel a) Immunostaining of unloaded, ICPTES-functionalized, Ft-LVS-LPS coated, acetylated and FB11 antibody-capped MSNs incubated in PBS for 5 h at room temperature without Ft-LVS-LPS (control sample). Panel b)

Next, we focused on determining if a competitive displacement of the FB11 antibodies could be triggered in the presence of Ft-LVS-LPS. For this and all future experiments, we decided to use the LPS attachment via the Kdo residue to amine-functionalized MSNs through amide-bond formation (even though our immunostaining experiments indicated that both attachment strategies worked equally well), since this attachment is experimentally easier and the location of the attachment site is better defined than the random attachment that occurs via one of the OH groups to isocyanato-functionalized MSNs. Also, an attachment to a sugar in the core region should not interfere with antibody-antigen binding, while the attachment of the antigen by one of the OH groups of the terminal tetrasaccharide might do so under certain circumstances. We prepared MSNs that were functionalized with Ft-LVS-LPS, capped with FB11 antibodies, and then incubated with either 109 live Ft-LVS bacteria or with PBS as a control. Subsequent immunostaining with GAM antibodies did not show a significant reduction in fluorescence of the sample incubated with Ft-LVS bacteria as compared with the control sample. Since the LPS on the MSN surface is identical to the LPS produced by the bacteria, the driving force for a competitive displacement of the antibody appeared to be too low under these conditions. As a proof-of-principle, we repeated the experiment with a 20 times higher Ft-LVS concentration and for a longer time, and indeed we could see a reduction of fluorescence after GAM immunostaining (FIG. 8). These results indicated that the operation of the nanovalve is feasible and that the valve can in principle work at high bacterial (and hence LPS) concentrations in vitro. Next, we focused on strategies to reduce the affinity of the FB11 antibody to the LPS on the MSN surface in order to facilitate the displacement of the antibody at lower Ft bacterial concentrations, which may be more relevant to early stages of an infection. We expected that a covalent modification of the sugars in the O-antigen would lower the binding affinity of the antibody to the O-antigen. More specifically, we anticipated that acetylating the OH groups could lead to a lower binding affinity due to a steric mismatch, a polarity mismatch, and also due to the fact that the acetylated OH groups cannot act as hydrogen-bonding donors to the Fab regions of the FB11 antibody any more (they can still act as hydrogen-bonding acceptors to some extent). Moreover, the acetylation is experimentally rather simple, inexpensive, and the MSNs can withstand the reaction conditions of the acetylation, as confirmed by transmission electron microscopy (TEM) analysis (FIG. 9). This approach also has the advantage that the acetylation can be performed after the coupling of the LPS to the MSNs, making workup easier and keeping open the option of attaching the LPS via one of its OH groups, e.g., to isocyanato-functionalized MSNs. Indeed, immunostaining results indicated that FB11 antibodies bound to acetylated LPS on the MSN surface could be displaced after incubation with Ft-LVS-LPS at a concentration of 5 mg/mL (FIG. 10). In later experiments, we found that even lower concentrations were sufficient (for example, 1.25 mg/mL as demonstrated in FIG. 6, panel b).

Next, we sought to determine if we can use this system to encapsulate cargo molecules and specifically release them in the presence of Ft-LVS-LPS. We prepared a sample in which we attached Ft-LVS-LPS to amine-functionalized MSNs through an amide bond, acetylated the bound LPS, loaded the particles with fluorescein as a model drug and fluorescent indicator, capped the pores with FB11 antibodies, incubated them with Ft-LVS-LPS to trigger the competitive displacement, and measured the amount of released fluorescein. However, despite the fact that earlier immunostaining experiments had shown that LPS attachment and FB11 binding both occur and that a competitive displacement of FB11 from acetylated LPS on the MSN surface can be achieved, the difference between fluorophore release from the sample that was incubated with Ft-LVS-LPS and the control sample was not very pronounced. After several optimization steps, we achieved an approximately 35% greater amount of fluorescein release after 3 h of incubation with Ft-LVS-LPS (2.5 mg/mL) compared with a control sample in which no Ft-LVS-LPS was present (FIG. 11).

Figure 6:
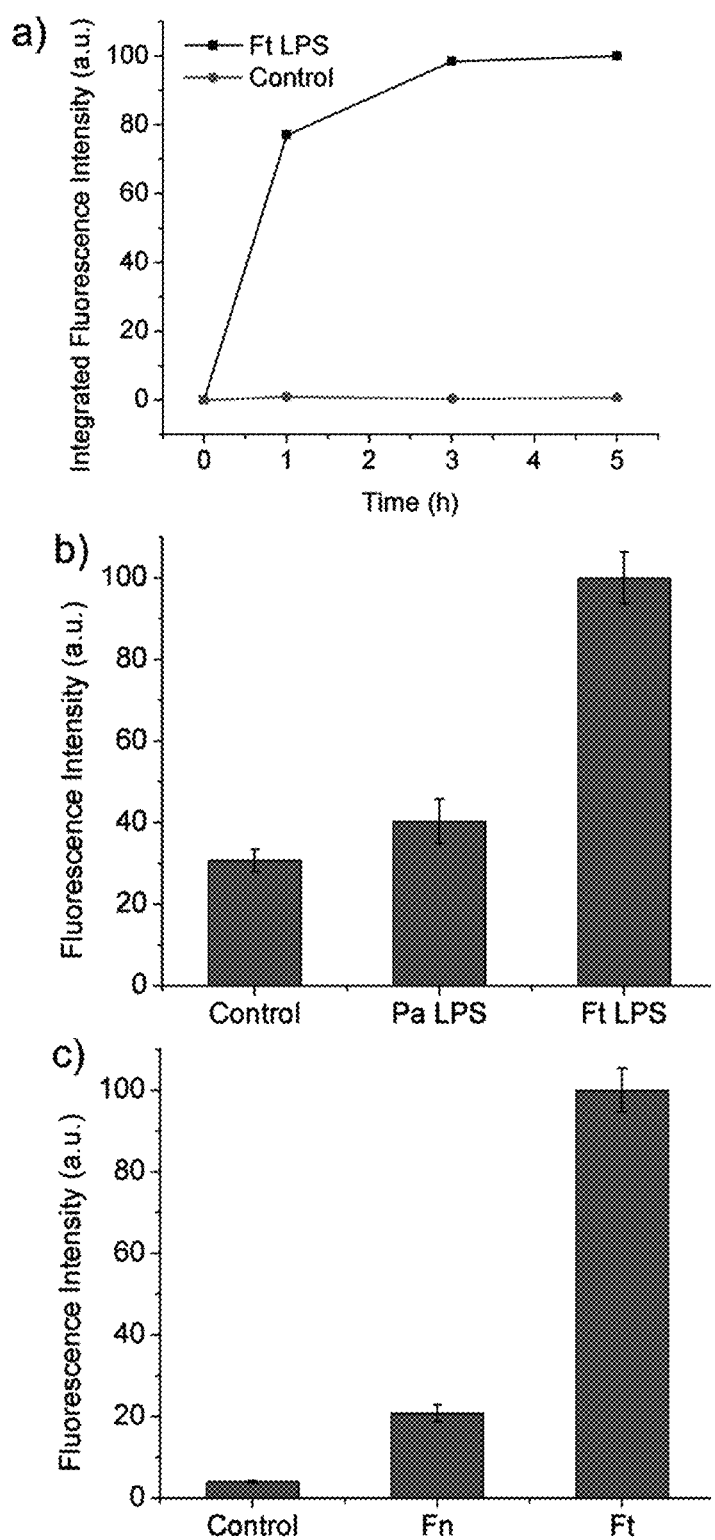
FIG. 6. Panel a) Time-based release of a model drug (Hoechst 33342) in the presence (black squares) and absence (red dots) of purified Ft-LVS-LPS (1.25 mg/mL). Panel b) Nuclear staining intensity after release of a model drug (Hoechst 33342) triggered by incubation of MSNs with 1.0 mg/mL purified LPS from *Pseudomonas aeruginosa* (Pa LPS), 1.0 mg/mL *Francisella tularensis* (Ft LPS), and a control sample containing only PBS buffer for 1 h at 37° C. Panel c) Fluorescence intensity after release of a model drug (Hoechst 33342) in vitro triggered by incubation of MSNs with live *Francisella novocida* bacteria (Fn), live *Francisella tularensis* bacteria (Ft), and a control sample containing only PBS for 1 h at 37° C.

Our next goal was to achieve a better release performance, i.e., a larger difference between the amount of cargo released in the presence and absence of Ft-LVS-LPS. In the previous release experiments, we had seen that there was also fluorescein release from the control sample. We assumed that this "leakiness" was due to the fact that the antibody was too far away from the nanoparticle surface and the pore openings to provide effective capping and hence a sufficient enough barrier to diffusion of guest molecules from the pores of the MSNs into the solution. In the naturally occurring Ft-LVS-LPS, the O-antigen unit typically consists of many tetrasaccharide repeating units, which gives rise to a large distance between the core region (where the Kdo sugar and hence the attachment site to the nanoparticles is located) and the terminal tetrasaccharide at the end of the O-antigen chain (where the binding site for the FB11 antibody is located). To bring both sites closer together, we decided to use LPS from a Ft wzy deletion mutant (FIG. 12). This mutant lacks a gene that encodes an enzyme that polymerizes the O-antigen chain, i.e., the LPS of these mutants consists of the lipid A part, the core region, and only one tetrameric unit of the O-antigen. We obtained the single tetrasaccharide-containing LPS after introducing the wzy mutation into *F. tularensis* LVS, growing the bacteria, extracting and purifying their LPS, and carefully hydrolyzing off the lipid A part. The product was characterized by matrix-assisted laser desorption ionization time-of-flight mass spectrometry (MALDI-TOF Miss.), and a structure consistent with that previously described in the literature for Ft-LVS-LPS was obtained (FIGS. 5 and 13).[36] The suggested structure ([M]+Na+, m/zcalcd=1888.6563, m/zfound=1888.6198) differs from the published structure by the fact that a galactosamine in the core region is acetylated and that the Kdo sugar underwent β-elimination and was reduced, which can be explained by the acidic hydrolysis and the reductive workup, respectively. The peaks at m/z=1910.6321 and m/z=1726.6368 correspond to the exchange of H+ for Na+ ($\Delta m/z_{calcd}$=21.9820) and the loss of a hexose sugar ($\Delta m/z_{calcd}$=162.0528) from the suggested structure, respectively. The m/z values and isotope pattern of the main peak are in excellent agreement with the structure suggested in FIG. 5. After confirming the structure and purity of the sample, we used our previously developed and optimized approach to bind the LPS from the wzy deletion mutant to amine-functionalized MSNs, acetylated the bound LPS, loaded the MSNs with fluorescein as a model drug, capped the pores with FB11 antibody, and performed another release experiment in which we added natural LPS from the parental nonmutated Ft-LVS bacteria (FIG. 6, panel a). We observed a strong increase in fluorescein release after Ft-LVS-LPS addition indicating that (a) leakiness was markedly reduced by use of the shorter LPS produced by the wzy deletion mutant; (b) cargo was efficiently retained inside the porous MSNs by means of the antibody nanovalve; and (c) the MSNs released their cargo upon a specific stimulus, i.e., Ft-LPS. We also checked the selectivity of the nanovalve by comparing the release of a model drug in the presence of Ft-LVS-LPS vs a different LPS from *Pseudomonas aeruginosa* (Pa) in which the O-antigen chain (as with Ft) also contains modified galactosamines and quinovosamines. As expected from the highly specific nature of the antibody-antigen interaction, a significant increase in cargo release was observed only in the presence of Ft-LVS-LPS, and not in the presence of Pa-LPS (see FIG. 6, panel b). After these successful preliminary results with the cargo delivery platform, we further tested the specificity of cargo release using the live bacteria by comparing release by Ft with that of the very closely related bacterium *Francisella novocida* (Fn; for a comparison of the very similar O-antigen structures, see FIG. 14). Indeed, a highly selective release of the model drug was observed, as MSNs incubated with Ft but not with Fn or medium showed pronounced release (see FIG. 6, panel c). These results demonstrate the feasibility and the high selectivity of this drug delivery platform in vitro.

The FB11 antibody is well suited for capping of the MSN pores because it recognizes the terminal tetrasaccharide of the LPS O-antigen, i.e., the antigen which is most peripheral and therefore most surface exposed, and its displacement is not complicated by steric hindrance. On the other hand, steric hindrance would likely be a factor limiting the use of antibodies that recognize internal O-antigen sugars. Because the FB11 antibody recognizes the terminal sugars, both bacteria-bound LPS and free LPS should be able to displace the antibody from the surface of the MSN. Gram-negative bacteria are well-known to shed LPS during normal growth,[37,38] and we have found that this phenomenon holds true for *F. tularensis*, with shedding of 0.2% and 0.6% of their LPS growing on agar plates or broth culture, respectively (FIG. 7). We have also observed abundant shedding of LPS by *F. tularensis* following phagocytosis by macrophages and the presence of LPS in vesicular compartments separate from *F. tularensis* bacilli. Direct interaction between the MSNs and the bacteria is not required for the MSNs to kill the bacteria. Indeed, in our previous studies of MSNs that release antibiotics after uptake by macrophages, we have demonstrated that the MSN-delivered antibiotics kill intracellular bacteria despite the MSN and the bacteria being located in different intracellular compartments of the macrophage.[39-41] Antibiotics released from the MSNs are able to diffuse into the adjacent medium or the host cell cytosol and kill the bacteria even without direct contact between the MSNs and the bacteria.

Conclusion.

As discussed in this example, it is a challenge to design and make a nanomaterial that can selectively and autonomously respond to a specific molecule or organism and signal its presence. In the area of human safety, such a nanomaterial may be useful for detection of toxic substances including poisons, environmental pollutants, man-made chemical warfare agents, and pathogens. The latter, the subject of this example, can include disease-causing bacteria in general and Ft as a specific biowarfare or bioterrorism threat.

We presented design considerations and a synthetic approach that allow for highly selective, pathogen-specific triggered cargo release from MSNs with possible applications for the detection and treatment of a target pathogen. We found that the use of LPS from a wzy deletion mutant significantly reduced leakage, presumably because it brings the antibody cap closer to the pore openings. The competitive displacement of the antibody caps was made more feasible by acetylating the O-antigen bound to the nanoparticles without interfering with the structural integrity of the MSNs. We presented the use of a fluorescent dye cargo that provided the signaling event. The use of antibiotics as cargo to kill the bacteria is under current investigation in our laboratories. Since the specificity and triggered release is based on the interaction between antibody and the O-antigen chain of the LPS, we believe that the same principles can also be applied to a variety of other Gram-negative bacteria, providing a new platform for pathogen-responsive cargo delivery for the detection and treatment of infectious diseases.

References for Example 1

1) Saslaw et al. (1961) Arch. Intern. Med. 107: 702.
2) Chocarro, A.; Gonzalez, A.; Garcia, I. Clin. Infect. Dis. 2000, 31, 623.
3) Feldman et al. (2001) N. Engl. J Med. 345: 1601.
4) Harris (1992) Ann. N.Y. Acad. Sci. 666: 21.
5) Christopher et al. (1997) JAMA, 278: 412.
6) Alibek & Handelman, Biohazard: The Chilling True Story of the Largest Covert Biological Weapons Program in the World—Told from the Inside by the Man Who Ran It, Reprint; Delta: New York, 2000.
7) Li, Z.; Clemens, D. L.; Lee, B.-Y.; Dillon, B. J.; Horwitz, M. A.; Zink, J. I. ACS Nano 2015, 9, 10778.
8) Lee, B.-Y.; Li, Z.; Clemens, D. L.; Dillon, B. J.; Hwang, A. A.; Zink, J. I.; Horwitz, M. A. Small 2016, 12, 3690.
9) Rühle, B.; Saint-Cricq, P.; Zink, J. I. Chem Phys Chem 2016, 17, 1769.
10) Ambrogio, M. W.; Thomas, C. R.; Zhao, Y.-L.; Zink, J. I.; Stoddart, J. F. Acc. Chem. Res. 2011, 44, 903.
11) Tarn, D.; Ashley, C. E.; Xue, M.; Carnes, E. C.; Zink, J. I.; Brinker, C. J. Acc. Chem. Res. 2013, 46, 792.
12) Argyo, C.; Weiss, V.; Brauchle, C.; Bein, T. Chem. Mater. 2014, 26, 435.
13) Li, Z.; Barnes, J. C.; Bosoy, A.; Stoddart, J. F.; Zink, J. I. Chem. Soc. Rev. 2012, 41, 2590.
14) Tao, L.; Zhang, C.; Zhang, J.; Sun, Y.; Li, X.; Yan, K.; Jin, B.; Zhang, Z.; Yang, K. Microchim. Acta 2016, 183, 2163.
15) Ma, H.; Wang, Y.; Wu, D.; Zhang, Y.; Gao, J.; Ren, X.; Du, B.; Wei, Q. Sci. Rep. 2016, 6, 19797.
16) Eum, J. Y.; Hwang, S. Y.; Ju, Y.; Shim, J. M.; Piao, Y.; Lee, J.; Kim, H.-S.; Kim, J. Chem. Commun. 2014, 50, 3546.
17) Erathodiyil, N.; Ying, J. Y. Acc. Chem. Res. 2011, 44, 925.
18) Chiu, H.-Y.; Deng, W.; Engelke, H.; Helma, J.; Leonhardt, H.; Bein, T. Sci. Rep. 2016, 6, 25019.
19) Knežević, N..; Durand, J.-O. Nanoscale 2015, 7, 2199.
20) Chen, F.; Nayak, T. R.; Goel, S.; Valdovinos, H. F.; Hong, H.; Theuer, C. P.; Barnhart, T. E.; Cai, W. Mol. Pharmaceutics 2014, 11, 4007.
21) Milgroom, A.; Intrator, M.; Madhavan, K.; Mazzaro, L.; Shandas, R.; Liu, B.; Park, D. Colloids Surf., B 2014, 116, 652.
22) Lei, C.; Liu, P.; Chen, B.; Mao, Y.; Engelmann, H.; Shin, Y.; Jaffar, J.; Hellstrom, I.; Liu, J.; Hellstrom, K. E. J. Am. Chem. Soc. 2010, 132, 6906.
23) Gao, Y.; Gu, S.; Zhang, Y.; Xie, X.; Yu, T.; Lu, Y.; Zhu, Y.; Chen, W.; Zhang, H.; Dong, H.; Sinko, P. J.; Jia, L. Small 2016, 12, 2595.
24) Zhang, Y.; Guo, J.; Zhang, X.-L.; Li, D.-P.; Zhang, T.-T.; Gao, F.-F.; Liu, N.-F.; Sheng, X.-G. Int. J. Pharm. 2015, 496, 1026.
25) Zhang, H.; Ding, Q.; Ding, J. RSC Adv. 2016, 6, 5049.
26) Ngamcherdtrakul, W.; Morry, J.; Gu, S.; Castro, D. J.; Goodyear, S. M.; Sangvanich, T.; Reda, M. M.; Lee, R.; Mihelic, S. A.; Beckman, B. L.; Hu, Z.; Gray, J. W.; Yantasee, W. Adv. Funct. Mater. 2015, 25, 2646.
27) Chen, F.; Hong, H.; Shi, S.; Goel, S.; Valdovinos, H. F.; Hernandez, R.; Theuer, C. P.; Barnhart, T. E.; Cai, W. Sci. Rep. 2015, 4, 5080.
28) Tsai, C.-P.; Chen, C.-Y.; Hung, Y.; Chang, F.-H.; Mou, C.-Y. J. Mater. Chem. 2009, 19, 5737.
29) Climent, E.; Bernardos, A.; Martinez-Mañez, R.; Maquieira, A.; Marcos, M. D.; Pastor-Navarro, N.; Puchades, R.; Sancenón, F.; Soto, J.; Amorós, P. J. Am. Chem. Soc. 2009, 131, 14075.
30) Climent, E.; Martinez-Mañez, R.; Maquieira, Á.; Sanceno n, F.; Marcos, M. D.; Brun, E. M.; Soto, J.; Amoros, P. Chemistry Open 2012, 1, 251.
31) Climent, E.; Gröninger, D.; Hecht, M.; Walter, M. A.; Martinez-Mañez, R.; Weller, M. G.; Sancenon, F.; Amoros, P.; Rurack, K. Chem. Eur. J. 2013, 19, 4117.
32) Rühle, B.; Datz, S.; Argyo, C.; Bein, T.; Zink, J. I. Chem. Commun. 2016, 52, 1843.
33) Clemens, D. L.; Lee, B.-Y.; Horwitz, M. A. Infect. Immun. 2012, 80, 952.
34) Vinogradov, E. V.; Shashkov, A. S.; Knirel, Y. A.; Kochetkov, N. K.; Tochtamysheva, N. V.; Averin, S. F.; Goncharova, O. V.; Khlebnikov, V. S. Carbohydr. Res. 1991, 214, 289.
35) Roche, M. I.; Lu, Z.; Hui, J. H.; Sharon, J. Hybridoma 2011, 30, 19.
36) Gunn, J. S.; Ernst, R. K. Ann. N.Y. Acad. Sci. 2007, 1105, 202.
37) Cadieux, J. E.; Kuzio, J.; Milazzo, F. H.; Kropinski, A. M. J. Bacteriol. 1983, 155, 817.
38) Mattsby-Baltzer, I.; Lindgren, K.; Lindholm, B.; Edebo, L. Infect. Immun. 1991, 59, 689.
39) Li, Z.; Clemens, D. L.; Lee, B.-Y.; Dillon, B. J.; Horwitz, M. A.; Zink, J. I. ACS Nano 2015, 9, 10778.
40) Hwang, A. A.; Lee, B.-Y.; Clemens, D. L.; Dillon, B. J.; Zink, J. I.; Horwitz, M. A. Small 2015, 11, 5066.
41) Clemens, D. L.; Lee, B.-Y.; Xue, M.; Thomas, C. R.; Meng, H.; Ferris, D.; Nel, A. E.; Zink, J. I.; Horwitz, M. A. Antimicrob. Agents Chemother. 2012, 56, 2535.

Supplemental Materials

Methods and Characterization

Matrix-Assisted Lased Desorption Ionization—Time of Flight Mass Spectrometry

Matrix-assisted lased desorption ionization—time of flight mass spectrometry (MALDI—TOF-MS) was performed using an Applied Biosystems Voyager-DE STR mass spectrometer equipped with a 337-nm nitrogen laser producing 3-ns pulses at repetition rate to 20 Hz in reflector mode, an acceleration voltage of 25000 V, a grid voltage of 76%, a delay time of 400 ns, and a laser intensity of 1876. Appropriate dilutions of the analyte were prepared by mixing a 2,5-dihydroxybenzoic acid (DHB) solution (10 mg/mL in acetonitrile) containing 1% trifluoroacetic acid (TFA) with the analyte dissolved in water and drying the mixture at room temperature. For calibration, a 1:1 (v/v) mixture of the above matrix solution and an external standard containing a mixture of Met-Arg-Phe-Ala (10 µM), Angiotensin I & II (10 µM), Substance P (10 µM), Neurotensin (10 µM), ACTH (18-39) (10 µM), and bovine insulin (50 µM) in water was used.

Fluorescence Spectra

Fluorescence spectra were recorded on an Acton Spectra Pro 2300i CCD cooled below −120° C. with liquid nitrogen. A CUBE 445-40C laser (Coherent Inc., Santa Clara, Calif., USA) was used at a wavelength of 448 nm and a power of 2 mW for Fluorescein excitation and a CUBE 375-16C laser (Coherent Inc., Santa Clara, Calif., USA) was used at a wavelength of 376 nm and a power of 2 mW for Hoechst 33342 excitation. A 400 nm and a 475 nm long pass filter were used to block scattered and stray light. Spectral data were obtained by averaging 60 spectra with an exposure time of 1 s.

Transmission Electron Microscopy

Transmission electron microscopy (TEM) images were recorded on a Tecnai T12 Quick CryoEM and CryoET (FEI) at an accelerating voltage of 120 kV. A suspension (8 μL) of nanoparticles in ethanol (MSNs) was dropped on a 200 mesh carbon coated copper grid and the solvent was allowed to evaporate at room temperature.

Nitrogen Adsorption and Desorption

Nitrogen adsorption and desorption isotherms were obtained at 77 K using an Autosorb-iQ (Quantachrome Instruments). Sample outgassing was performed for 12 hours at 493 K. Pore size distribution and pore volume were calculated by a NLDFT equilibrium model of $N_2$ on silica, based on the adsorption branch of the isotherms. BET surface area was calculated over the range of partial pressure between ~0.08-0.23 $p/p_0$. The mesopore volume was determined from NLDFT calculations for pores smaller than 6.5 nm in diameter.

Zeta-Potential Analysis and Dynamic Light Scattering

Zeta-potential analysis and dynamic light scattering (DLS) were carried out on a ZetaSizer Nano (Malvern Instruments Ltd., Worcestershire, U.K.) in DI water.

Experimental Section

Chemicals:

Tetraethylorthosilicate (TEOS; 99%, Aldrich), cetyltrimethylammonium bromide (CTAB; 98%, Aldrich), sodium hydroxide solution (1.000 M, Aldrich), 3-aminopropyl triethoxysilane (APTES; 99%, Aldrich), 3-isocyanatopropyl triethoxysilane (ICPTES; 95%, Aldrich), ammonium nitrate, Zirconium(IV) acetylacetonate ($Zr(acac)_4$; 99%, Strem Chemicals), EDC.HCl (99%, Covachem), sulfo-NHS (99%, Covachem), 4-(Dimethylamino)-pyridin (DMAP; 99%, Aldrich), lipopolysaccharide from *Francisella tularensis* live vaccine strain (Ft-LVS-LPS; BEI Resources), monoclonal mouse Anti-*Francisella tularensis* LPS antibody [FB11] (FB11 antibody; Abcam (ab2033) or GeneTex (GTX22033)), anhydrous dimethylsulfoxide (DMSO; 99%, Aldrich), absolute ethanol (EtOH; Aldrich), Hoechst 33342 (2-(4-Ethoxyphenyl)-5-(4-methyl-1-piperazinyl)-2,5'-bi-1H-benzimidazole trihydrochloride; 98%, Aldrich) and Fluorescein disodium salt (90%, Aldrich) were used as received.

Anhydrous toluene was obtained by distillation from $CaH_2$ under dry nitrogen.

Moisture-sensitive reactions were carried out under an inert atmosphere of dry nitrogen.

Bacteria:

*F. tularensis* subsp. *holarctica* Live Vaccine Strain (LVS) was obtained from the Centers for Disease Control and Prevention (Atlanta, Ga.). *F. novicida* strain U112 was obtained from Karl Klose, University of Texas San Antonio, San Antonio, Tex. Bacteria were passaged, stored, and grown at 37° C. on chocolate agar plates enriched with IsoVitale X and hemoglobin (CA plates) as described previously (see, e.g., Clemens et al. (2004) *Infect. Immun.* 72: 3204.; Clemens et al. (2005) *Infect. Immun.* 73: 5892). Bacteria scraped from plates were used to inoculate Trypticase Soy Broth supplemented with 0.1% cysteine (TSBC) and 0.025% ferric pyrophosphate at 37° C., shaking at 200 rpm prior to obtaining cultures for use in the experiments.

Deletion of the Wzy Gene from *F. tularensis* Live Vaccine Strain (LVS).

The wzy gene, which codes for O-antigen polymerase, was deleted from *F. tularensis* LVS by the method of allelic exchange as described (see, e.g., Clemens et al. (2012) *Infect. Immun.* 80: 952). In brief, an intermediate plasmid was constructed by PCR amplification of 1-kilobase chromosomal regions upstream and downstream of the wzy gene from LVS genomic DNA and ligated with SalI digested pSMP-ΔwbtDEF to replace the DNA fragment containing the wbtDEF gene exchange cassette. Subsequently, a chloramphenicol resistance gene was cloned into the BsrGI site engineered in between the two arms of the chromosomal region flanking wzy on the intermediate plasmid to generate the final plasmid construct pSMP-Δwzy. The conjugation procedure was carried out with LVS and *Escherichia coli* S17-1 carrying pSMP-Δwzy. The conjugation mixture was plated on chocolate agar containing 2.5 μg/mL chloramphenicol (for selection of LVS mutants with pSMP-Δwzy incorporated into the chromosome via homologous recombination) and 100 μg/mL polymyxin B (for counter selection of *E. coli* as LVS is resistant). Because SacB converts sucrose into the toxic product levan, LVS transconjugates were counter selected on chocolate agar containing 2.5 μg/mL chloramphenicol and 5% sucrose to facilitate a second homologous recombination event. The resulting strain, LVSΔwzy removed the conjugation plasmid from its chromosome while retaining the chloramphenicol resistance gene, which replaced the wzy gene. For complementation, LVSΔwzy was transformed by electroporation of a pMP607 construct carrying the wzy gene of LVS driven by the promoter of *Francisella* outer membrane protein gene, FTN_1451. Parental and O-antigen deficient strains of LVS harvested from chocolate agar with and without proteinase K treatment were boiled in SDS sample buffer and run on a 4-15% gradient polyacrylamide gel for immunoblotting analysis. The blot was first probed with anti-*F. tularensis* LPS monoclonal antibody FB11, and after stripping, probed with anti-*F. tularensis* IglC polyclonal antibody.

LPS and Purification of the O-Antigen Tetrasaccharide

*Pseudomonas aeruginosa* LPS was purchased from Sigma Chemical Company (St. Louis, Mo.). Wild-type *F. tularensis* LPS was obtained from Biodefense & Emerging Infections Research Resources Repository (BEI Resources). *F. tularensis* LVS Δwzy was grown in TSBC and 0.025% ferric pyrophosphate at 37° C., shaking at 200 rpm, to an absorbance at 540 nm of 1-1.5. We employed a modification of the methods of Vinogradov et al. (1991) *Carbohydr. Res.* 214: 289, for purification of *F. tularensis* LVS Δwzy O-antigen tetrasaccharide. The bacteria were pelleted in pre-weighed centrifuge tubes by centrifugation at 5000 rcf for 30 min and washed twice with PBS. The bacterial pellets were weighed after the second wash and extracted with a freshly prepared solution of hot (68° C.) 50% phenol (5 mL of phenol per gram of bacterial pellet). The sample was sonicated with a probe tip sonicator for 5 minutes to disrupt clumps (50% duty cycle, output setting 5, Model W-375, Heat Systems Ultrasonics, Inc., Plainview, N.Y.). The sample was heated at 68° C. while stirring with a magnetic stirrer for an additional 2 hours and transferred to 4° C. and stirred overnight. Cell debris and phenol were removed by centrifugation at 2000 rcf for 60 min at 4° C. The top aqueous phase was removed, dialyzed against distilled water for two days at 4° C. with three changes of the dialysate, and dried by lyophilization. The dried powder was resuspended in 10 mM Tris HCl, pH 7.6, 2 mM $MgCl_2$, sonicated to disperse clumps, and digested with DNAse (30 U/mL) and RNAse (25 µg/mL) for 4 hours at 37° C. Pronase (0.2 mg/mL) was added and the sample was incubated at 37° C. for an additional 2 h. The sample was applied to a Q-sepharose column and eluted with a 0-0.3 M NaCl gradient. Fractions from the column were evaluated for LPS by ELISA using FB11 antibody. Aliquots of 1 µL of each of the fractions was diluted 100-fold with 50 mM $NaHCO_3$, pH 9.6, and added to wells of a 96-well high binding ELISA plate and incubated for 3 h at room temperature. Wells were blocked with 1% BSA in PBS for 90 min, washed three times with PBS, incubated with 1:2000 FB11 antibody for 90 min, washed three times with PBS, and incubated with 1:2000 goat-anti-mouse IgG polyperoxidase conjugate (Bio-Rad) for 90 min at room temperature. Wells were washed three times with 50 mM Tris-HCl, pH 7.6, 0.85% NaCl (TBS); developed by addition of TBS peroxidase substrate (BioRad), freshly prepared according to the manufacturer's directions; and read in an ELISA plate reader. Fractions with significant LPS immunoreactivity were pooled and concentrated with a 10,000 MWCO (Millipore) centrifugal concentrator. (The LPS forms micelles because of its lipid A and is retained above the filter.) The sample was subjected to mild acid hydrolysis by heating in 1% acetic acid for 2.5 hours at 100° C.[4] The sample was centrifuged to remove insoluble lipid A, adjusted to neutral pH by the addition of 2 M ammonium hydroxide, and reduced by addition of $NaBH_4$ (10 mg/mL) with stirring at room temperature for 2 h. The sample was concentrated with a 3000 MWCO filter and applied to a Toyopearl HW-40S gel filtration column (100-7000 Da MW range) and eluted with water. Fractions from the gel filtration column were evaluated for O-antigen immunoreactive material by a competition ELISA. (Note: a direct ELISA is not possible because the lipid A has been removed and the fractions do not bind directly to ELISA wells.) Wells of a 96-well high binding ELISA plate were coated for 3 h at RT with a 1 µg/mL solution of wild-type *F. tularensis* LPS (BEI Resources) in 50 mM $NaHCO_3$, pH 9.6. Wells were blocked with 1% BSA in PBS and washed with PBS. Aliquots of fractions from the gel filtration column (diluted in PBS with 1% BSA) or standard amounts of *F. tularensis* LPS (0-2.5 µg/mL in PBS with 1% BSA), were mixed with 1:1000 FB11 antibody in the same buffer, incubated overnight at 4° C., and added to the washed ELISA wells that had been pre-coated with LPS. After 90 min at RT, the wells were washed with PBS; incubated with 1:2000 goat anti-mouse polyperoxidase conjugate in 1% BSA in PBS; washed three times with TBS; developed with BioRad TBS Peroxidase Substrate according to the manufacturer's directions; and optical densities of the wells read with an ELISA plate reader. Fractions with O-antigen reactivity (i.e. fractions with low absorbance readings on the ELISA plate) were pooled, dried under vacuum in pre-weighed tubes using a Savant SpeedVac Centrifuge Concentrator (Thermo Scientific), and weighed to determine the amount of the dried O-antigen tetrasaccharide powder per tube.

Nanoparticle Synthesis

1.) Synthesis of Unfunctionalized MSN.

Unfunctionalized mesoporous silica nanoparticles were synthesized according to a published procedure (see, e.g., Rühle et al. (2016) *Chem. Commun.* 52: 1843). In brief, 200 mg of CTAB and 1200 µL of sodium hydroxide solution (1.000 M) were dissolved in 100 mL of water under stirring. The solution was heated at 80° C. for 30 minutes, followed by the addition of 1050 µL of TEOS under vigorous stirring. Stirring was continued for 2 h at 80° C., and the solution was allowed to cool to room temperature. The nanoparticles were collected by centrifugation (10 min at 7197 rcf), washed 2× with water (2×90 mL), 2× with ethanol (2×90 mL) and 2× with toluene (2×90 mL), redispersed in 20 mL of dry toluene and directly used for further functionalization.

2.) MSN Functionalization

The unfunctionalized mesoporous silica nanoparticles in 20 mL of dry toluene were stirred in a flame-dried 50 mL round bottom flask under nitrogen. Then, 55 µL of APTES or ICPTES (corresponding to ~5 mol % of the originally used amount of TEOS) were added, and the resulting mixture was heated to reflux overnight. The nanoparticles were collected by centrifugation (10 min at 7197), washed 2× with toluene (2×90 mL) and stored in toluene for further functionalization.

3.) Extraction of APTES-Functionalized MSN (MSN-$NH_2$)

APTES-functionalized MSN dispersed in toluene were washed 2× with ethanol (2×90 mL). To extract the organic template from the pores, the nanoparticles were dispersed in 90 mL of an ethanolic ammonium nitrate solution (1 mg/50 mL), refluxed for 1 h, collected by centrifugation (10 min at 7197 rcf), washed 1× with ethanol (90 mL), redispersed in 90 mL of an acidic ethanolic solution (EtOH:HCl(conc.) =90/10 (v/v)), refluxed again for 1 h, collected by centrifugation (10 min at 7197 rcf), washed 2× with ethanol (2×90 mL) and stored in ethanol.

4.) O-Antigen Coupling to APTES-Functionalized MSN 6 mg of APTES-functionalized MSN dispersed in ethanol were washed 2× with $H_2O$ (2×1.5 mL), 1× with 1.5 mL Mes buffer (100 mM, pH=6.0), and redispersed in 1.5 mL Mes buffer (100 mM, pH=6.0). 5 mg of EDC.HCl, 2.5 mg of sulfo-NHS, and 0.6 mg (10 wt %) of Ft-LVS-LPS or Δwzy-O-antigen were added, and the mixture was incubated for 3 h at room temperature. Then the sample was washed 2× with $H_2O$ (2×1.5 mL) to remove any unreacted components and stored in $H_2O$.

5.) Acetylation of O-Antigen-Conjugated MSN

In some cases (see main text), the O-antigen attached to the MSN was acetylated to tune the antibody-antigen interaction and achieve a better competitive displacement at low Ft-LVS-LPS concentrations. For the acetylation, 6 mg of O-antigen-conjugated MSN were washed 2× with anhydrous pyridine (2×1.5 mL), redispersed in a mixture of 500 µL of dry pyridine, 500 µL of acetic anhydride and a catalytic amount of DMAP, and incubated for 1 h at room temperature. Then, the supernatant was removed, the particles were washed 2× with methanol (2×1.5 mL) to quench unreacted acetic anhydride and 2× with $H_2O$ and then stored in $H_2O$.

6.) Cargo Loading of APTES-Functionalized MSN

In some cases (see main text), the MSN were loaded with Fluorescein or Hoechst 33342 by soaking the samples in an aqueous dye solution on a shaker overnight.

7.) Antibody Capping of APTES-Functionalized MSN

Unloaded particles (6 mg) were dispersed directly in 400 µL of PBS (1×; pH=7.4) containing 0.1 wt % BSA and incubated for 2 h at room temperature to block unspecific antibody adsorption sites. Then, FB11 antibody (0.05-0.09 mg corresponding to 0.8-1.5 wt %) was added to the solution. After incubation for 2 h at room temperature, the samples were washed 2× with PBS (1×, pH=7.4) and stored in PBS (1×, pH=7.4). Corresponding control samples for the immunostaining assay were obtained by the same procedure, but the O-antigen attachment step, the FB11 capping step, or both were omitted.

If the samples were loaded with a dye, 6 mg of the loaded samples were centrifuged, 640 µL of the supernatant were discarded, the particles were redispersed in the remaining 360 µL of the dye loading solution, 40 µL of PBS (10×; pH=7.4) containing 1 wt % BSA were added (resulting in a slightly diluted dye loading solution in 400 µL of PBS (1×; pH=7.4) containing 0.1 wt % BSA), and the resulting solution was incubated for 2 h at room temperature. Then, FB11 antibody (0.05-0.09 mg corresponding to 0.8-1.5 wt %) was added to the solution. After incubation for 2 h at room temperature, the samples were washed 5× with PBS (1×, pH=7.4) and stored in PBS (1×, pH=7.4). In some cases, the dye-loaded particles were centrifuged, all the supernatant was removed, and the samples were redispersed in 400 µL of fresh PBS (1×; pH=7.4) containing 0.1 wt % BSA. Then, FB11 antibody (0.05-0.09 mg corresponding to 0.8-1.5 wt %) was added directly to this solution without prior incubation with BSA alone. After incubation for 2 h at room temperature, the samples were washed 5× with PBS (1×, pH=7.4) and stored in PBS (1×, pH=7.4). We observed that this procedure leads to less unspecific dye adsorption and release on the MSN surface. However, the loading might be slightly less due to leakage of the dye from the MSN during the capping step (to minimize this effect, BSA blocking and FB11 capping were done in the same step and not sequentially in this case).

8.) O-Antigen Coupling to ICPTES-Functionalized MSN 6 mg of ICPTES-functionalized MSN dispersed in toluene were washed 3× with anhydrous DMSO (3×1.5 mL) and redispersed in 500 µL of dry DMSO. 0.15 mg of $Zr(acac)_4$ and 0.4 mg of Ft-LVS-LPS were added and the solution was stirred for 3 days at 80° C. and then washed 1× with DMSO to remove unreacted Ft-LVS-LPS and Zr(acac) (see, e.g., Vinogradov et al. (1991) Carbohydr. Res. 214: 289).

9.) Extraction of ICPTES-Functionalized MSN

Here, the extraction was done after attachment of the O-antigen to avoid ethanolysis/hydrolysis of the isocyanato groups. After the O-Antigen attachment step, 6 mg of MSNs dispersed in DMSO were washed 2× with ethanol (2×1.5 mL). To extract the organic template from the pores, the nanoparticles were dispersed in 3 mL of an ethanolic ammonium nitrate solution (1 mg/50 mL), heated at 65° C. for 1.5 h, collected by centrifugation (5 min at 16873 rcf), washed 2× with ethanol (2×3 mL), and 2× with water (2×3 mL)

10.) Antibody Capping of ICPTES-Functionalized MSN

The extracted ICPTES-functionalized MSN (6 mg) were washed 1× with PBS (1×, pH=7.4) and then incubated for 2 h in 400 µL of a PBS buffer (1×, pH=7.4) containing 0.1 wt % BSA to block unspecific attachment sites. Then, 25 µL of the FB11 antibody (2 mg/mL in PBS) were added to the solution. After incubation for 2 h at room temperature, the samples were washed 2× with PBS (1×, pH=7.4) and stored in PBS (1×, pH=7.4) for the immunostaining assay. Corresponding control samples were obtained by the same procedure, but the O-antigen attachment step, the FB11 capping step, or both were omitted.

Immunostaining Assays

The immunostaining results from FIG. 4, panel b that demonstrate O-antigen and FB11 attachment were obtained by blocking the corresponding unloaded samples with or without Ft-LVS-LPS and/or FB11 antibody functionalization (synthesized as described above and explained in the main text) with 1% BSA in PBS, incubating with 1:400 Texas Red-X conjugated Goat-anti-Mouse IgG; washing with PBS; and acquiring images with an Eclipse TE2000-S fluorescence microscope equipped with an X-Cite 120 light source (Nikon), and SPOT RT-KE monochrome camera and SPOT software (Diagnostic Instruments, Sterling Heights, Mich.) using fixed exposure and gain settings (35 msec, Gain 2).

The immunostaining results shown in FIG. 8 that demonstrate successful FB11 antibody displacement at high bacterial concentrations in vitro were obtained by incubating 0.2 mg of unloaded, Ft-LVS-LPS-coated and FB11 antibody-capped MSN (synthesized as described above) in TSBC and in TSBC with $2\times10^{10}$ LVS for 5 hours at 37° C., washing 3 times with PBS containing 1% Triton X-100 (to lyse the bacteria), incubating the washed MSN with Texas Red-X conjugated Goat-anti-Mouse IgG 1:200 dilution in PBS-BSA with 0.1% Triton X-100, washing the treated MSN with PBS containing 0.1% Triton X-100, and acquiring images with a fluorescence microscope, as described above, using fixed exposure and gain settings (50 msec, Gain 16).

The immunostaining results shown in FIG. 9 that demonstrate successful FB11 antibody displacement with Ft-LVS-LPS after O-Antigen acetylation were obtained by adding 0.1 mL of unloaded, ICPTES-functionalized (2 mg/mL in PBS) or APTES functionalized (~0.5 mg/mL in PBS), Ft-LVS-LPS-coated and FB11 antibody-capped MSN (synthesized as described above) to 0.1 mL of 5 mg/mL Ft-LVS-LPS in water ("LPS treated") or 0.1 mL of water ("no LPS") and incubated for 5 hours at 37° C., rotating at 250 rpm. 0.1 mL of the same samples but without any FB11 antibody capping was added to 0.1 mL of water as controls. MSNs were pelleted by centrifugation at 10000 rcf for 5 min; the supernatants discarded; and the pellets immediately resuspended in 0.5 mL of PBS with 0.1% Triton X-100. The MSNs were pelleted again by centrifugation (5 min at 10000 rcf); supernatants discarded; and the pellets resuspended in 0.5 mL of PBS with 1% BSA. MSNs were incubated in this for 30 minutes prior to pelleting as before; resuspended in 0.2 mL of PBS-1% BSA containing 1:200 Texas Red-X-conjugated goat anti-mouse IgG; and incubated for 90 minutes at room temperature. MSNs were washed by pelleting by centrifugation as before; the supernatants discarded; and the MSN resuspended in 0.5 mL of PBS containing 0.1% Triton X-100. The MSNs were pelleted again as before; resuspended in 0.2 mL of PBS with 0.1% Triton X-100; and phase contrast and fluorescence images acquired with fixed exposure and gain settings.

Cuvette Release Experiments

For the release experiments shown in FIG. 6, panel a and FIG. 11, 2 samples of each 1 mg dye-loaded, FB11 antibody-capped MSNs were suspended in (200−x) µL of PBS (1×; pH=7.4) with x=12.5 in FIG. 6, panel a and x=50 in FIG. 10. Then, x µL of Ft-LVS-LPS (20 mg/mL in water) were added to one sample (resulting in 1.25 mg/mL Ft-LVS-LPS in FIG. 6, panel a and 5.0 mg/mL Ft-LVS-LPS in FIG. 10), and the same amount of water was added to the other sample as a control. Both samples were then incubated at 37° C., 50 µL aliquots were taken after 1 h, 3 h, and 5 h, diluted into 1450 µL of PBS (10×, pH=7.4), and the fluorescence of the supernatant was analyzed. 60 emission scans (409.13 nm-688.30 nm) were recorded, the intensity around the emission maximum was integrated (500-550 nm for Fluorescein and 480-520 nm for Hoechst 33342), averaged over all 60 scans, and the results were plotted against time.

In Vitro Release by *Pseudomonas aeruginosa* LPS Vs. *Francisella tularensis* LPS Human monocytic cell line, THP-1 (ATCC TIB-202), was grown in RPMI-1640 supplemented with 2 mM glutamine, 10% heat-inactivated fetal bovine serum, penicillin (100 IU) and streptomycin (100 μg/mL). Prior to use, the THP-1 cells were spun down by centrifugation at 200 g for 10 min at room temperature; re-suspended in RPMI-1640 supplemented with 2 mM glutamine, 10% heat-inactivated fetal bovine serum and 100 nM phorbol 12-myristate 13-acetate (PMA); and seeded in 96-well glass bottom microplates (Matrical) at a density of $10^5$ cells/200 μl/well for 3 days at 37° C., 5% $CO_2$-95% air atmosphere. Monolayers were fixed with 4% paraformaldehyde (Electron Microscopy Grade, Polysciences) in Phosphate Buffered Saline (PBS, Gibco, Life Sciences Technology) for 30 minutes at room temperature, permeabilized for 30 min with 0.1% Tween-20 in PBS, and washed with PBS.

MSNs (0.1 mg) were pelleted by centrifugation at 14,000 rcf for 90 seconds. Then, the particles were resuspended in PBS, PBS containing 0.1 mg/mL *Pseudomonas aeruginosa* LPS, or PBS containing 0.1 mg/mL LVS LPS, and incubated for 3 h at 37° C. After the incubation, the particles were pelleted by centrifugation at 14000 rcf for 4 min; the supernatants added to formaldehyde-fixed, Tween-20 permeabilized THP-1 cells, described above; and the cells incubated for 30 min at RT. After washing 2× with PBS, the cells were stained with 1 μM Topro-3 (Invitrogen) for 30 min; washed 2× with PBS; imaged with fixed gain and exposure settings; and the Hoechst staining of the Topro-3 stained nuclei quantified using CellProfiler software (www-.cellprofiler.org).

In Vitro Release by *Francisella novocida* vs. *Francisella tularensis*.

0.1 mg of MSN was pelleted by centrifugation and resuspended in PBS, PBS with $10^{10}$ live *Francisella tularensis* Live Vaccine Strain bacteria or PBS with $10^{10}$ live *Francisella novocida* bacteria per mL. After incubation at room temperature for 1 h, the bacteria and MSNs were pelleted by centrifugation and Hoechst fluorescence in the supernatant was measured with a Flexstation 384-well plate reader.

Measurement of Shedding of O-Antigen by *F. tularensis* LVS

Bacteria Grown on Plates

*F. tularensis* LVS was plated on chocolate agar, grown at 37° C. for 3 days, and individual colonies (100-200 colonies per 10 cm diameter plate) were transferred with a wire loop to 2 mL of Tris Buffered Saline (TBS) with 1% BSA and suspended evenly by gentle pipet action. Optical density at 540 nm of the suspension was determined by measurement of a diluted aliquot and used to estimate the number of bacteria per mL. The bacterial suspension was pelleted by centrifugation at 14,000 rcf for 10 min, the supernatant was saved and the pellet was resuspended in the original volume of TBS with 1% BSA. The supernatant and resuspended pellet were used for measurement of LPS in a competition ELISA using LPS (BEI Resources) diluted in TBS-1% BSA for the standard curve.

Bacteria Grown in Liquid Medium

Colonies of *F. tularensis* LVS grown on plates were inoculated into Trypticase Soy Broth with 0.2% cysteine (TSBC) at an optical density of 0.05 and grown at 37° C. to an optical density at 540 nm of 2. The bacteria were pelleted by centrifugation at 14,000 rcf for 10 min; the supernatant was saved and the pellet was resuspended in its original volume of TSBC. The supernatant and the resuspended pellet were used for measurement of LPS in a competition ELISA using LPS (BEI Resources) diluted in TSBC for the standard curve. All samples and standards contained 20 mM Tris HCl, pH 7.4, and 0.2% BSA.

Competition ELISA for Measurement of O-Antigen

Wells of high-binding 96-well ELISA plates were coated with purified LPS 1 μg/mL, 0.1 mL per well, in 0.05 M $NaHCO_3$, pH 9.6 for 3 h at room temperature. Wells were blocked with 1% BSA in TBS for 90 min at room temperature and washed 3 times with TBS. Standards (no LPS or purified LPS at concentrations of 0.4-12.5 μg/mL) and samples (100 μL volumes) were mixed with 25 μL of FB11 antibody at a final antibody concentration of 0.68 μg/mL in 125 μL in polypropylene, low-protein binding, 96-well plates and incubated for 90 min at room temperature. Aliquots of 90 μL of the FB11 antibody—LPS (sample or standard) reaction mixture were added to the LPS-precoated, blocked wells of the high-binding ELISA plate and incubated for 90 min at room temperature, washed four times with TBS, incubated with goat anti-mouse IgG polyperoxidase (1:2000 dilution, 90 per well) Pierce, Thermo Scientific), washed four times with TBS, and peroxidase detected using the TMB colorimetric substrate Kit (Thermo Scientific) according to the manufacturer's directions. The amount of LPS in the plate grown and TSBC grown samples was determined from log-log plots of absorbance vs. LPS standards prepared in TBS or TSBC, respectively.

Example 2

A Nanoparticle Platform for Detection and Response to Specific Pathogens

In this example, we describe the design and synthesis of a nanomaterial that can selectively and autonomously respond to a specific organism and signal its presence or kill it. In the area of human safety, this nanomaterial may be useful for detection of pathogens including disease-causing bacteria in general and *Francisella tularensis* (Ft) as a specific bio-warfare or bioterrorism threat. In one illustrative, but non-limiting embodiment, the nanomaterial consists of porous nanoparticles (e.g., mesoporous silica nanoparticles (MSNs)) with signaling or therapeutic molecules trapped in the pores of the nanoparticle by stimuli-responsive caps that are opened by a specific molecule produced by the targeted pathogen.

*Francisella tularensis*, the causative agent of tularemia, is a Tier 1 Select Agent of bioterrorism due to its high infectivity, capacity to cause serious morbidity and mortality, and the relative ease with which it can be cultured on a large scale, weaponized, and dispersed into the environment. Because it can be fatal even with appropriate therapy, there is a need for both detection and responsive therapeutic treatment modalities such as our triggered, pathogen-responsive cargo delivery platform. In addition to the specific response to a bio-warfare agent, treatment of infectious diseases in general could benefit tremendously from a delivery platform that releases its antibiotic payload only at the site of infection and only in the presence of the target pathogen, thereby minimizing off-target toxicities. Moreover, considering the ever-growing number of infections caused by antibiotic resistant strains of bacteria, many arising from the use of broad spectrum antibiotics, and the adverse health consequences arising from alterations of the human microbiome by such broad-spectrum antibiotics, there is a need for greater selectivity in targeting pathogenic bacteria. Since with our platform specificity and triggered release is based on the interaction between an antibody and a "target antigen", e.g., the highly specific O-Antigen chain of the Ft lipopolysaccharide (LPS), we believe that the same principles can also be applied to a variety of other gram-negative bacteria as well as other pathogens including Gram-positive bacteria and viruses against which a specific antibody can be generated, providing a new platform for pathogen-responsive detection and signaling of the presence of infectious organism.

We have demonstrated a highly pathogen-selective detection and delivery platform based on the interaction of an antibody nanovalve with the lipopolysaccharide (LPS) of *Francisella tularensis* (Ft) bacteria (see, e.g., FIG. 1). Because specificity and triggered release are based on the interaction between an antibody and the highly specific O-Antigen chain of the LPS, the same principles are readily applicable to other Gram-negative bacteria using antibodies specific to their LPS molecules. Moreover, the same principles can be applied to any other type of pathogen, e.g. Gram-positive bacteria, a virus, etc., so long as it is possible to generate a specific antibody to the pathogen. Our approach provides a new platform for pathogen-responsive cargo delivery for rapid simple one-step detection of pathogens and potentially highly pathogen-specific treatment of infectious diseases.

In one illustrative, but non-limiting embodiment, mesoporous silica nanoparticles (MSNs) provide an ideal platform for achieving pathogen-specific cargo release because their high internal porosity provides an enormous capacity for cargo loading and their surface is readily functionalized with environmentally responsive nanovalves to provide stimulus responsive release of cargo[2, 3].

Preliminary Results:

The design and synthesis of our pathogen-specific drug delivery platform involves multiple design features. First, it was necessary to consider the "container" used to hold the payload to be released specifically in the presence of the target pathogen. We chose mesoporous silica nanoparticles (MSNs) as the carriers due to their large internal pore volume and surface area, tunable particle size, pore size, and morphology, and huge flexibility for chemical modifications[4-8]. Next, we needed to address how a gatekeeping mechanism can be designed and implemented on this carrier that can act as a cap on the cargo-loaded pores and release the cargo selectively in response to a specific pathogen. In nature, one way that highly selective recognition of target pathogens is achieved is through antibody-antigen interactions, and indeed, MSN-antibody conjugates have been reported that were used for analyte detection[9-12], theranostics/imaging[12-17], or cell targeting[18-23]. However, these examples only demonstrate a specific recognition of an antigen by the MSN-antibody conjugate, but the recognition event itself does not stimulate a signal or killing response, i.e., there is no antigen-responsive gatekeeping mechanism that would selectively control cargo release only in the presence of a specific antigen or pathogen.

A design that we used to achieve a proactive response is one in which the antibody is bound to antigens immobilized on the surface of the MSNs, consequently acting as a "cap" that hinders the diffusion of cargo from the pores of the container. By manipulation of the surface-bound antigen such that the affinity of the antibody binding to it is reduced, the native antigen produced by the target pathogen can outcompete the modified surface-bound antigen for binding to the gatekeeper antibody, leading to displacement of the antibody cap and cargo release (FIG. 1). For the triggering event to occur, a way to "tune" the strong noncovalent antibody-antigen interaction is required such that a competitive displacement of the antibody cap occurs even at low antigen concentrations and at the same time there is minimal non-specific cargo release due to "leakage" from the delivery platform.

We have developed stimulus responsive MSNs wherein the MSNs are functionalized with a modified (acetylated) Ft LPS and the pores of the MSN are capped by anti-Ft LPS O-antigen antibody, such that native Ft LPS competes off the antibody, thereby opening the pores and releasing the cargo (FIG. 1). The anti-Ft LPS O-antigen antibody has a lower affinity for the acetylated than the native LPS O-antigen, thus allowing the native LPS (which is present on the surface of Ft and shed in abundance by Ft) to displace the antibody from the MSN, thereby opening the pores. We initially conjugated the whole Ft LPS molecule (which contains multiple repeating O-antigen tetrasaccharide units) to the MSN but found this to be unsatisfactory because it placed the terminal O-antigen tetrasaccharide (which is recognized by the anti-Ft LPS antibody) at too long a distance from the pore opening, allowing leakage of cargo from the pore even with the antibody still bound to it. e therefore used a molecular biology approach to delete the Ft wzy gene that encodes the O-antigen polymerase, allowing us to purify an LPS molecule with a single tetrasaccharide. We then removed the lipid A portion by gentle acid hydrolysis and coupled the resulting O-antigen tetrasaccharide and core unit to amine-functionalized MSNs, acetylated the bound O-antigen so as to slightly decrease the affinity of the antibody to it, loaded the MSNs with fluorescent cargo proteins (fluorescein or Hoechst dye), capped the pores with anti-Ft LPS O-antigen antibody and examined the release of Hoechst dye in response to environmental triggers.

As shown in FIG. 16, we observed a strong increase in fluorescein release after Ft-LPS addition indicating that the cargo was efficiently retained inside the porous MSNs by means of the antibody nanovalve; and that the MSNs released their cargo upon a specific stimulus, i.e., Ft-LPS. We also checked the selectivity of the nanovalve by comparing the release of a model drug in the presence of Ft-LPS vs. a different LPS from *Pseudomonas aeruginosa* (Pa) in which the O-antigen chain (as with Ft) also contains modified galactosamines and quinovosamines but still differs slightly in structure from Ft LPS. As expected from the highly specific nature of the antibody-antigen interaction, we observed a significant increase in cargo release only in the presence of Ft-LPS, and not in the presence of Pa-LPS. After these successful preliminary results with the cargo delivery platform, we further tested the specificity of cargo release using live bacteria by comparing cargo release by Ft with that of the very closely related bacterium *Francisella novicida* (Fn). Indeed, we observed a highly selective release of the Hoechst cargo when we incubated the MSNs with Ft but not with Fn or medium. These results demonstrate the feasibility and the high selectivity of our cargo delivery platform in vitro.

In our preliminary studies, we observed that utilization of O-antigen prepared from a wzy (O-antigen polymerase) knockout strain of *F. tularensis* Live Vaccine Strain (LVS Δwzy) in which the O-antigen portion of LPS is restricted to a single O-antigen tetrasaccharide greatly reduced leakiness and improved cargo loading compared with the much longer full length LPS. This result suggested to us that we would achieve further tightening of the capping of the pores, with corresponding improvements in loading and cargo retention, by additional shortening of the distance between the anti-Ft LPS antibody and the pore opening on the MSN surface, e.g. by eliminating the lipid A and the core components of the LPS molecule.

Hence, to bring the gatekeeper antibody even closer to the MSN surface, we deleted the gene waaL, whose product is responsible for transferring the O-antigen chain to the lipid A and core component of the LPS molecule. The resulting strain LVS Δwzy ΔwaaL produces O-antigen tetrasaccharides lacking the core and the lipid A portion of the LPS molecule. We have confirmed by Bligh-Dyer chloroform:methanol extraction and phase partitioning that the Δwzy ΔwaaL mutant accumulates very large amounts of anti-Ft LPS immunoreactive glycolipid consistent with the predicted undecaprenyl-diphospho-tetrasaccharide.

The undecaprenyl-diphospho-tetrasaccharide can be purified by DEAE-cellulose and C-18 reverse phase chromatography using the techniques published for purification of a chemically similar undecaprenyl-diphospho-trisaccharide[27]. Oxidative ozonolysis can be used to convert the undecaprenyl-diphospho-tetrasaccharide to the much smaller tetrasaccharide-diphosphoglycolic acid, which can be bound covalently by carbodiimide coupling to the surface of amine functionalized MSN. Dye loading and antibody capping can be done as described above. The methods described in FIG. 16 can be used to compare cargo (Hoechst dye) loading and specific O-antigen triggered release of MSNs functionalized with O-antigen prepared from the LVS Δwzy ΔwaaL mutant vs. the LVS Δwzy mutant. We believe that by eliminating the unnecessary core sugars, the LVS Δwzy ΔwaaL O-antigen material will improve the functionality of the O-antigen stimulus-responsive MSNs by providing tighter capping of the pores and less steric blocking to loading of the pores.

Biosensing Devices

The antibody nanogate can also be used as an autonomous amplified biosensing device where the Ft LPS antigen opens the gate and exposes an enzyme that functions as an amplifier that results in catalytic production of fluorescent molecules; these can then be readily detected. Traditional enzymatic amplification, such as ELISA, requires several steps: 1) incubation of sample with a solid phase; 2) washing away unbound sample; 3) adding antibody-enzyme conjugate; 4) washing away unbound antibody-enzyme conjugate; 5) addition of enzyme substrate; and 6) enzyme reaction product readout. In contrast, in our design, the analyte recognition process exposes the enzyme amplifiers and turns on enzyme catalyzed fluorophore generation in a single step. This design eliminates the need for washing or separation procedures and can dramatically increase the detection sensitivity.

We have demonstrated an example of this type of design, using a different capping mechanism. In those nanoparticles which consisted of two components: a mesoporous silica matrix with encapsulated enzyme (porcine liver esterase, PLE) in the pores, and a pH-responsive supramolecular nanogate assembly to control access of the enzyme to its substrate (5-carboxyfluorescein diacetate, CFDA). CFDA does not fluoresce before undergoing hydrolysis, but the product is strongly fluorescent. We first proved that the encapsulated enzymes retained their activity. Then, we showed that acidification activated the nanogate, exposed the enzymes, and initiated an autonomously amplified chemical sensing process.

In an illustrative, but non-limiting embodiment, the enzyme PLE into the MSN pores of the delivery vehicles described herein. Since this enzyme has a larger hydrodynamic diameter (~4 nm) than Hoechst dye its loading can be optimized by providing porous nanoparticle with a larger pore size (~4-6 nm) and the pores can be capped with the same tetrasaccharide described herein (1 nm length) in combination with bulky IgG molecules (14.5 nm×8.5 nm×4 nm, with Fab antigen binding sites 13.7 nm apart). This delivery vehicle, loaded with a detectable label, can be used to demonstrate tight loading of the PLE enzyme using the antibody cap, release of the enzyme upon addition of Ft, and an amplified signal from the subsequent catalysis of the enzyme substrate.

References for Example 2

1. Ruehle, B., Clemens, D. L., Lee, B. Y., Horwitz, M. A., and Zink, J. I. 2017. A Pathogen-Specific Cargo Delivery Platform Based on Mesoporous Silica Nanoparticles. J Am Chem Soc 139:6663-6668.
2. Lee, B.-Y., Li, Z., Clemens, D. L., Dillon, B. J., Hwang, A. A., Zink, J. I., and Horwitz, M. A. 2016. Redox-Triggered Release of Moxifloxacin from Mesoporous Silica Nanoparticles Functionalized with Disulfide Snap-Tops Enhances Efficacy Against Pneumonic Tularemia in Mice. Small 12:3690-3702.
3. Li, Z., Clemens, D. L., Lee, B.-Y., Dillon, B. J., Horwitz, M. A., and Zink, J. I. 2015. Mesoporous Silica Nanoparticles with pH-Sensitive Nanovalves for Delivery of Moxifloxacin Provide Improved Treatment of Lethal Pneumonic Tularemia. ACS Nano 9:10778-10789.
4. Ruehle, B., Saint-Cricq, P., and Zink, J. I. 2016. Externally Controlled Nanomachines on Mesoporous Silica Nanoparticles for Biomedical Applications. Chemphyschem: a European journal of chemical physics and physical chemistry 17:1769-1779.
5. Ambrogio, M. W., Thomas, C. R., Zhao, Y. L., Zink, J. I., and Stoddart, J. F. 2011. Mechanized silica nanoparticles: a new frontier in theranostic nanomedicine. Acc Chem Res 44:903-913.
6. Tarn, D., Ashley, C. E., Xue, M., Carnes, E. C., Zink, J. I., and Brinker, C. J. 2013. Mesoporous Silica Nanoparticle Nanocarriers: Biofunctionality and Biocompatibility. Acc Chem Res 46:792-801.
7. Argyo, C., Weiss, V., Brauchle, C., and Bein, T. 2014. Multifunctional Mesoporous Silica Nanoparticles as a Universal Platform for Drug Delivery. Chemistry of Materials 26:435-451.
8. Li, Z., Barnes, J. C., Bosoy, A., Stoddart, J. F., and Zink, J. I. 2012. Mesoporous silica nanoparticles in biomedical applications. Chem Soc Rev 41:2590-2605.
9. Tao, L., Zhang, C., Zhang, J., Sun, Y., Li, X., Yan, K., Jin, B., Zhang, Z., and Yang, K. 2016. Sensitive chemiluminescence immunoassay for staphylococcal enterotoxin C1 based on the use of dye-encapsulated mesoporous silica nanoparticles. Microchimica Acta 183:2163-2168.
10. Ma, H., Wang, Y., Wu, D., Zhang, Y., Gao, J., Ren, X., Du, B., and Wei, Q. 2016. A Novel Controlled Release Immunosensor based on Benzimidazole Functionalized SiO2 and Cyclodextrin Functionalized Gold. Scientific reports 6:19797.
11. Eum, J. Y., Hwang, S. Y., Ju, Y., Shim, J. M., Piao, Y., Lee, J., Kim, H. S., and Kim, J. 2014. A highly sensitive immunoassay using antibody-conjugated spherical mesoporous silica with immobilized enzymes. Chem Commun (Camb) 50:3546-3548.
12. Erathodiyil, N., and Ying, J. Y. 2011. Functionalization of inorganic nanoparticles for bioimaging applications. Acc Chem Res 44:925-935.
13. Chiu, H. Y., Deng, W., Engelke, H., Helma, J., Leonhardt, H., and Bein, T. 2016. Intracellular chromobody delivery by mesoporous silica nanoparticles for antigen targeting and visualization in real time. Scientific reports 6:25019.
14. Knezevic, N. Z., and Durand, J. O. 2015. Large pore mesoporous silica nanomaterials for application in delivery of biomolecules. Nanoscale 7:2199-2209.
15. Chen, F., Nayak, T. R., Goel, S., Valdovinos, H. F., Hong, H., Theuer, C. P., Barnhart, T. E., and Cai, W. 2014. In vivo tumor vasculature targeted PET/NIRF imaging with TRC105(Fab)-conjugated, dual-labeled mesoporous silica nanoparticles. Mol Pharm 11:4007-4014.
16. Milgroom, A., Intrator, M., Madhavan, K., Mazzaro, L., Shandas, R., Liu, B., and Park, D. 2014. Mesoporous silica nanoparticles as a breast-cancer targeting ultrasound contrast agent. Colloids and surfaces. B, Biointerfaces 116:652-657.
17. Lei, C., Liu, P., Chen, B., Mao, Y., Engelmann, H., Shin, Y., Jaffar, J., Hellstrom, I., Liu, J., and Hellstrom, K. E. 2010. Local release of highly loaded antibodies from functionalized nanoporous support for cancer immunotherapy. J Am Chem Soc 132:6906-6907.
18. Gao, Y., Gu, S., Zhang, Y., Xie, X., Yu, T., Lu, Y., Zhu, Y., Chen, W., Zhang, H., Dong, H., Sinko, P. J., and Jia, L. 2016. The Architecture and Function of Monoclonal Antibody-Functionalized Mesoporous Silica Nanoparticles Loaded with Mifepristone: Repurposing Abortifacient for Cancer Metastatic Chemoprevention. Small 12:2595-2608.
19. Zhang, Y., Guo, J., Zhang, X. L., Li, D. P., Zhang, T. T., Gao, F. F., Liu, N. F., and Sheng, X. G. 2015. Antibody fragment-armed mesoporous silica nanoparticles for the targeted delivery of bevacizumab in ovarian cancer cells. Int J Pharm 496:1026-1033.
20. Zhang, H., Ding, Q., and Ding, J. 2016. Noninvasive target CT detection and anti-inflammation of MRSA pneumonia with theranostic silver loaded mesoporous silica. RSC Advances 6:5049-5056.
21. Ngamcherdtrakul, W., Morry, J., Gu, S., Castro, D. J., Goodyear, S. M., Sangvanich, T., Reda, M. M., Lee, R., Mihelic, S. A., Beckman, B. L., Hu, Z., Gray, J. W., and Yantasee, W. 2015. Cationic Polymer Modified Mesoporous Silica Nanoparticles for Targeted SiRNA Delivery to HER2+ Breast Cancer. Adv Funct Mater 25:2646-2659.
22. Chen, F., Hong, H., Shi, S., Goel, S., Valdovinos, H. F., Hernandez, R., Theuer, C. P., Barnhart, T. E., and Cai, W. 2014. Engineering of hollow mesoporous silica nanoparticles for remarkably enhanced tumor active targeting efficacy. Scientific reports 4:5080.
23. Tsai, C.-P., Chen, C.-Y., Hung, Y., Chang, F.-H., and Mou, C.-Y. 2009. Monoclonal antibody-functionalized mesoporous silica nanoparticles (MSN) for selective targeting breast cancer cells. Journal of Materials Chemistry 19:5737-5743.
24. Climent, E., Bernardos, A., Martinez-Máñez, R. n., Maquieira, A., Marcos, M. D., Pastor-Navarro, N., Puchades, R., Sancenon, F. 1., Soto, J., and Amoros, P. 2009. Controlled Delivery Systems Using Antibody-Capped Mesoporous Nanocontainers. J. Am. Chem. Soc. 131:14075-14080.
25. Climent, E., Martinez-Manez, R., Maquieira, A., Sancenon, F., Marcos, M. D., Brun, E. M., Soto, J., and Amoros, P. 2012. Antibody-capped mesoporous nanoscopic materials: design of a probe for the selective chromo-fluorogenic detection of finasteride. Chemistry Open 1:251-259.
26. Climent, E., Groninger, D., Hecht, M., Walter, M. A., Martinez-Manez, R., Weller, M. G., Sancenon, F., Amoros, P., and Rurack, K. 2013. Selective, sensitive, and rapid analysis with lateral-flow assays based on antibody-gated dye-delivery systems: the example of triacetone triperoxide. Chemistry 19:4117-4122.
27. Li, L., Woodward, R. L., Han, W., Qu, J., Song, J., Ma, C., and Wang, P. G. 2016. Chemoenzymatic synthesis of the bacterial polysaccharide repeating unit undecaprenyl pyrophosphate and its analogs. Nat Protoc 11:1280-1298.
28. Xue, M., and Zink, J. I. 2013. An enzymatic chemical amplifier based on mechanized nanoparticles. J Am Chem Soc 135:17659-17662.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An antigen- or pathogen-specific delivery vehicle, said vehicle comprising:
    a porous nanoparticle where said porous nanoparticle comprises a plurality of pores where said pores provide a pore surface inside the particle, and where said porous nanoparticle comprises an outer nanoparticle surface through which said pores are disposed;
    a cargo disposed in said pores;
    one or more antigens attached to the outer surface of said nanoparticle, wherein said one or more antigens each comprise a single tetrasaccharide unit of an O-antigen from a gram-negative bacterium; and
    antibodies that specifically bind said antigens attached to the outer surface of said nanoparticle where said antibodies are bound to said attached antigens and inhibit diffusion of said cargo out of said pores and permit release of said cargo when said delivery vehicle is in the presence of a free form of said antigen or a pathogen displaying said antigen.

2. A pharmaceutical formulation, said formulation comprising:

a vehicle of claim 1; and a pharmaceutically acceptable carrier/excipient.

3. The delivery vehicle of claim 1, wherein said antigen is acetylated.

4. The delivery vehicle of claim 1, wherein said porous nanoparticle comprises a particle selected from the group consisting of a mesoporous silica nanoparticle, mesoporous hollow silica nanoparticle, and a mesoporous organosilica nanoparticle.

5. The delivery vehicle of claim 1, wherein said cargo comprises a detectable label or an agent that kills a microorganism.

6. The delivery vehicle of claim 1, wherein said antigen is acetylated.

7. The delivery vehicle of claim 1, wherein said porous nanoparticle comprises a particle selected from the group consisting of a mesoporous silica nanoparticle, mesoporous hollow silica nanoparticle, and a mesoporous organosilica nanoparticle.

8. The delivery vehicle of claim 1, wherein said cargo comprises a detectable label selected from the group consisting of an enzymatic label, a substrate for an enzymatic label, a fluorophore, a colorimetric label, and a radioactive label.

9. The delivery vehicle of claim 1, wherein said antigen comprises a single O-antigen serotype.

10. The delivery vehicle of claim 1, wherein said antigen comprises a plurality of O-antigen serotype(s).

11. The delivery vehicle of claim 1, wherein said antigen comprises an O-antigen selected from the group consisting of Franciscella O-antigen, *Acinetobacter* O-antigen, *Actinobacillus* O-antigen, *Bordetella* O-antigen, *Brucella* O-antigen, *Campylobacter* O-antigen, Cyanobacteria O-antigen, *Enterobacter* O-antigen, *Erwinia* O-antigen, *Escherichia coli* O-antigen, *Helicobacter* O-antigen, Hemophilus O-antigen, *Klebsiella* O-antigen, *Legionella* O-antigen, *Moraxella* O-antigen, *Neisseria* O-antigen, *Pasteurella* O-antigen, *Proteus* O-antigen, *Pseudomonas* O-antigen, *Salmonella* O-antigen, *Serratia* O-antigen, *Shigella* O-antigen, *Treponema* O-antigen, *Vibrio* O-antigen, and *Yersinia* O-antigen.

12. An antigen- or pathogen-specific delivery vehicle, said vehicle comprising:
   a porous nanoparticle where said porous nanoparticle comprises a plurality of pores where said pores provide a pore surface inside the particle, and where said porous nanoparticle comprises an outer nanoparticle surface through which said pores are disposed;
   a cargo disposed in said pores, where said cargo comprises a detectable label;
   one or more antigens attached to the outer surface of said nanoparticle, wherein said one or more antigens comprise a single tetrasaccharide unit of an O-antigen from a gram-negative bacterium; and
   antibodies that specifically bind said antigens attached to the outer surface of said nanoparticle where said antibodiesand are bound to said attached antigens and inhibit, diffusion of said cargo out of said pores and permit release of said cargo when said delivery vehicle is in the presence of a free form of said antigen or a pathogen displaying said antigen.

13. The delivery vehicle of claim 12, wherein said porous nanoparticle comprises a particle selected from the group consisting of a mesoporous silica nanoparticle, mesoporous hollow silica nanoparticle, and a mesoporous organosilica nanoparticle.

14. The delivery vehicle of claim 12, wherein said cargo comprises a detectable label selected from the group consisting of an enzymatic label, a substrate for an enzymatic label, a fluorophore, a colorimetric label, and a radioactive label.

15. The delivery vehicle of claim 12, wherein said antigen comprises a single O-antigen serotype.

16. The delivery vehicle of claim 12, wherein said antigen comprises an O-antigen selected from the group consisting of Franciscella O-antigen, *Acinetobacter* O-antigen, *Actinobacillus* O-antigen, *Bordetella* O-antigen, *Brucella* O-antigen, *Campylobacter* O-antigen, Cyanobacteria O-antigen, *Enterobacter* O-antigen, *Erwinia* O-antigen, *Escherichia coli* O-antigen, *Helicobacter* O-antigen, Hemophilus O-antigen, *Klebsiella* O-antigen, *Legionella* O-antigen, *Moraxella* O-antigen, *Neisseria* O-antigen, *Pasteurella* O-antigen, *Proteus* O-antigen, *Pseudomonas* O-antigen, *Salmonella* O-antigen, *Serratia* O-antigen, *Shigella* O-antigen, *Treponema* O-antigen, *Vibrio* O-antigen, and *Yersinia* O-antigen.

17. The delivery vehicle of claim 12, wherein said cargo comprises a fluorophore or an enzymatic label, or a substrate for an enzymatic label.

18. A method of preparing a delivery vehicle, said method comprising:
   providing a porous nanoparticle comprising a plurality of pores and an outer surface through which said pores are disposed and an antigen attached to the surface of said nanoparticle, wherein said antigen comprises a single tetrasaccharide unit of an O-antigen from a gram-negative bacterium;
   loading a cargo into the pores comprising said porous nanoparticle; and
   contacting said nanoparticle with an antibody that binds to said antigen thereby sealing said cargo into the pores of said nanoparticle.

* * * * *